US011262367B2

(12) United States Patent
Shastry et al.

(10) Patent No.: US 11,262,367 B2
(45) Date of Patent: Mar. 1, 2022

(54) OPTICAL READER FOR ANALYTE TESTING

(71) Applicant: Evanostics LLC, Los Gatos, CA (US)

(72) Inventors: Ashutosh Shastry, Santa Clara, CA (US); David Piehler, Los Gatos, CA (US); Hardeep Sanghera, San Jose, CA (US); Michael Gluzczack, Los Gatos, CA (US); Pranav Chopra, Los Gatos, CA (US); Yun-Pei Chang, Arcadia, CA (US); Ameya Kantak, Los Gatos, CA (US)

(73) Assignee: Evanostics LLC, Los Gatos, CA (US)

(*) Notice: Subject to any disclaimer, the term of this patent is extended or adjusted under 35 U.S.C. 154(b) by 395 days.

(21) Appl. No.: 16/223,096

(22) Filed: Dec. 17, 2018

(65) Prior Publication Data

US 2019/0187162 A1 Jun. 20, 2019

Related U.S. Application Data

(60) Provisional application No. 62/599,671, filed on Dec. 15, 2017, provisional application No. 62/599,674, filed on Dec. 15, 2017.

(51) Int. Cl.
*G01N 33/94* (2006.01)
*G01N 33/487* (2006.01)
*G01N 21/64* (2006.01)

(52) U.S. Cl.
CPC ......... *G01N 33/94* (2013.01); *G01N 21/6445* (2013.01); *G01N 33/487* (2013.01); *G01N 2021/6439* (2013.01); *G01N 2201/0221* (2013.01); *G01N 2201/0612* (2013.01)

(58) Field of Classification Search
CPC ... G01N 2021/6439; G01N 2021/6484; G01N 21/6445; G01N 21/648; G01N 2201/0221; G01N 2201/0612; G01N 33/487; G01N 33/94; Y10T 436/2575
USPC ....... 422/82.05, 82.08, 82.11, 502, 503, 504, 422/505; 436/43, 46, 63, 164, 165, 172, 436/180
See application file for complete search history.

(56) References Cited

U.S. PATENT DOCUMENTS

| 3,792,699 A | 2/1974 | Tobin et al. |
| 5,520,787 A | 5/1996 | Hanagan et al. |
| 5,827,675 A | 10/1998 | Skiffington et al. |

(Continued)

FOREIGN PATENT DOCUMENTS

| EP | 1178316 B1 | 1/2005 |
| EP | 1899450 A2 | 3/2008 |

(Continued)

OTHER PUBLICATIONS

Shastry et al.; U.S. Appl. No. 16/040,506 entitled "Cartridges for oral fluid analysis and methods of use," filed Jul. 19, 2018.

(Continued)

*Primary Examiner* — Maureen Wallenhorst
(74) *Attorney, Agent, or Firm* — Shay Glenn LLP

(57) ABSTRACT

Analyte collection and testing systems and methods, and more particularly to disposable oral fluid collection and testing systems and methods. Described herein are methods and apparatuses to achieve significant improvements in the detection of fluorescence signals in the reader.

40 Claims, 54 Drawing Sheets

(56) References Cited

U.S. PATENT DOCUMENTS

| | | |
|---|---|---|
| 6,416,642 B1 | 7/2002 | Alajoki et al. |
| 6,635,226 B1 | 10/2003 | Tso et al. |
| 6,716,392 B1 | 4/2004 | Putcha et al. |
| 6,942,771 B1 | 9/2005 | Kayyem |
| 7,029,627 B2 | 4/2006 | Alley |
| 7,105,355 B2 | 9/2006 | Kurabayashi et al. |
| 7,294,502 B2 | 11/2007 | Eckermann et al. |
| 7,374,723 B2 | 5/2008 | Wuske et al. |
| 7,618,591 B2 | 11/2009 | Slowey et al. |
| 7,708,945 B1 | 5/2010 | Abel et al. |
| 7,713,703 B1 | 5/2010 | Buechler et al. |
| 7,741,103 B2 | 6/2010 | Guirgus |
| 7,781,226 B2 | 8/2010 | McDevitt et al. |
| 7,790,400 B2 | 9/2010 | Jehanli et al. |
| 7,837,939 B2 | 11/2010 | Tung et al. |
| 7,888,040 B2 | 2/2011 | Jehanli |
| 7,888,130 B2 | 2/2011 | Wuske et al. |
| 7,927,548 B2 | 4/2011 | Slowey et al. |
| 7,955,558 B2 | 6/2011 | Weekamp et al. |
| 8,025,849 B2 | 9/2011 | Baldwin et al. |
| 8,025,851 B2 | 9/2011 | Slowey et al. |
| 8,101,431 B2 | 1/2012 | McDevitt et al. |
| 8,105,849 B2 | 1/2012 | McDevitt et al. |
| 8,174,700 B2 | 5/2012 | Chinowsky et al. |
| 8,222,024 B2 | 7/2012 | Davis et al. |
| 8,273,305 B2 | 9/2012 | Slowey et al. |
| 8,288,157 B2 | 10/2012 | Duer |
| 8,300,993 B2 | 10/2012 | Moll et al. |
| 8,331,751 B2 | 12/2012 | Delaney et al. |
| 8,506,898 B2 | 8/2013 | Perez |
| RE44,539 E | 10/2013 | Thompson et al. |
| 8,586,347 B2 | 11/2013 | Lochhead et al. |
| 8,675,199 B2 | 3/2014 | Duer |
| 8,881,580 B2 | 11/2014 | Lundgreen et al. |
| 8,906,303 B2 | 12/2014 | Ermantraut et al. |
| 9,012,163 B2 | 4/2015 | Burd et al. |
| 9,034,634 B2 | 5/2015 | Miller |
| 9,040,288 B2 | 5/2015 | Handique et al. |
| 9,072,425 B1 | 7/2015 | Bogema |
| 9,176,126 B2 | 11/2015 | Holmes et al. |
| 9,179,895 B2 | 11/2015 | Jowett et al. |
| 9,193,996 B2* | 11/2015 | Buermann ......... G01N 21/6486 |
| 9,194,859 B2 | 11/2015 | Emeric et al. |
| 9,198,641 B2 | 12/2015 | Slowey et al. |
| 9,204,865 B2 | 12/2015 | Polzius et al. |
| 9,212,995 B2 | 12/2015 | Moll et al. |
| 9,267,939 B2 | 2/2016 | Campbell et al. |
| 9,417,210 B2 | 8/2016 | Arlen et al. |
| 9,423,397 B2 | 8/2016 | Duer |
| 9,528,939 B2 | 12/2016 | Duer |
| RE46,351 E | 3/2017 | Apel et al. |
| 9,658,222 B2 | 5/2017 | Moll et al. |
| 9,709,580 B2 | 7/2017 | McDevitt et al. |
| 9,841,396 B2 | 12/2017 | Miller et al. |
| 9,846,126 B2 | 12/2017 | Gunn et al. |
| 9,919,313 B2* | 3/2018 | Lowe ............... G01N 33/54386 |
| 2003/0175947 A1 | 9/2003 | Liu et al. |
| 2006/0150385 A1 | 7/2006 | Gilligan et al. |
| 2006/0216196 A1 | 9/2006 | Satoh et al. |
| 2006/0257854 A1 | 11/2006 | McDevitt et al. |
| 2006/0257941 A1 | 11/2006 | McDevitt et al. |
| 2006/0257991 A1 | 11/2006 | McDevitt et al. |
| 2006/0292034 A1 | 12/2006 | Gould et al. |
| 2006/0292040 A1 | 12/2006 | Wickstead et al. |
| 2007/0263049 A1 | 11/2007 | Preckel et al. |
| 2011/0028346 A1 | 2/2011 | Chakravarty et al. |
| 2011/0201099 A1* | 8/2011 | Anderson ............ G01F 23/292 435/287.2 |
| 2011/0253224 A1 | 10/2011 | Linder et al. |
| 2012/0282154 A1 | 11/2012 | Slowey et al. |
| 2013/0102003 A1 | 4/2013 | Gibbs |
| 2013/0309778 A1 | 11/2013 | Lowe et al. |
| 2013/0331298 A1 | 12/2013 | Rea |
| 2015/0010903 A1 | 1/2015 | Schawaller et al. |
| 2015/0111778 A1 | 4/2015 | McDevitt et al. |
| 2015/0346097 A1 | 12/2015 | Battrell et al. |
| 2015/0352549 A1 | 12/2015 | Kolb et al. |
| 2016/0033412 A1 | 2/2016 | Tan et al. |
| 2016/0157836 A1 | 6/2016 | Borg et al. |
| 2016/0187239 A1 | 6/2016 | Givens et al. |
| 2016/0331356 A1 | 11/2016 | Binner et al. |
| 2016/0344156 A1 | 11/2016 | Rothberg et al. |
| 2017/0014822 A1 | 1/2017 | Ker |
| 2017/0016827 A1 | 1/2017 | Gervais et al. |
| 2017/0023477 A1 | 1/2017 | Duer et al. |
| 2017/0045507 A1 | 2/2017 | Khattak et al. |
| 2017/0120238 A1 | 5/2017 | Bodner |
| 2017/0370836 A1 | 12/2017 | Gerion et al. |
| 2018/0021783 A1* | 1/2018 | Arlett ................... B01L 3/527 435/287.2 |
| 2018/0062748 A1 | 3/2018 | Mack et al. |
| 2018/0275058 A1* | 9/2018 | Stern .................. G01N 21/69 |
| 2019/0021704 A1* | 1/2019 | Shastry ............... G01N 33/948 |
| 2020/0296454 A1 | 9/2020 | Shastry et al. |

FOREIGN PATENT DOCUMENTS

| | | |
|---|---|---|
| EP | 2596121 A2 | 5/2013 |
| EP | 2616797 B1 | 1/2017 |
| EP | 2627987 B1 | 9/2017 |
| WO | WO2005/072398 A2 | 8/2005 |
| WO | WO2005/083423 A2 | 9/2005 |
| WO | WO2009/012307 A2 | 1/2009 |
| WO | WO2012/032294 A1 | 3/2012 |
| WO | WO2016/019026 A1 | 2/2016 |
| WO | WO2016/138427 A1 | 9/2016 |
| WO | WO2017/059425 A1 | 4/2017 |
| WO | WO2018/015931 A1 | 1/2018 |
| WO | WO2020/132146 A1 | 6/2020 |

OTHER PUBLICATIONS

Chuang et al.; Development and qualification of a mechanical-optical interface for parallel optics links; InOptical Interconnects XV; International Society for Optics and Photonics; vol. 9368: p. 936811,8 pages; Apr. 3, 2015.

Schoellner et al.; A mechanical-optical interface for 25+ Gbps VCSEL/PD fiber coupling; InOptical Interconnects XVII; International Society for Optics and Photonics; vol. 10109; p. 101090C; 13 pages; Feb. 20. 2017.

Stanford Research Systems, Inc.: About lock-in Amplifiers: Application Note #3; retrieved from the internet at: (https://www.thinksrs.com/downloads/pdfs/applicationnotes/AboutLIAs.pdf); 9 pages: on Feb. 25, 2021.

* cited by examiner

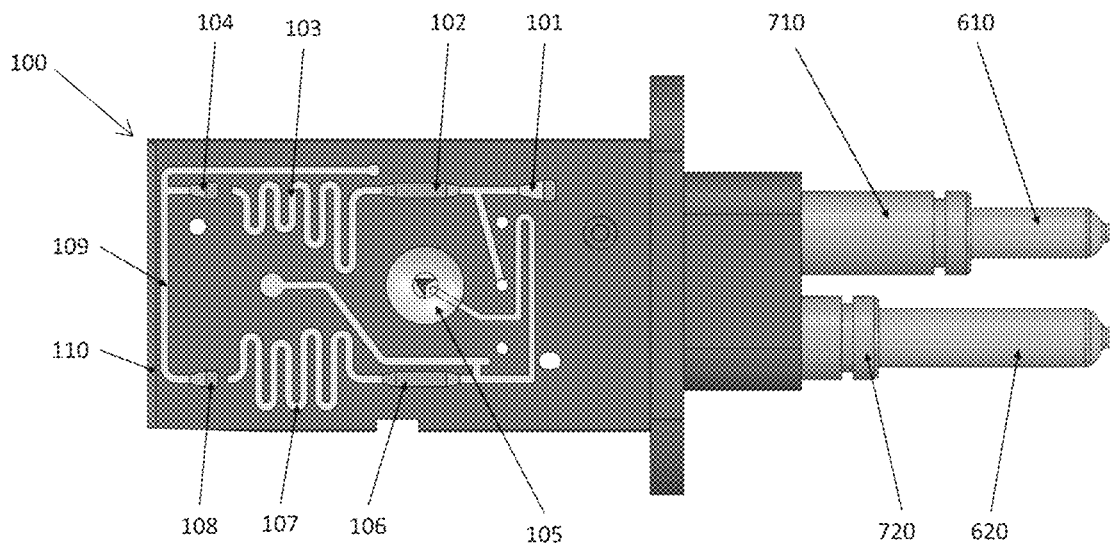
FIG. 4A
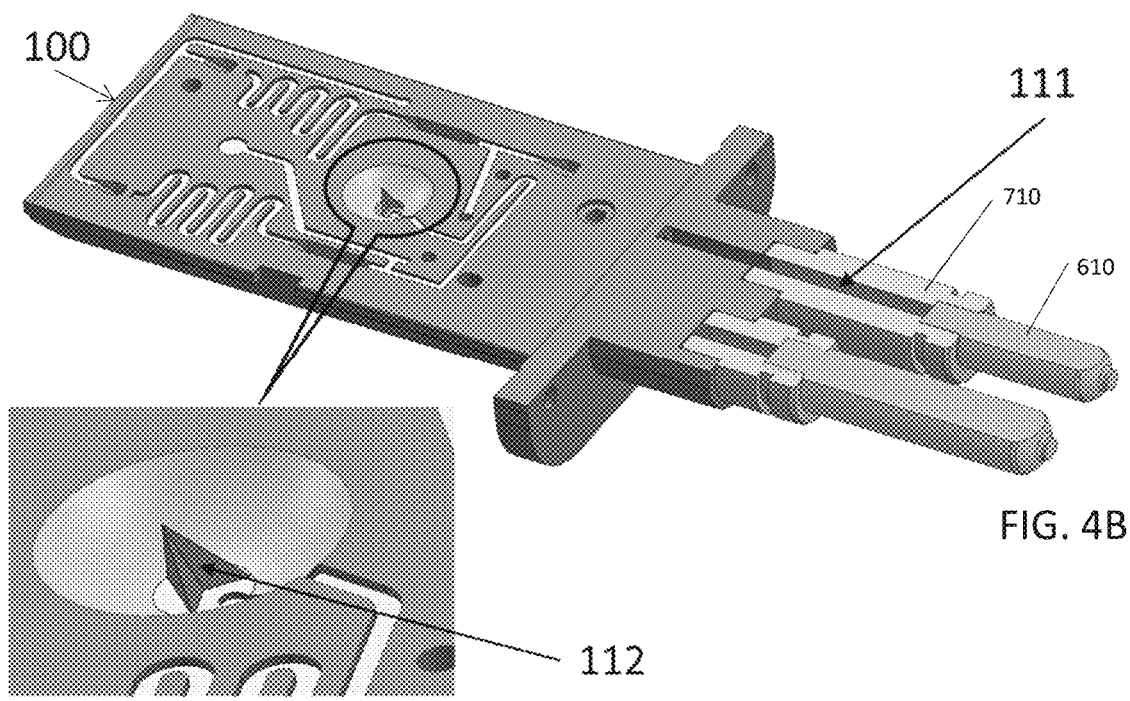
FIG. 4B
FIG. 4C

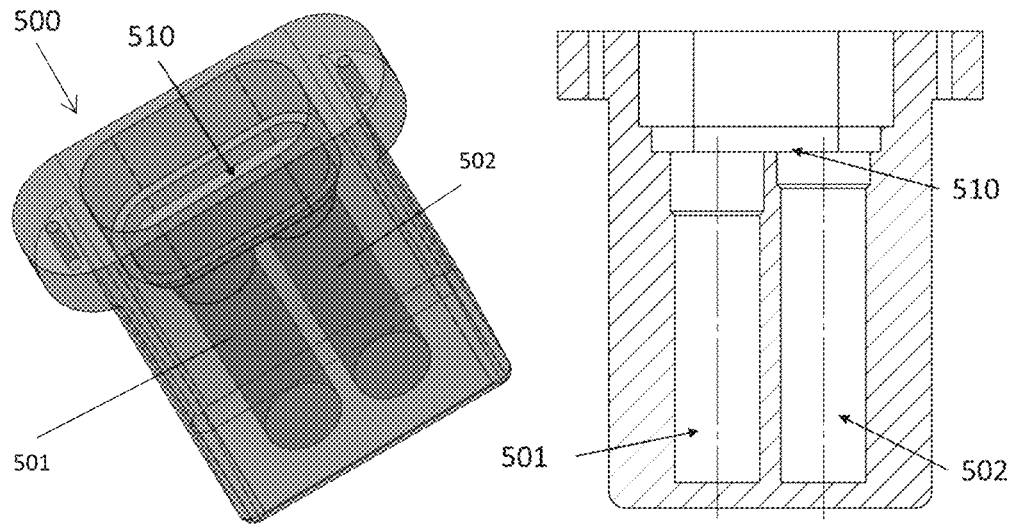
FIG. 6A    FIG. 6B
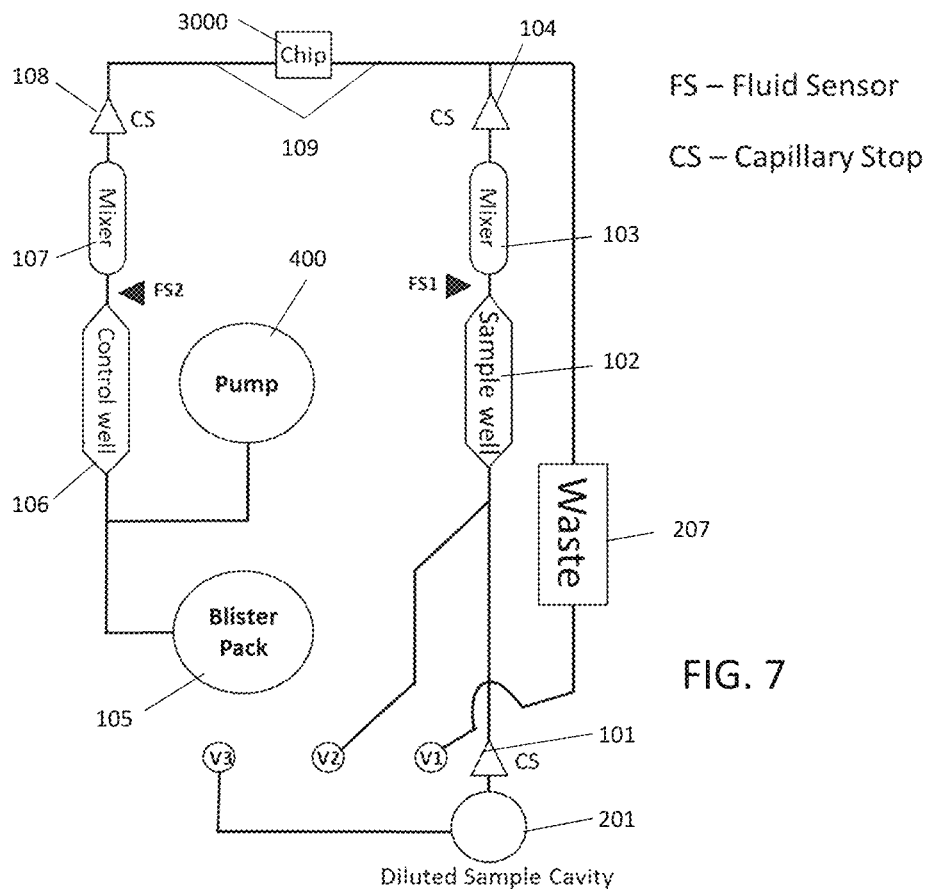
FIG. 7

| ASSAY | SIGNAL CUT-OFF | RESOLUTION | FALSE POSITIVE AT 0.6X | FALSE NEGATIVE AT 1.4X | FALSE POSITIVE AT 0.25X | FALSE NEGATIVE AT 1.75X |
|---|---|---|---|---|---|---|
| BZO | 0.52 | 0.32 | 2% | 2% | 0.005% | 0.642% |
| THC | 0.71 | 0.18 | 6% | 4% | 0.033% | 0.001% |
| COC | -0.19 | 0.24 | 4% | 6% | 0.000% | 0.000% |

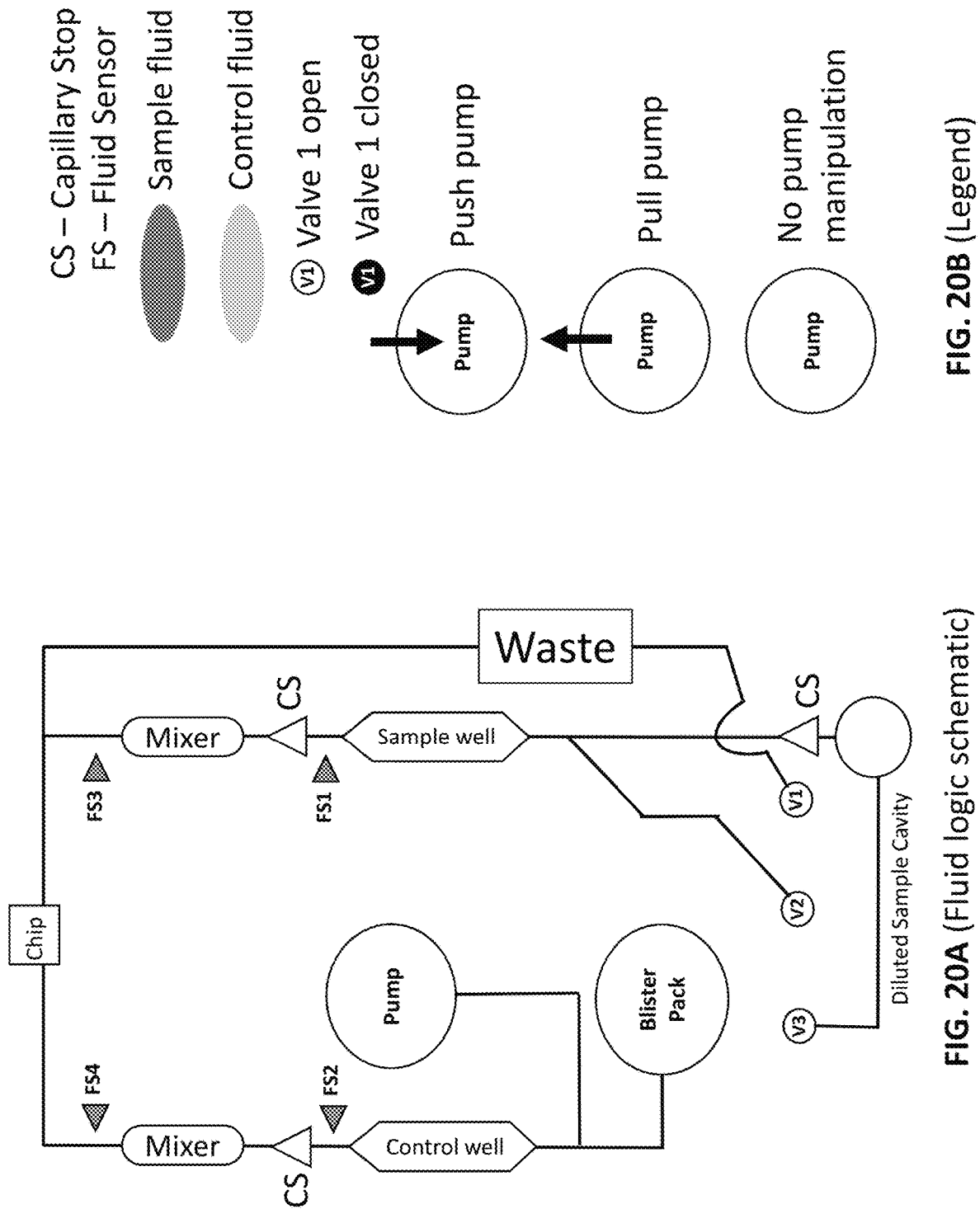
FIG. 20A (Fluid logic schematic)
FIG. 20B (Legend)

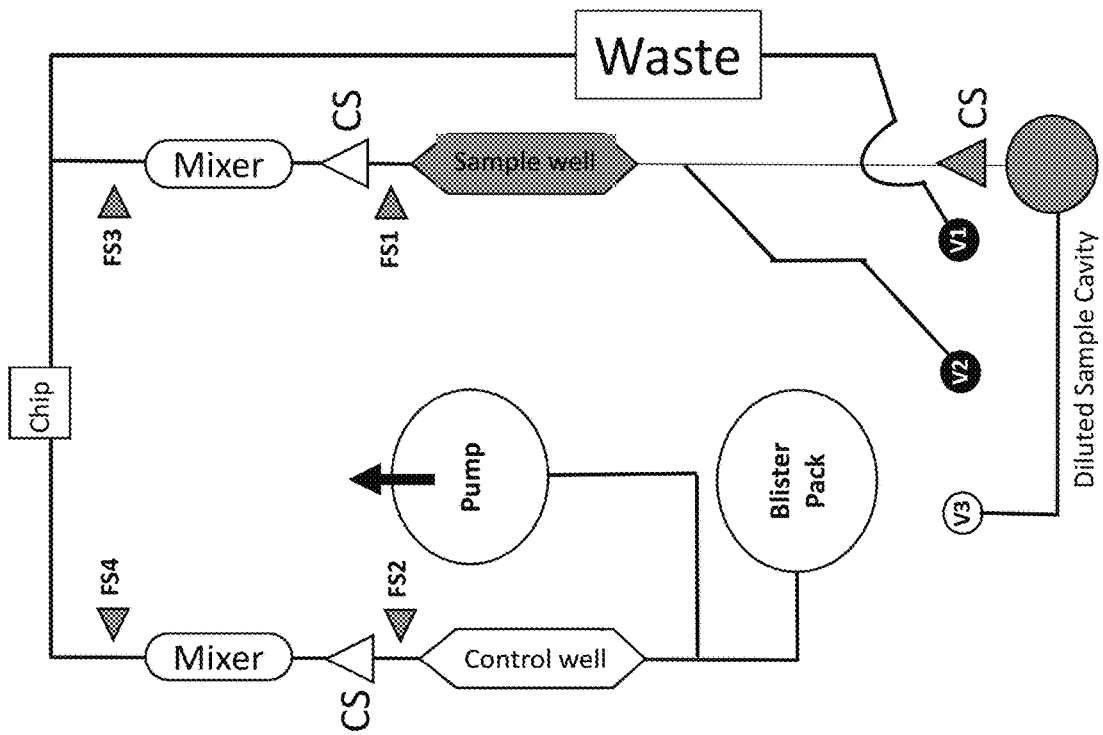
FIG. 20D (Sample Metering)
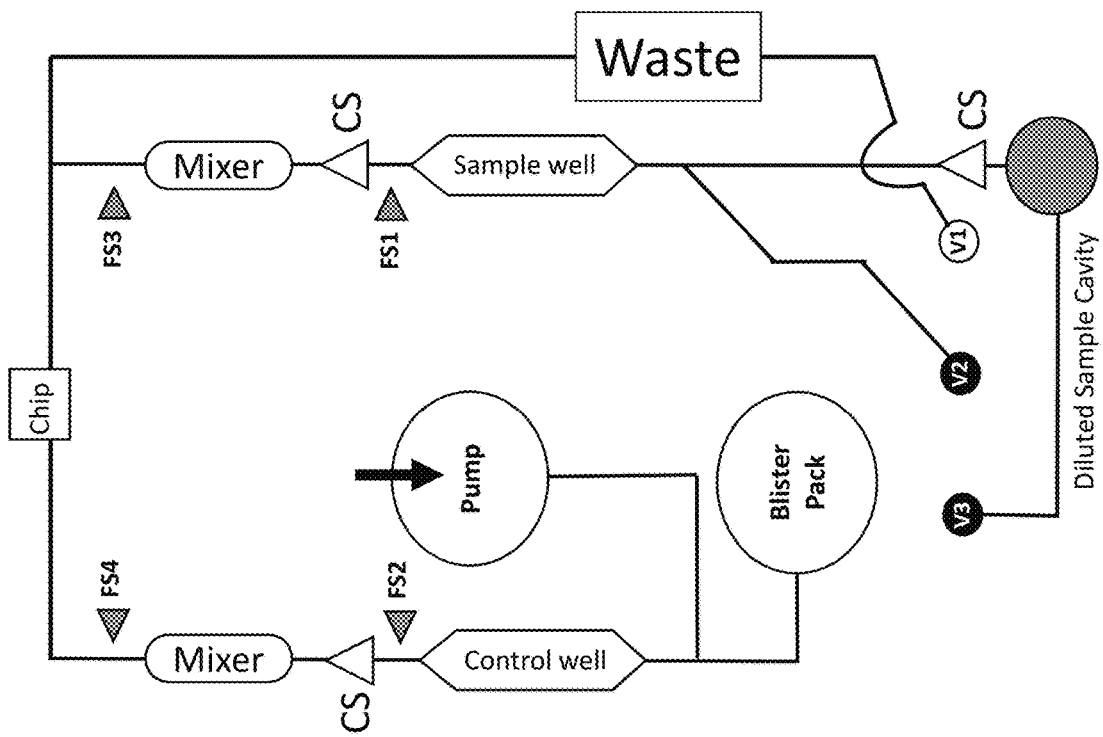
FIG. 20C (Prime pump)

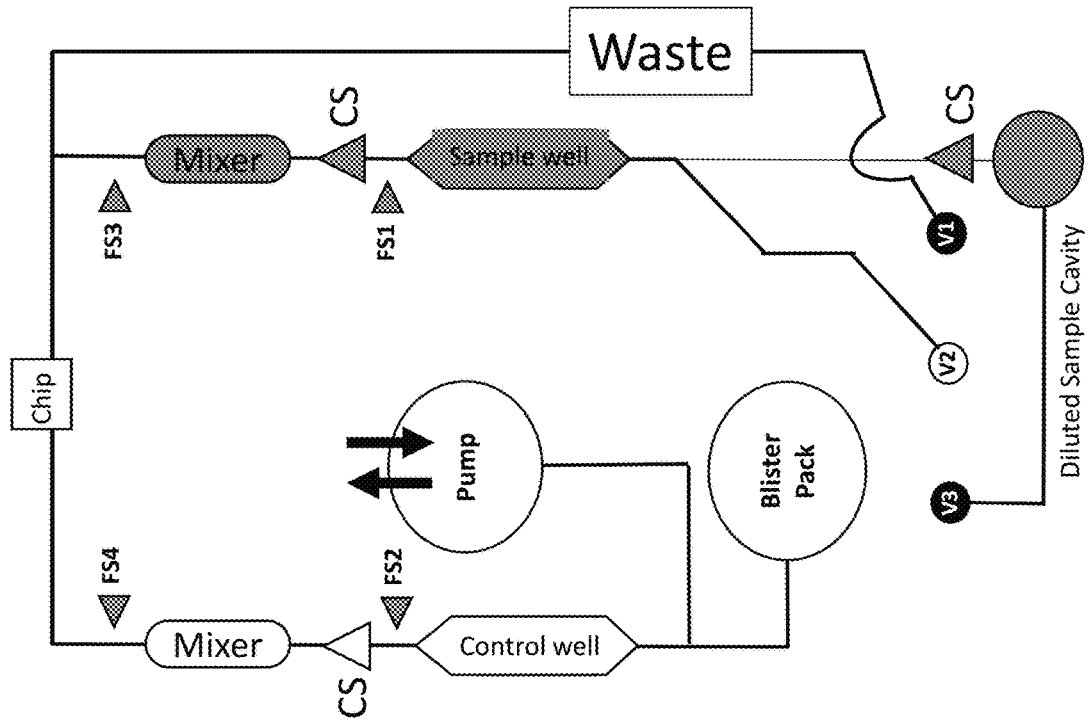
FIG. 20F (Mix)
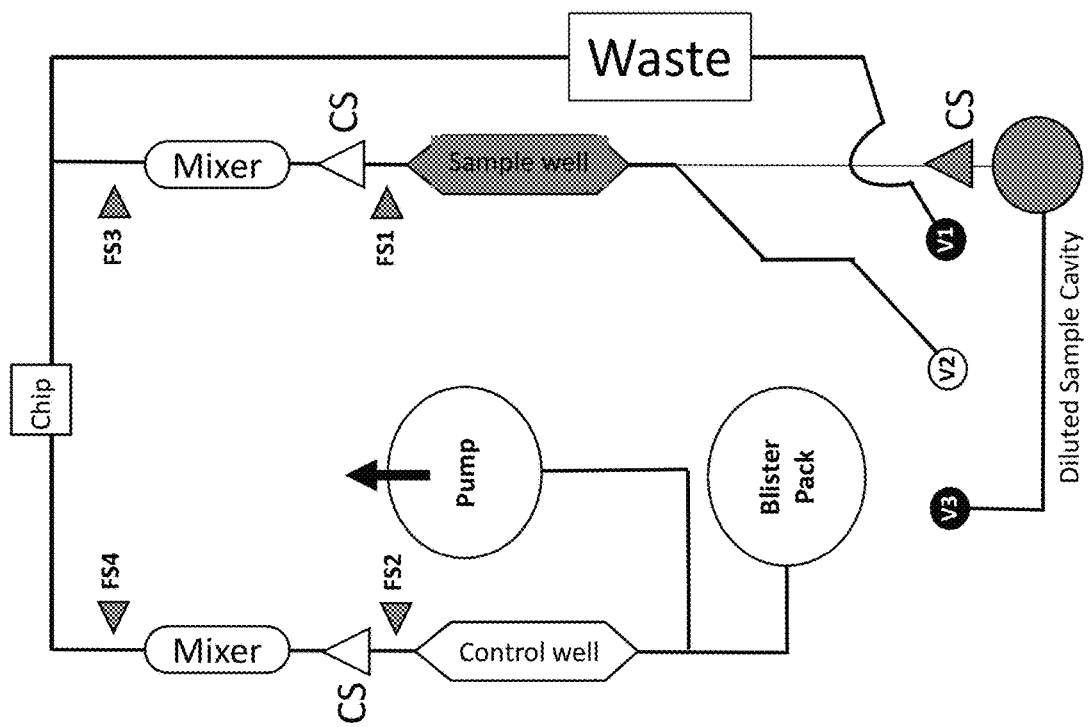
FIG. 20E (Cleave)

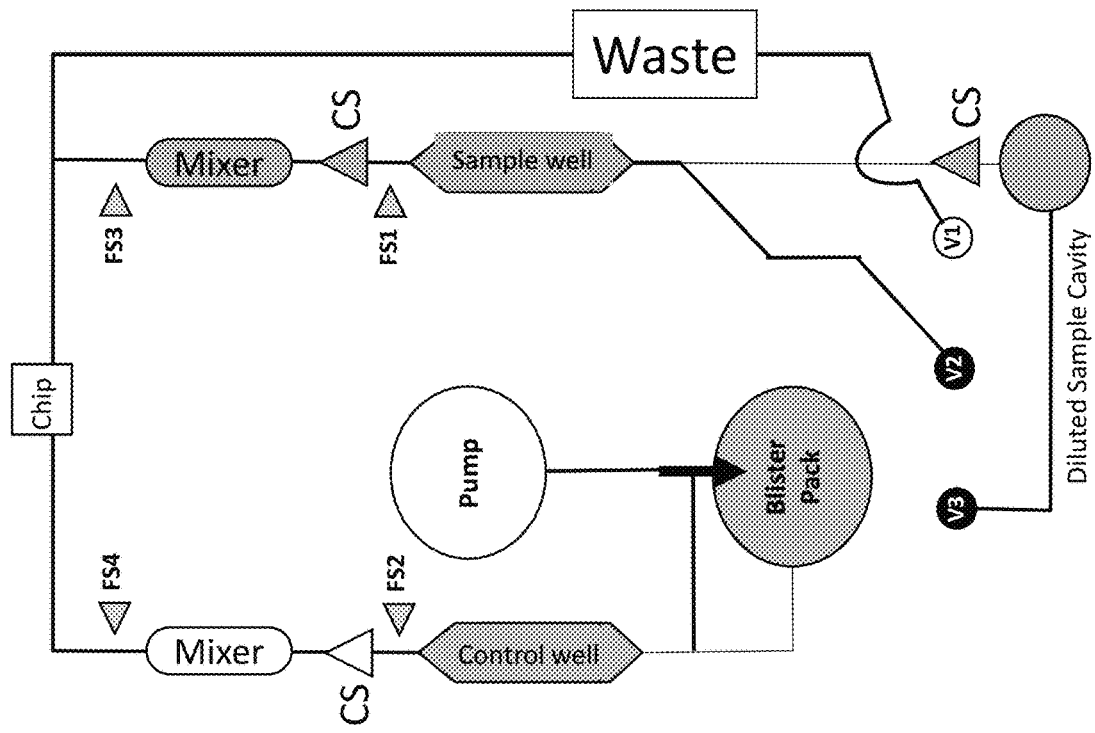
FIG. 20H (meter control)
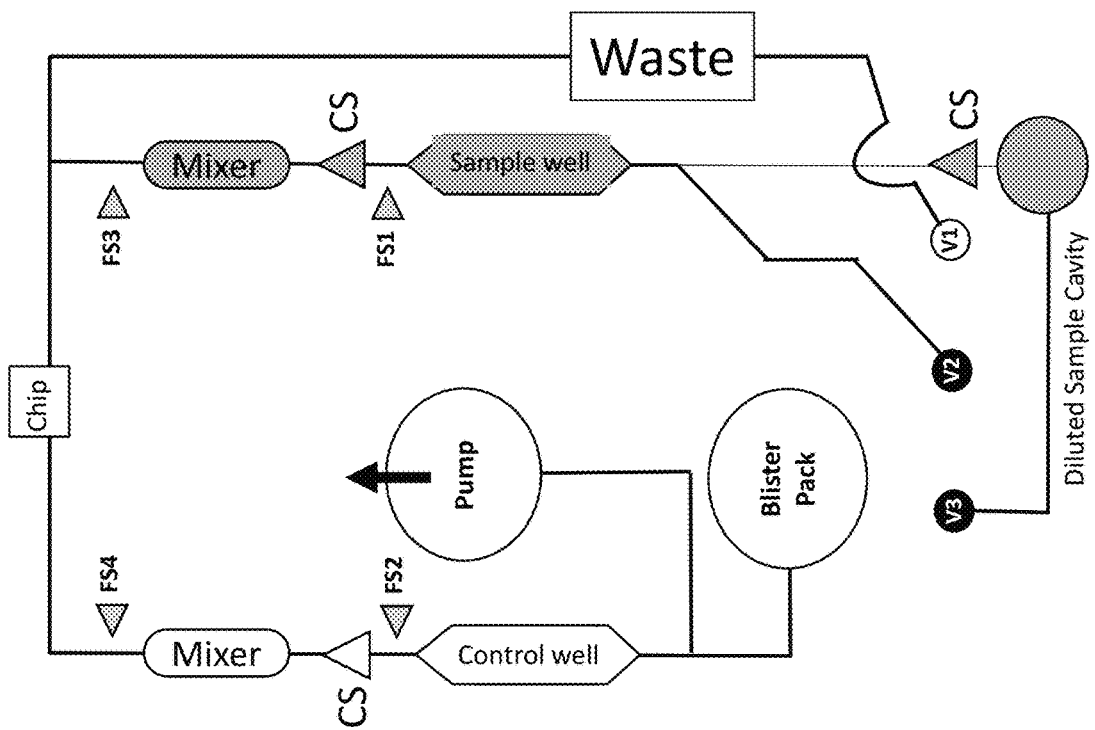
FIG. 20G (release pump)

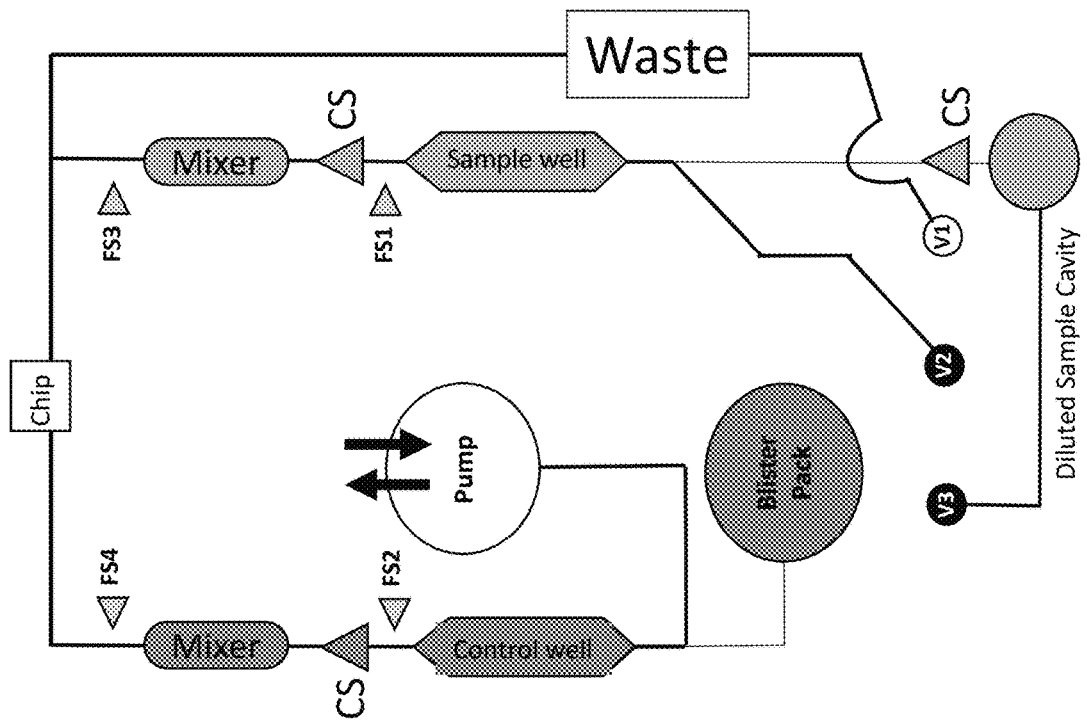
FIG. 20J (mix control)
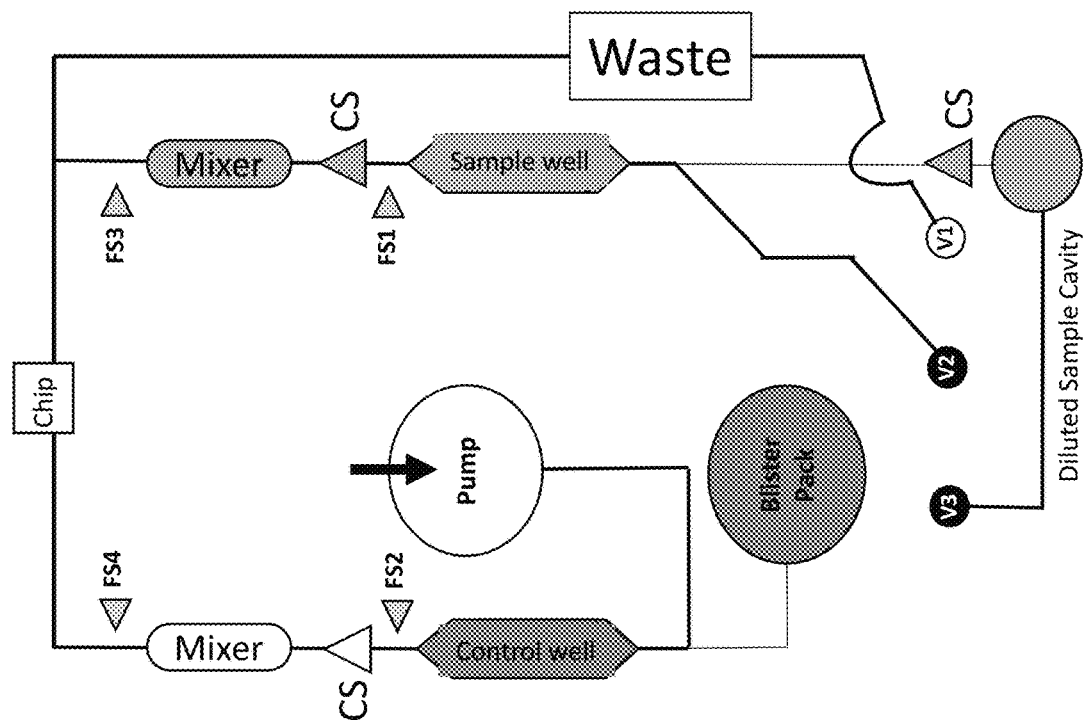
FIG. 20I (cleave control)

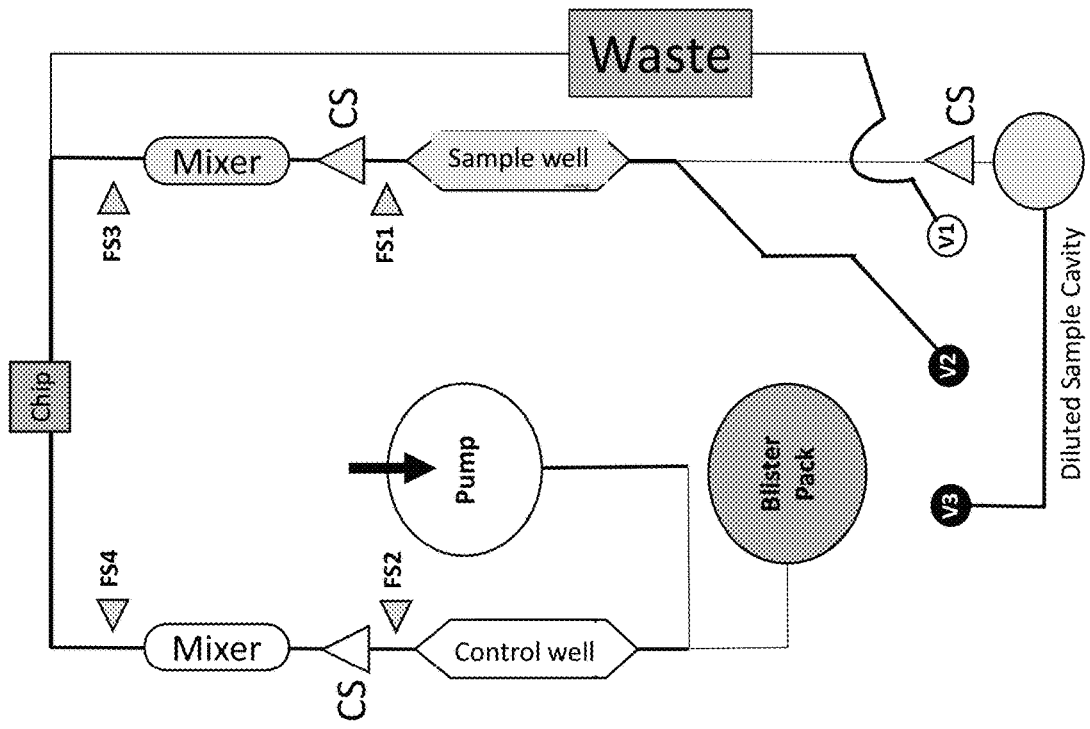
FIG. 20L (Empty control)
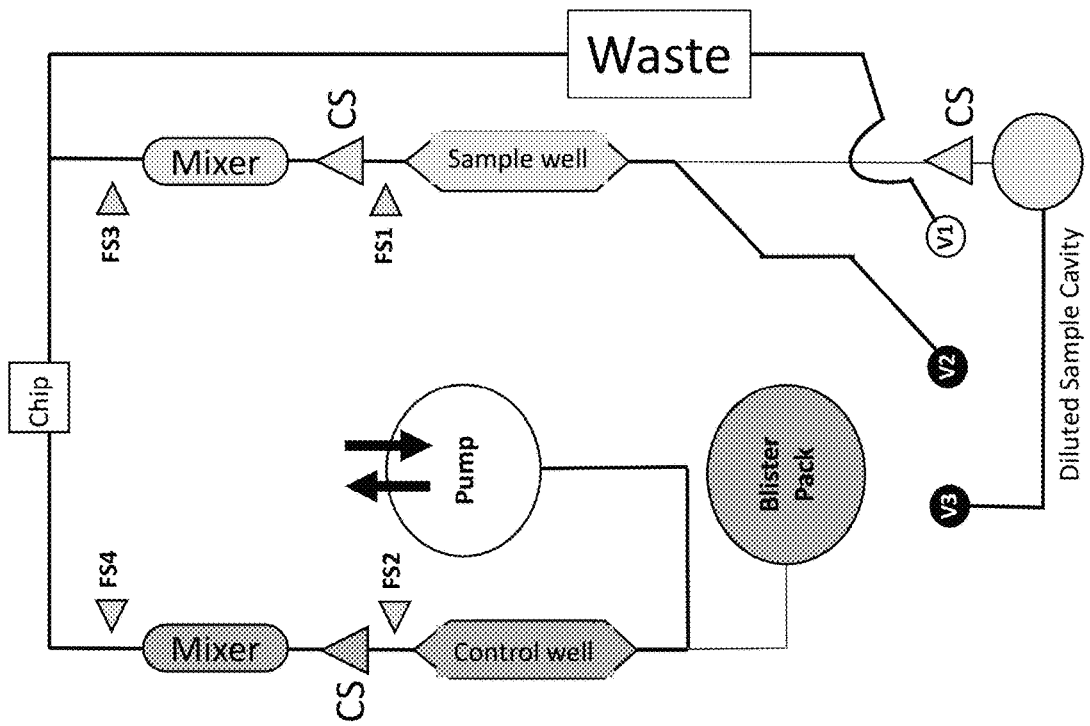
FIG. 20K (test control)

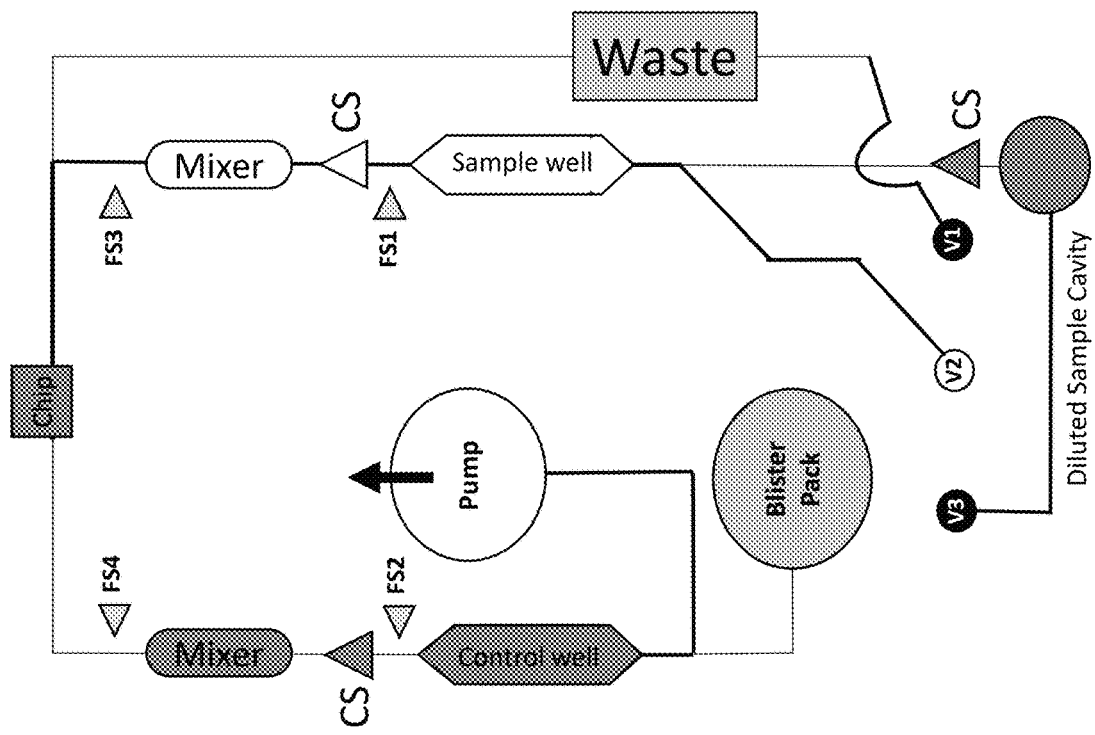
FIG. 20N (Empty sample)
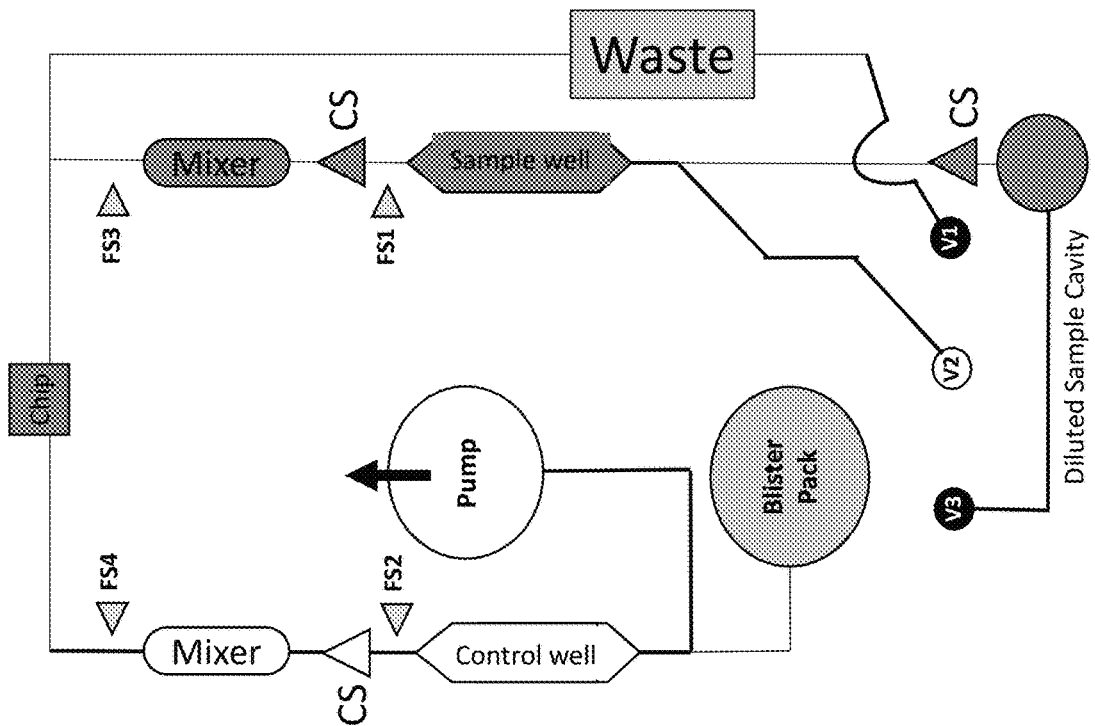
FIG. 20M (test sample)

Front perspective

Front perspective

Back perspective

Side back

Front

Top

Bottom

US 11,262,367 B2

OPTICAL READER FOR ANALYTE TESTING

CROSS REFERENCE TO RELATED APPLICATIONS

This patent application claims priority to U.S. Provisional Patent Application No. 62/599,671, filed on Dec. 15, 2017 (titled "POLARIZATION MAINTAINING OPTICAL PATH FOR ENSURING READER TO READER CONSISTENCY") and U.S. Provisional Patent Application No. 62/599,674, field on Dec. 15, 2017 (titled "CLAMP DESIGN FOR PRECISION ALIGNMENT OF THE CARTRIDGE"), each of which is herein incorporated by reference in its entirety This patent application may also be related to U.S. patent application Ser. No. 16/040,506, filed on Jul. 19, 2018, and now U.S. Pat. No. 10,660,619, titled ("CARTRIDGES FOR ORAL FLUID ANALYSIS AND METHODS OF USE"), which claims priority to U.S. Provisional Patent Application No. 62/534,394, titled "ORAL FLUID ANALYZING SYSTEMS AND METHODS" and filed Jul. 19, 2017.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Embodiments of the invention relate generally to analyte collection and testing systems and methods, and more particularly to disposable oral fluid collection and testing systems and methods. Described herein are methods and apparatuses to achieve significant improvements in the detection of fluorescence signals in the reader.

BACKGROUND

Detection of analytes, particularly for drugs of abuse, is important in various workplace drug testing settings, such as for pilots, professional athletes, and law enforcement, and to detect driving under the influence of drugs (DUID). Detection of these analytes in oral fluid, i.e. saliva, provides a more convenient method of sample collection than collection of blood or urine.

Conventionally, the collected samples are sent to a certified testing laboratory for analysis. However, sending the samples to the lab and then waiting for the lab to process and testing the sample and then report the results can take a significant amount of time, typically at least days. In many situations, it would be desirable to have testing results at the point of testing instead of waiting days for results from the lab. This would allow, for example, an airline to prevent pilots under the influence of drugs to fly a plane, thereby improving safety.

Tools for reading a sample-containing cartridge (e.g., a "reader") may utilize a detection scheme utilizing an optical sensor for reading the cartridge.

SUMMARY OF THE DISCLOSURE

Described herein are methods and apparatuses for how to achieve robust optical performance of a sample cartridge reader with the use of polarization maintaining components in the optical path. The inherent nature of the optical coupling to almost any photonic chip is highly polarization dependent in addition to the propagation through waveguides and also evanescent coupling of light to molecules, including biological molecules. Thus by fixing the polarization state of all four excitation channels to the optical transverse-magnetic (TM) polarization as described herein, we may achieve optimal and reliable performance of our system.

This embodiment of the invention utilizes polarization-maintaining optical components in the optical path of the reader hardware. The excitation laser may be pigtailed with a polarization maintaining fiber and the scan head fiber is also polarization maintaining. With electromagnetic (EM) simulations of the photonic chip, we obtain the optimal polarization state (TM) to use with this photonic chip architecture. This leads to a stable and repeatable known polarization state of light exiting the scan head and coupling into the photonic chip.

Also described herein are methods and apparatuses for use with analyte holding cartridges.

For example, described herein are optical reader devices for reading a photonic chip of a removable cartridge. An optical reader device may include: a cartridge holder comprising a slot extending into the reader, the slot having a height and a width; a scan head, wherein the scan head comprises a first plurality of optical fiber ends that are optically connected to one or more laser light sources and a second plurality of fiber ends that are optically connected to a plurality of detectors; a scan head actuator configured to move the scan head relative to the cartridge holder; a plurality of valves on the cartridge holder that are configured to couple with valve openings in the removable cartridge; a pump membrane actuator on the cartridge holder that is configured to apply force to a membrane pump of the removable cartridge, wherein the pump membrane actuator is configured to hold a plurality of extended positions to deflect or relax deflection of the membrane pump; and a controller configured to coordinate movement of the scan head, illumination of the one or more laser light sources, detection by the plurality of detectors, opening and closing of the plurality of valves and positioning of the pump membrane actuator when the removable cartridge is inserted into the cartridge holder.

An optical reader device for reading a photonic chip of a removable cartridge may include: a reader housing including a cartridge interface comprising an opening into the reader housing; a cartridge holder comprising a slot extending into the reader from the cartridge interface, the slot having a height and a width; a scan head within the reader housing, wherein the scan head comprises a first plurality of optical fiber ends that are optically connected to one or more laser light sources and a second plurality of fiber ends that are optically connected to a plurality of detectors, further wherein the optical fiber ends within the first and second plurality of optical fiber ends are arranged in a line; a scan head actuator configured to move the scan head relative to the cartridge holder; a plurality of valves on the cartridge holder that are configured to couple with valve openings in the removable cartridge; a pump membrane actuator comprising a rocker arm having a rounded end, wherein the pump membrane actuator is configured to apply force to a membrane pump of the removable cartridge, wherein the pump membrane actuator is configured to hold a plurality of extended positions to deflect or relax deflection of the membrane pump; and a controller configured to coordinate movement of the scan head, illumination of the one or more laser light sources, detection by the plurality of detectors, opening and closing of the plurality of valves and positioning of the pump membrane actuator when the removable cartridge is inserted into the cartridge interface.

In any of these variations, the device may also include one or more (e.g., a plurality of) fluid sensors in communication with the controller and configured to optically detect fluid within one or more regions of the removable cartridge. The controller may be configured to clamp the cartridge holder when the removable cartridge is inserted in to the cartridge holder. For example, the cartridge holder may include a movable/lockable base that may be driven to clamp the cartridge in position.

The scan head may include a linear array of the first plurality of optical fiber ends and the second plurality of optical fiber ends. A fiber mount holder may hold the ends of the fibers (and in some variations a lens or lensing material, filter, etc.) to the scan head.

Each valve of the plurality of valves may comprise a seal configured to be moved relative to the cartridge holder to open or close a valve opening in the removable cartridge when the removable cartridge is held within the cartridge holder. The seal may block or unblock an opening (valve opening) on a cartridge.

The pump membrane actuator may be any appropriate actuator (e.g., mechanical, electromechanical, pneumatic, etc.), for example, the pump membrane actuator may comprise an arm and a driver. The pump membrane actuator may comprise a rounded, ball-shaped end. In some variations the pump membrane actuator comprises a rocker arm that is motor driven.

Any of these device may include a second actuator, such as a blister pack arm on the cartridge holder, that is configured to apply force to a blister pack of the removable cartridge (e.g., to open/break the blister pack).

Any of these devices may include a temperature sensor on the cartridge holder and a heater on the cartridge holder, wherein the controller is further configured to regulate a temperature of a removable cartridge held in the cartridge holder.

In any of these variations, the reader may be configured for precise control of the alignment of the cartridge relative to the scan head. For example, described herein are optical reader devices for reading a photonic chip of a removable cartridge that include: a cartridge holder comprising a slot extending in a z-axis into the reader, the slot having a height in the y-axis direction and a width in the x-axis direction, a ball plunger on one side of the slot, the ball plunger biased to extend into the slot in the x-axis direction, configured to drive the removable cartridge against a reference surface in the z-axis and a reference surface in the x-axis; a movable clamp base configured to apply force in the y-axis to secure the removable cartridge within the slot and to drive the removable cartridge against a reference surface in the y-axis; a scan head configured to move relative to the cartridge holder, wherein the scan head comprises a first plurality of fiber ends optically connected to one or more laser light sources and a second plurality of fiber ends optically connected to a plurality of detectors; and a controller configured to coordinate movement of the movable clamp, movement of the scan head, illumination of the one or more laser light sources and detection by the plurality of detectors.

For example, an optical reader device for reading a photonic chip of a removable cartridge may include: a reader housing including a cartridge interface comprising an opening into the reader housing; a cartridge holder comprising a slot extending in a z-axis into the reader, the slot having a height in the y-axis direction and a width in the x-axis direction, a ball plunger on one side of the slot, the ball plunger biased to extend into the slot in the x-axis direction, configured to drive the removable cartridge against a reference surface in the z-axis and a reference surface in the x-axis; a movable clamp base configured to apply force in the y-axis to secure the removable cartridge within the slot and to drive the removable cartridge against a reference surface in the y-axis; a scan head configured to move relative to the cartridge holder, wherein the scan head comprises a first plurality of fiber ends optically connected to one or more laser light sources and a second plurality of fiber ends optically connected to a plurality of detectors; a pump membrane actuator configured to apply force to a membrane pump of the removable cartridge, wherein the pump membrane actuator is configured to hold a plurality of extended positions to deflect or relax deflection of the membrane pump; and a controller configured to coordinate movement of the movable clamp, movement of the scan head, illumination of the one or more laser light sources and detection by the plurality of detectors.

In some variations the reference surface in the z-axis is a pin extending into the cartridge slot.

Any of these devices may further include a scan head actuator configured to move the scan head relative to the cartridge holder. The scan head actuator may be a motor.

As mentioned above, any of these devices may include one or a plurality of valves on the cartridge holder that are configured to couple with valve openings in the removable cartridge. The devices may include a pump membrane actuator on the cartridge holder that is configured to apply force to a membrane pump of the removable cartridge, wherein the pump membrane actuator is configured to hold a plurality of extended positions to deflect or relax deflection of the membrane pump. For example, the pump membrane actuator may comprise an arm and a driver. Any of the pump membrane actuators may have an end that contacts the pump membrane that is configured to uniformly apply force (or to distribute the force) to the pump membrane to prevent damaging it. In some variations the pump membrane actuator comprises a rounded, ball-shaped end. In some variations the pump membrane actuator comprises a rocker arm that is motor driven.

As mentioned, any of these devices may include a plurality of fluid sensors in communication with the controller and configured to optically detect fluid within one or more regions of the removable cartridge. The controller may be configured to clamp the movable clamp base to apply force in the y-axis to secure the removable cartridge when the removable cartridge is inserted in to the cartridge holder.

The scan head may comprise a linear array of the first plurality of optical fiber ends and the second plurality of optical fiber ends, as described above.

Any of these devices may include a second actuator (similar to the pump membrane actuator) that is configured to rupture one or more blister packs on the cartridge. For example, any of these apparatuses may include a blister pack arm on the cartridge holder configured to apply force to a blister pack of the removable cartridge.

The devices described herein may include one or more temperature sensors on the cartridge holder and/or a heater on the cartridge holder, wherein the controller is further configured to regulate a temperature of a removable cartridge held in the cartridge holder.

Any of the optical reader devices described herein may be part of a system that may further include one or more cartridges as described herein. Any of the reader variations described herein may be used with any of these cartridges to form a system; one or more additional components (outputs, displays, user interface software, etc.) may also be included.

Also described herein are devices (e.g., optical reader devices) for reading a photonic chip of a removable cartridge that are configured to control the polarization of the energy applied so that it matches the inherent polarization of the photonic chip. For example described herein are optical reader devices comprising: a scan head; a plurality of laser sources each configured to emit light having a TM polarization; a first plurality of optical fibers, wherein each laser source is coupled to one optical fiber of the first plurality of optical fibers, further wherein the first plurality of optical fibers are polarization maintaining single-mode fibers; a plurality of optical sensors; a second plurality of optical fibers, wherein each optical sensor is coupled to one optical fiber of the second plurality of optical fibers, further wherein the second plurality of optical fibers are multimode fibers; wherein each of the first plurality of optical fibers and the second plurality of optical fibers terminates on the scan head so that an end of each optical fiber of the first and second pluralities of optical fibers are arranged in a line facing a gap; and a cartridge holder configured to receive the removable cartridge so that the photonic chip is aligned with a polarization axis formed by the scan head so that an end of the photonic chip comprising a plurality of waveguides faces the gap, across from the scan head, wherein the device is configured to maintain the polarization of the polarization axis in a transverse-magnetic (TM) polarization.

The laser sources may comprise one or more diode lasers. The second plurality of fibers may contain at least twice as many optical fibers as the first plurality of fibers (e.g., there may be two optical fibers in the first plurality and four optical fibers in the second plurality, there may be four optical fibers in the first plurality and nine optical fibers in the second plurality, etc.).

The controller may be configured to control alignment of the scan head relative to the cartridge. For example, the cartridge holder may be configured to clamp the cartridge to prevent it from moving. In some variations, the cartridge holder may be configured to bias the cartridge in a direction that is normal to a major plane of the cartridge (e.g., in a y-axis direction) against a reference surface to prevent movement of the cartridge as one or more actuators apply force to the cartridge to drive fluid through the cartridge. This may reduce or eliminate misalignment of the chip relative to the scan head during operation. In any of these variations, the controller may be configured to adjust the position of the scan head during operation of the device by actuating a scan head actuator to align the ends of the optical fibers with waveguides of the photonic chip when the cartridge is in the cartridge holder.

Also described herein are methods of operation of any of the devices and systems described. For example, a method of reading optical signals from a photonic chip of a removable cartridge head in an optical reader may include: aligning a scan head of the optical reader with the chip so that the chip and a laser source, a plurality of fibers, and an optical sensor of the scan head are aligned along a polarization axis with the chip; maintaining a polarization of the polarization axis in a transverse-magnetic (TM) polarization; emitting one or more beams of light from the laser, through the plurality of fibers and into an edge of the photonic chip in the TM polarization; and detecting, in the optical sensor, TM polarized light from one or more waveguides within the chip when the one or more beams of light interact with an analyte molecule on the chip.

Any of these methods may include inserting a cartridge containing the chip into the optical reader.

Emitting may comprise emitting a plurality of concurrent beams of TM polarized light from the scan head, into the edge of the photonic chip.

Maintaining the polarization of the polarization axis comprises maintaining the polarization of the plurality of fibers (e.g., the first and/or second plurality of fibers).

The method may also comprise polarizing light emitted from the scan to the edge of the chip in a polarizer.

The methods described herein may also include adjusting the alignment of the scan head while emitting and/or detecting to maintain the TM polarization.

Any of the methods described herein may include inserting the cartridge into the reader device. Any of these methods may include clamping the cartridge and/or aligning the cartridge within the cartridge holder (e.g., clamp). For example, the cartridge may be inserted so that a ball plunger rides against a wall of the cartridge until it reaches a seating edge of the cartridge, when a back surface (e.g., a z-face) of the cartridge contacts a reference surface. The ball plunger may drive the cartridge against two or more seating surfaces, including a seating surface in the x-axis and the back (z-face) seating surface(s). Once seated, the controller may then lock the cartridge into position by clamping a y-face seating surface (e.g., a bottom of the cartridge holder) against the cartridge. The controller may control alignment of the scan head with the photonics chip, as described herein. The controller may coordinate fluid control of the cartridge and testing (applying light and detecting signals). For example, the controller may coordinate one or more of: puncturing one or more blister pack, moving the control solutions, moving the sample, dissolving reagents (e.g., labeled antibodies for one or more targets, e.g., drugs of addition) into a control solution, dissolving reagents into the sample, mixing the control solution, mixing the sample, moving the control solution into one or more test wells in the photonics chip, emitting light through all or some of the first plurality of fibers, detecting evanescent signals from the photonics chips from one or more of the second plurality of fibers, moving the sample into the one or more test wells of the photonics chip, and detecting evanescent signals from the photonics chips from one or more of the second plurality of fibers. In some variations the method may include testing the control solution in the same well as the sample solution. The controller may coordinate any or all of these steps and may repeat any of these steps.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings, of which:

FIG. 4A illustrates a top view of the bottom part of the cartridge attached to the saliva collection device.

FIG. 4B illustrates a perspective view of the bottom part of the cartridge attached to a cross-sectional view of the saliva collection device.

FIG. 4C illustrates a close up view of a piercing element using to puncture a blister pack.

FIGS. 6A and 6B illustrate a perspective view and a cross-sectional view, respectively, of a cap for the saliva collection device.

FIG. 7 illustrates a schematic of the parts of the fluidic circuit in the assembled cartridge.

FIG. 13A shows a control sample containing a detectably labeled binding agent (antibody). FIG. 13B shows a test sample reacted with a detectably labeled binding agent (antibody). FIG. 13C shows antigen attached to a sensing site as it appears prior to passing a control sample, such as the control sample shown in FIG. 13A, across it. FIG. 13D shows antigen on a sensing site and a detectably labeled binding agent (antibody) from a control samples, conjugated to an antigen. FIG. 13E show a sensing site, such as the site shown in FIG. 13D, after flowing a detectably labeled sample across the sensing site.

FIG. 20A shows a partial schematic of an exemplary fluidic circuit for the cartridge (which may include a saliva collection system), similar that shown in FIG. 7. FIG. 20B is a legend illustrating component part of the partial schematic.

FIGS. 20C-20N illustrate one example of method of operating an exemplary cartridge for testing a subject's saliva for one or more drugs.

FIG. 21A is a front perspective view. FIG. 21B is a front view.

FIG. 31 is a top plan view while FIG. 32 is a top perspective view.

FIG. 37 is a side view, while 38 is a slightly enlarged view.

DETAILED DESCRIPTION

Figure 1:
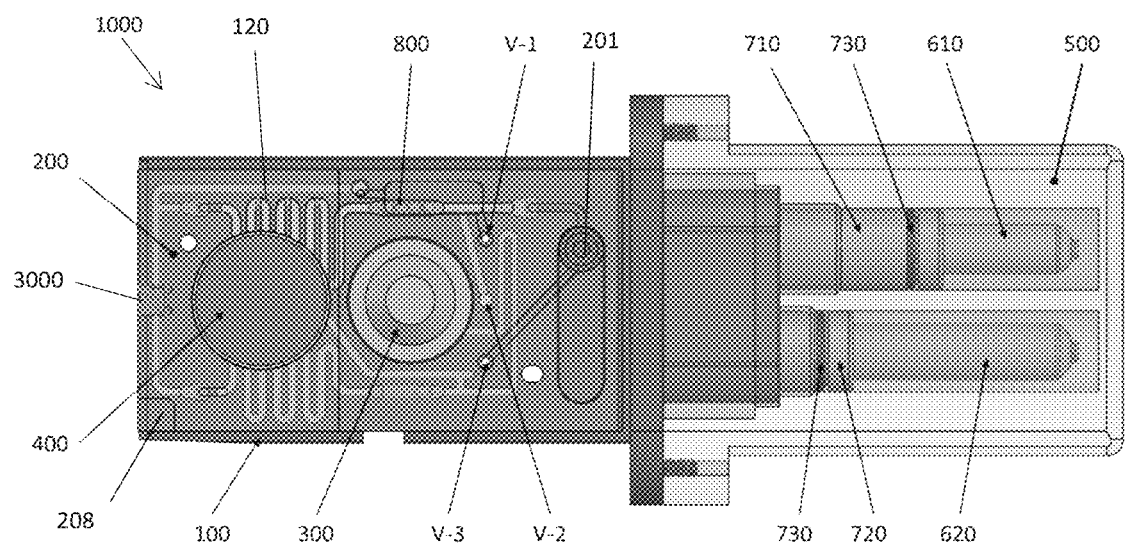
FIG. 1 is a top view of an embodiment of a disposable device that includes an integrated oral fluid collection device and cartridge for processing and testing the collected sample.

In general, described herein are reader apparatuses (device and systems) and methods for reading one or more analyte from a photonics chip of a cartridge. These apparatuses may be configured to receive one or more cartridges that include a photonics chip.

In general, the methods and apparatuses described herein may be used for the detection of an analyte (e.g., drug, biomarker, protein, etc.) from a bodily fluid. The examples provided below are directed primarily to detection of an analyte (or multiple analytes) from a saliva sample, and in particular to the detection of one or more drugs of abuse. However, it should be understood that these methods and apparatuses may apply as well to other bodily fluids and other analytes.

For example, described herein are apparatuses, including optical readers, that may be configured to process a cartridge used for saliva collection so that the saliva sample(s) may be prepared for testing to detect one or more analytes. Processing may include regulating the microfluidics (e.g., combining, mixing, incubating, etc., including in particular, detection. Analytes may be detected by applying a sensing optical wavelength to detect a florescent marker in conjunction with a photonics chip in the cartridge. The reader may control the application of the prepared fluid sample onto the photonics chip, and may read out one or more signal(s) to detect and/or quantify signal.

The optical readers described herein may be used with one or more cartridges that can concurrently collect two samples (one for acute or immediate testing and one for later validation of the acute testing). For example, these cartridges may automatically and accurately process (e.g., dilute) the saliva sample for processing; the optical reader apparatuses described herein may regulate the processing of the fluid sample for detection of one or more analyte. The cartridge may include a cap that is pre-loaded with one or more solution (e.g., a dilution fluid and/or a preservation solution). The cartridge may be configured so that attaching the cap exposes the saliva sample(s) to the appropriate solution, keeping the different samples isolated from each other, and may precisely mix and dispense the saliva sample with the dilution sample in a predictable manner. The cartridge may be configured so that the act of snapping the cap onto the body of the cartridge provide the mechanical energy for dispensing the dilution fluid, mixing it with the saliva sample, and dispensing the diluted and mixed saliva dilution into a diluted sample reservoir ("diluted sample cavity") where it can be further processed.

Any of these cartridges may include one or more fluidic circuits that are configured to processes, in conjunction with a reader, the diluted sample. The cartridge may include, in communication with the fluidic circuit or part of the fluidic circuit, a chip (an optical chip, also referred to as a photonic chip) that includes one or more waveguides along with detection chemistry that may allow detection via evanescent field detection of the presence and/or amount of an analyte. The cartridge may be self-contained, and may include a pump (e.g., a diaphragm, elastomeric membrane, etc.) that may be driven by a driver (e.g., piston, rod, etc.) to push and pull fluid within the microfluidic circuit. The cartridge may also include a plurality of vents (opening) to atmosphere that may be opened/closed by the reader to control fluidic movement (including metering, mixing, sampling, etc.) within the cartridge.

Figure 2:
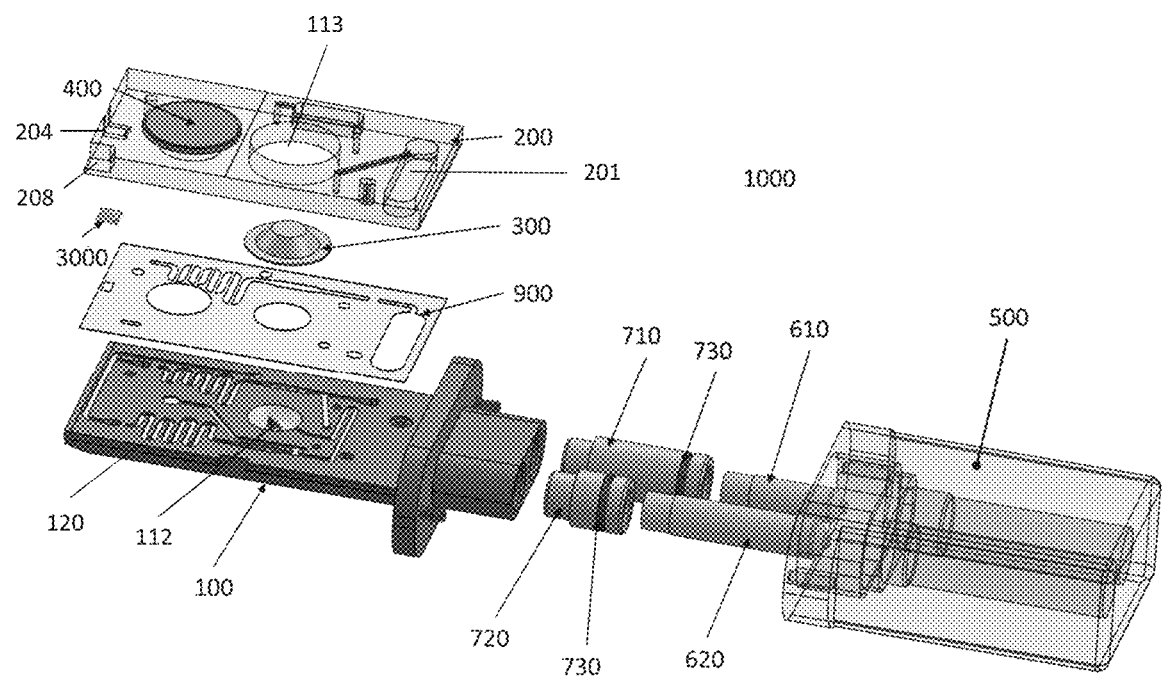
FIG. 2 is an exploded view of the components of the disposable device shown in FIG.
Figure 3A:
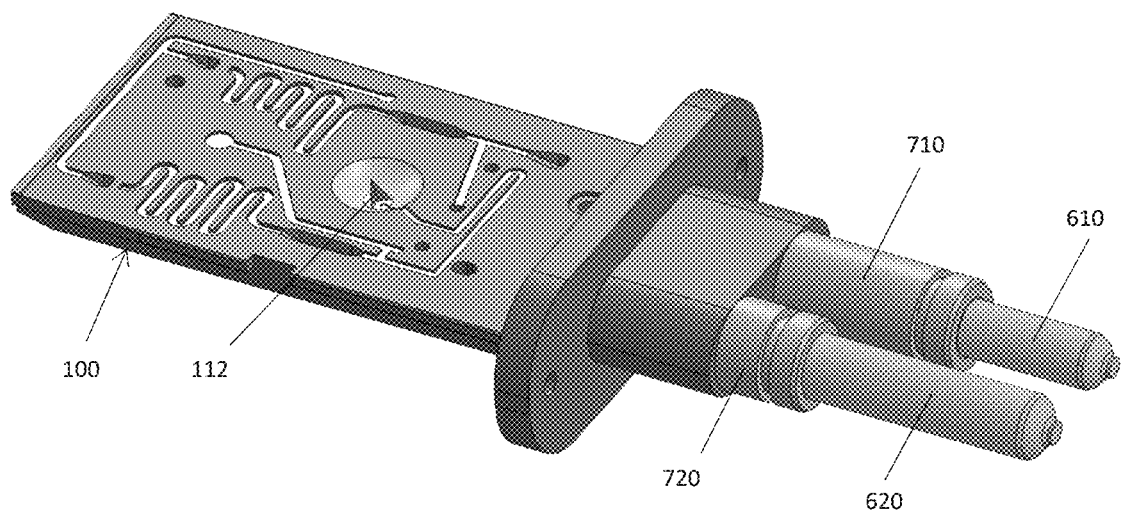
FIGS. 3A and 3B illustrate a top perspective view and bottom perspective view, respectively, of a bottom part of the cartridge attached to the saliva collection device.
Figure 3B:
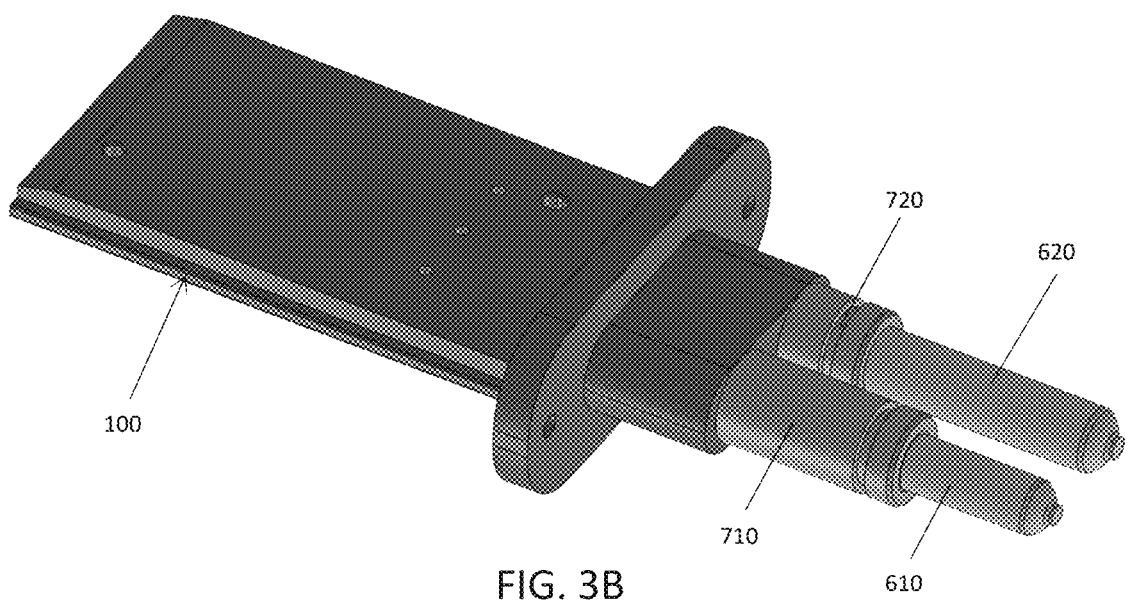

FIGS. 1 and 2 illustrate an embodiment of a disposable device 1000 for collecting, processing, and testing an oral fluid/saliva sample from a subject. After a sample has been collected, the disposable device 1000, which may be a cartridge, can be inserted into a reader for analyzing the sample. FIG. 1 illustrates the disposable device in an assembled state, while FIG. 2 illustrates an exploded view of the disposable device 1000. In one embodiment, the disposable device 1000 is constructed as an assembly of a bottom part (cartridge bottom) 100, a top part (cartridge top) 200 and a channel sealing layer 900. In one preferred embodiment, the sealing layer 900 is a double sided adhesive tape with appropriate cut-outs 902 for fluid conduits/channels that form a fluidic circuit 120. The three parts come together to form a sandwich structure with the sealing layer 900 in between bottom and top parts 100, 200. In one preferred embodiment, the top and bottom parts 100, 200 are held together by the double sided adhesive tape.

The sealing layer 900 can be made from a rubber or plastic sheet and held between the top and bottom part by screws, clips, rivets, bolts, or other fastening mechanisms that can be used to compress the bottom part 100 with the bottom part 200. The tightening force applied by the screws or other fastening mechanism squeezes the rubber or plastic sheet, which functions like a gasket, and provides sealing between fluid channels.

The sealing layer 900 can be made from a rubber sheet and held between the top and bottom part by means of heat staking or mechanical staking between the top and bottom parts. The stakes are designed to provide a mechanical force which squeezes the rubber sheet and provides sealing between fluid channels.

The bottom and top parts 100, 200 may be connected to each other by applying liquid adhesive in a pattern required by the fluid channels. The adhesive can also provide sealing between fluid channels.

In some embodiments, the sealing layer 900 can be a combination of the features described above, such as a rubber or plastic layer with adhesives.

In some embodiments, the cartridge top 200 and cartridge bottom 100 may be hard plastic parts that when assembled form the fluid conduits. The plastic parts may be manufactured by machining or injection molding or vacuum forming or any other appropriate plastic manufacturing techniques.

The cartridge top 200 can have an elastomeric membrane 400 covering a cut-out in the hard plastic part. The elastomeric membrane 400 may be attached, such as by being glued, to the cartridge top 200. The elastomeric membrane 400 may be molded over the hard plastic top 200 by means of over-molding or two-shot injection molding process. The elastomeric membrane 400 and the cavity formed by the cut-out can be in fluid communication with the fluidic channels and can function as a pump that drives fluid through the fluidic channels.

Figure 5A:
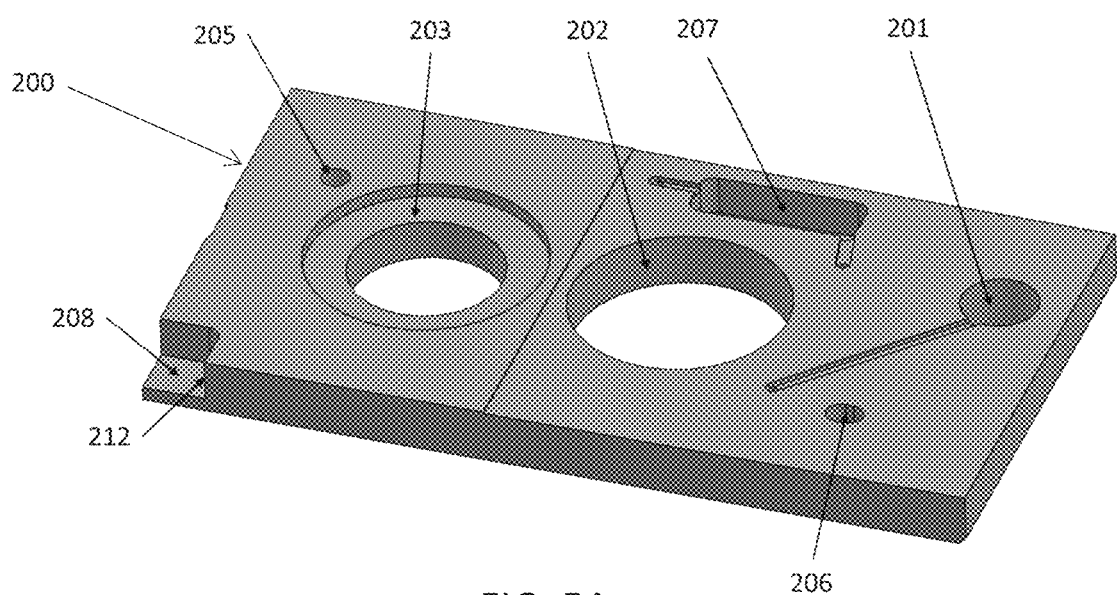
FIGS. 5A and 5B illustrate a top perspective view and a bottom perspective view, respectively, of a top part of the cartridge.
Figure 5B:
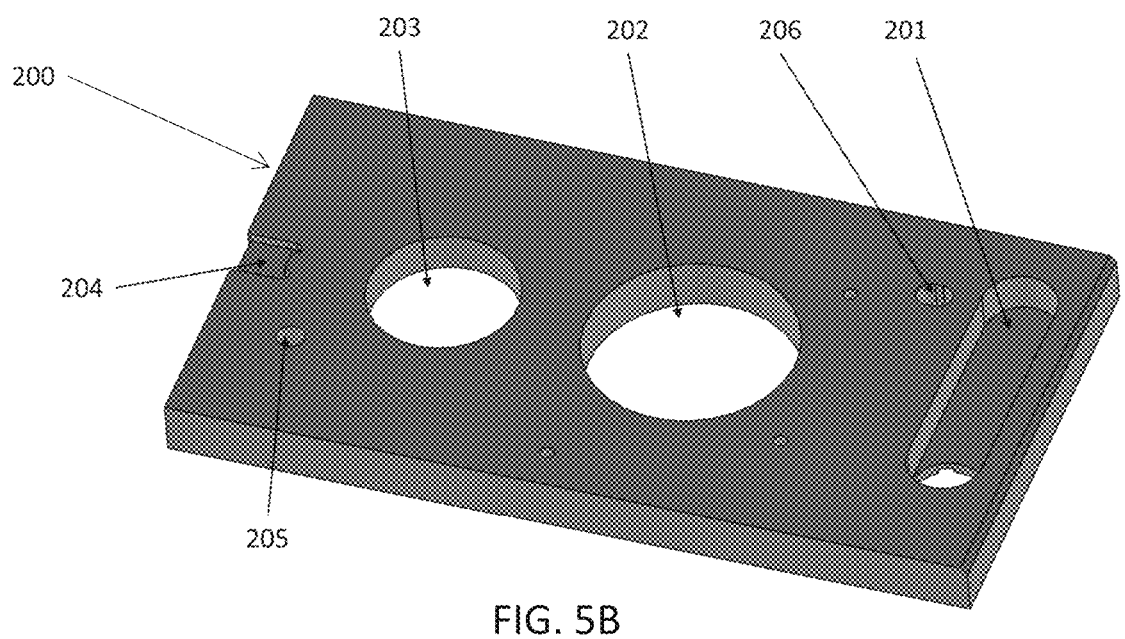
Figure 5C:
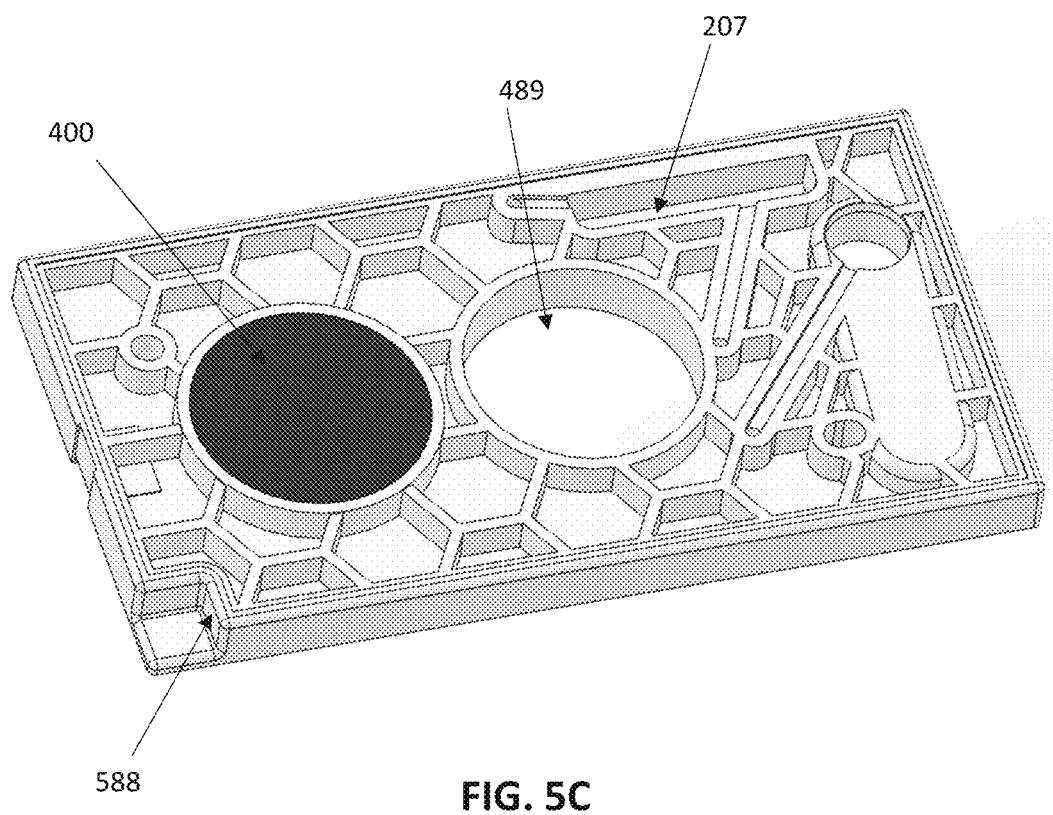
FIGS. 5C and 5D show a top and bottom, respectively, or an example of a cartridge body.
Figure 5D:
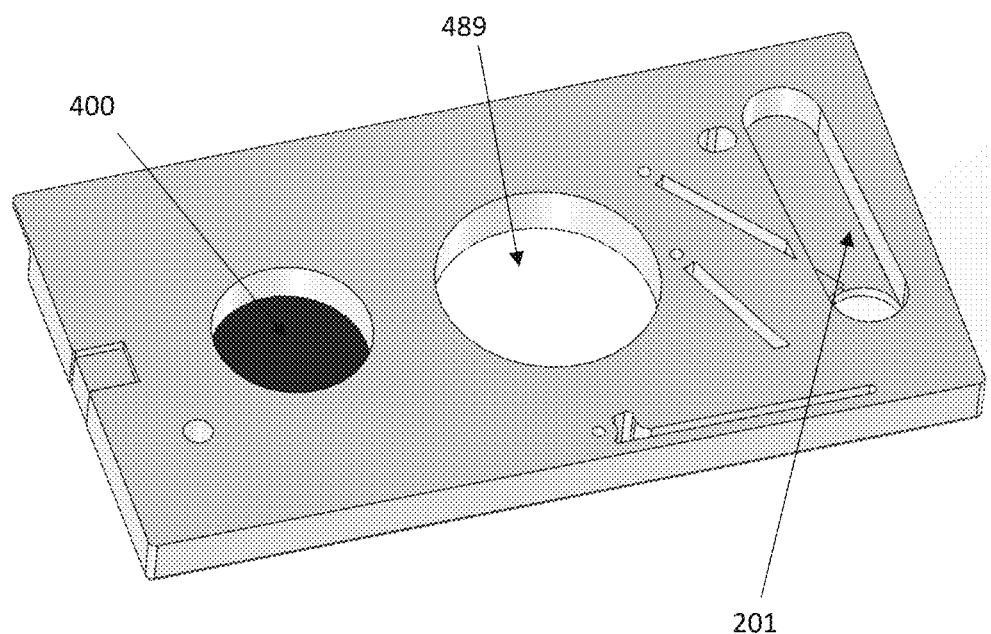

FIG. 5C shows another example of the cartridge top (shown from a bottom view, FIG. 5D shows a top view). In this example, the elastomeric diaphragm 400 (pump) is exposed on one side to allow access by the reader piston (not shown). The cartridge top may also include a waste region 207 (waste well) and may include calibration regions (e.g., z-location region 588). The cartridge top also includes an opening 489 for the blister pack. FIG. 5D also shown a sample inlet (e.g., which may be part of the diluted sample cavity/reservoir 201. The cartridge body may be made of any appropriate material, for example, a clear, transparent, medical grade polycarbonate (PC) and/or (e.g., overmolded with) a medical grade, thermoplastic elastomer (TPE), Shore 40A.

For example, as shown in FIGS. 1, 2, 5A, and 5B, an elastomeric membrane 400 can cover a cavity 203 in the cartridge top 200 to create a pumping well. The elastomeric membrane 400 may be pushed upon by an actuator in a reader for the disposable device 1000. As the membrane 400 is depressed into the cavity 203 it pushes the air out of the cavity 203 and into the fluid channel. The column of air pushed into the fluid channel in turn moves a slug of liquid in the fluid channel.

Reversing the direction of motion of the actuator releases the stretched membrane 400 which, owing to its elastic nature tries to return to its original shape and thus tracking the actuator as it moves. As the membrane 400 moves back to its original shape, it creates a suction in the pumping cavity 203. This suction allows movement of slug of liquid within the fluid channel in a direction opposite to the previous motion. Thus, the action of pushing on the membrane 400 and releasing it in a controlled manner allows bi-directional control over the movement of fluid within the fluid channel. As further described below particularly with respect to FIG. 7, a unique aspect of the disclosed device is the multi-channel management of fluid columns/slugs in the fluidic channels using a single on-board pumping mechanism in combination with vents placed at strategic locations.

Returning to FIGS. 1 and 2, a blister pack 300, can be assembled within the disposable device 1000. The blister pack 300 may contain buffer solution (e.g., control solution) and/or reagents used as part of the testing protocol. The blister pack 300 may be stuck directly to a sealing layer 900 made of double sided adhesive tape. The blister pack 300 may be affixed to the cartridge bottom 100 or sealing layer 900 by means of an additional double sided adhesive tape placed on the blister pack 300. The blister pack may be glued to the cartridge bottom 100 or sealing layer 900 by means of a liquid adhesive.

The blister pack 300 can be installed within the disposable device 1000 such that it is very close to, proximate to, or adjacent to a piercing mechanism 112, which may be an integral part of the disposable device 1000. As shown in FIGS. 2, 4A, and 4B, in one embodiment the piercing mechanism 112 is a sharp pointed feature within the molded cartridge bottom 100. Alternatively, the piercing mechanism 112 may be a sharp needle that is glued onto the cartridge bottom 100. The needle may be made from metal or plastic. The piecing mechanism 112 may be press fit or insert molded into the cartridge bottom 100. The piercing mechanism 112 can be positioned in a depression within the molded cartridge bottom 100 such that the blister pack 300 is positioned above the piercing mechanism 112. The cartridge top 200 may have an opening 113 that provides access to the blister pack 300 and allows an actuator of the reader to push the blister pack 300 into the piercing mechanism and thereby release the contents of the blister pack into the fluid channels.

As shown in FIGS. 1, 2, and 5B, the disposable device 1000 can also include a sensing element 3000 in fluid communication with the fluidic circuit 120. The sensing element 3000 may be a photonic chip which is placed within a cavity 204 in the cartridge top 200. The sensing element 3000 may be held in place by being sandwiched between the cartridge top 200 and cartridge bottom 100 and can be held together by means of an adhesive sealing layer 900, for example.

In one embodiment as shown in FIGS. 1 and 2, the disposable device 1000 has an integrated collection device and cartridge. The cartridge includes primarily the cartridge bottom 100, the cartridge top 200, and the associated components as described herein. The collection device includes primarily a pair of collection swabs 610, 620 and a cap 500 and associated components as further described herein.

Figure 11A:
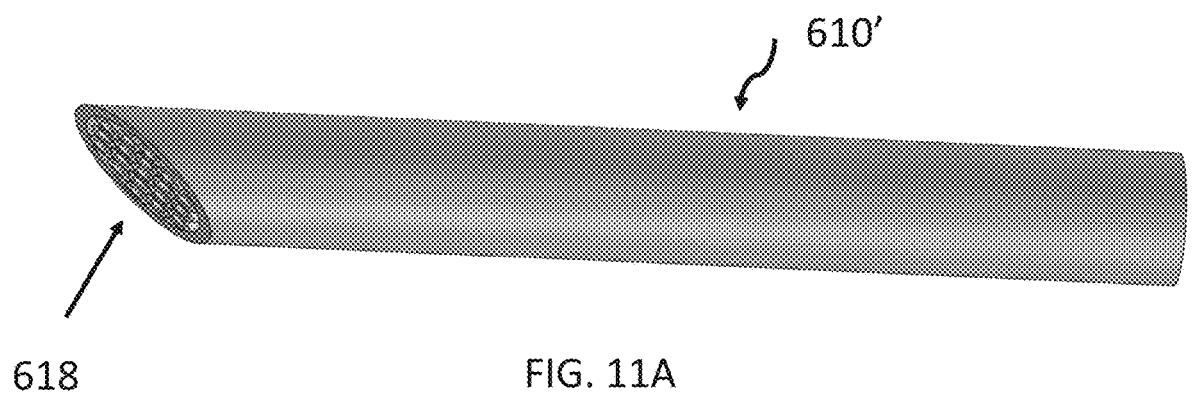
FIGS. 11A, 11B, and 11C illustrate another embodiment of a fluid collection device.
Figure 11B:
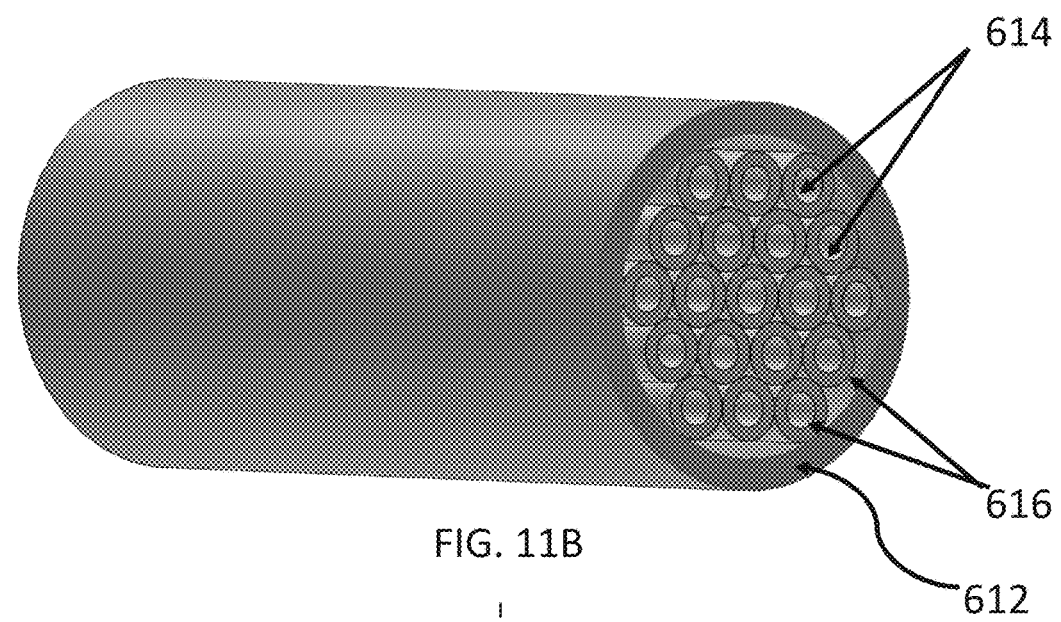
Figure 11C:
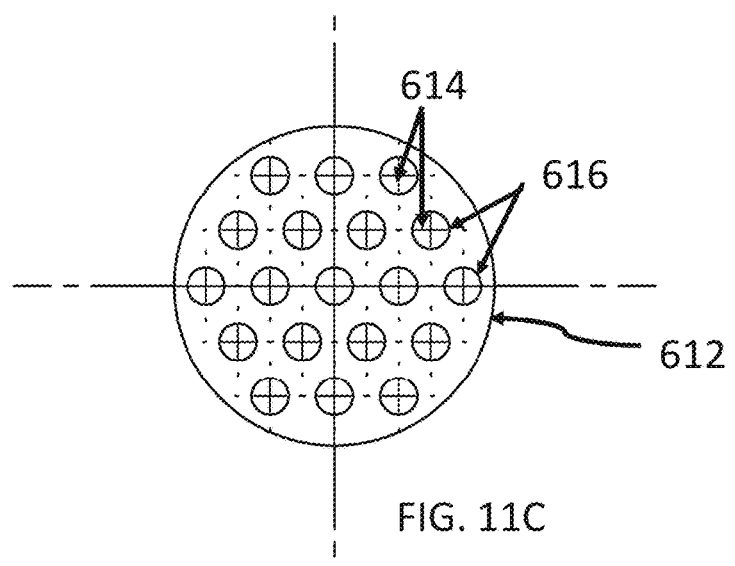

As shown in FIGS. 1, 2, 3A, and 3B, first and second swabs 610, 620 can be held firmly within first and second swab holders (e.g., swab pistons) 710, 720 respectively. The swab holder may alternatively be referred to as swab pistons. The swabs 610, 620 may be held within swab holder 710, 720 by means of press fit. Alternatively, the swabs 610, 620 may also be glued to the swab holders 710, 720. The saliva collection swabs 610, 620 may be made of an absorbent material, such as a sintered porous polymer with an open cell foam structure similar to one used in wicks. Other materials that can be used include polyurethane foam or cellulose fiber. At least one of the saliva collection swabs 610, 620 may have an embedded indicator, such as a colored dye indicator, which changes color upon contact with oral fluids thus indicating completion of the saliva collection. A saliva stimulant configured to stimulate saliva production from a subject may be included on first and/or second collection swabs 610, 620 or otherwise administered to a subject. Since confirmatory testing by the certified lab typically uses traditional testing systems and protocols, a larger amount of saliva may be collected for the confirmatory sample, such as about 2, 3, or 4 times the amount as compared for the rapid test sample. Therefore, in some embodiments, the indicator is included with the confirmatory saliva collection swab 620. In one embodiment the rapid test saliva collection swab 610 is designed to be a hollow shell. The amount of oral fluid collected can be controlled by the size of the collection swabs 610, 620 and the position of the indicator on and/or within the swabs. FIGS. 11A, 11B, and 11C show another embodiment of a collection swab. First collection swabs 610' may have a structure including a plurality of capillary channels 614. (A second collection swab as used herein may have a generally similar structure as a first collection swab with the most common difference a matter of size or dimensions). Upon placing first capillary collection swab 610' in the mouth of the subject (e.g., under the subject's tongue), capillary channels 614 absorb the oral fluid by capillary action and collect only as much as the channel volume allows them.

Figure 4D:
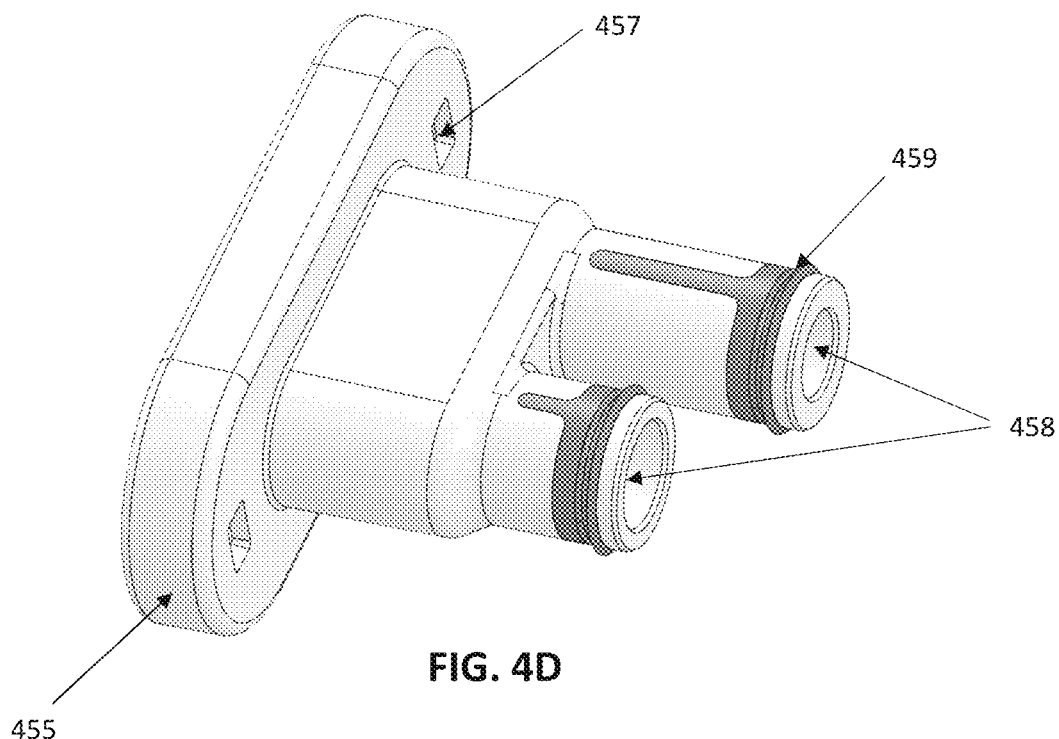
FIGS. 4D and 4E show front perspective and back perspectives, respectively of an example of a distal end of a saliva collection system, showing the collection body and two swab pistons extending distally from the collection.
Figure 4E:
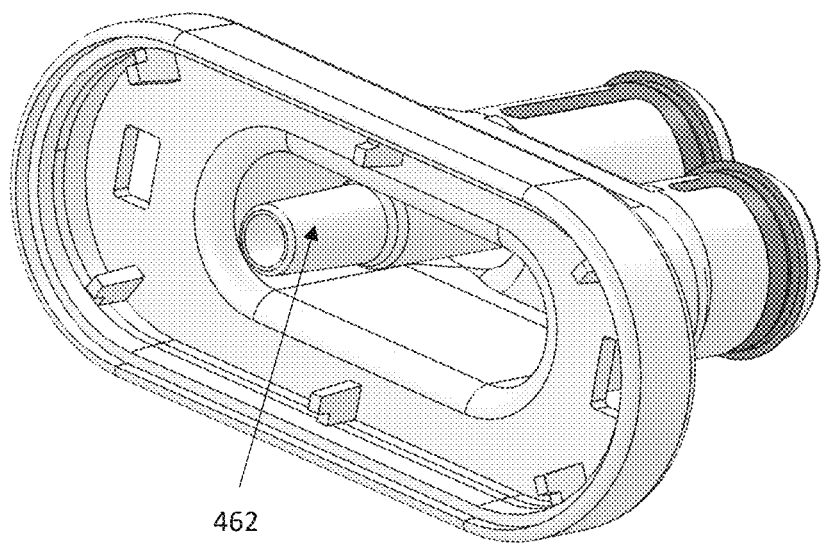

FIGS. 4D and 4E illustrate one example of a collection body 455. The collection body may be flanged outwards and may mate with cartridge (not visible in FIG. 4) body. In some variations the collection body may be the same or integral with the cartridge body. In FIG. 4D the collection body includes a connector 457 (a female portion of a snap fit in this example) for connecting to the cap. A pair of swab pistons 710 extend distally from the collection body. Each swab piston includes an internal channel 458 configured to wick saliva from an open distal end of the first swab piston. For example the channel may hold a porous material and/or capillaries. The swab pistons may each also include a seal (e.g., plunger seal) 459. FIG. 4E shows an internal view of the collection body, showing a connection within the body for fluidic connection to the cartridge portion (e.g., the diluted sample cavity in the cartridge). In this example, the collection body includes a male lure 462 connection for connecting to the cartridge.

The collection body and/or swab pistons may be made of any appropriate material, for example, a clear, transparent, medical grade polycarbonate (PC) and/or (e.g., overmolded with) a medical grade, thermoplastic elastomer (TPE), Shore 40A.

As mentioned, the wicking material within the swab piston, which may be referred to as the swab, may be porous material and/or it may be constructed by putting a number of capillaries 616 together in a bundle with a sheath 612 around them to hold them together or for protection. Such capillaries may be curved or otherwise shaped, but in general will be straight. Alternately a swab may be constructed using a multi-lumen capillary with the requisite number of lumens. The capillaries may be made of glass or plastic material or otherwise manufactured or treated to minimize binding of substances of interest to prevent their loss prior to assay. A swab may be relatively rigid or may be flexible to aid in placement. A swab may have a flat end(s) or may have one or more shaped end 618 as shown in FIG. 11A which may allow easy access to saliva for capillary suction upon placing the swab in the mouth (e.g., under the tongue). An entire swab or swab holder may be shaped to aid in collection and/or handling. Such a shaped end or shaped swab may be flattened, rounded, tapered or so on. Although the capillaries or channel may all be the same length, in some examples, some capillaries or some channels may be shorter than others. For example, capillaries on one side of a taper may be shorter than capillaries on the other side of the taper. Likewise, a swab with a single channel in a hollow shell or a porous material may have different dimensions on different parts, and one longitudinal part of a channel, shell or single material swab may be longer than another part (e.g., 1%-50% longer). FIG. 11C shows a cross section through a swab showing one example of placement of capillaries.

Figure 12A:
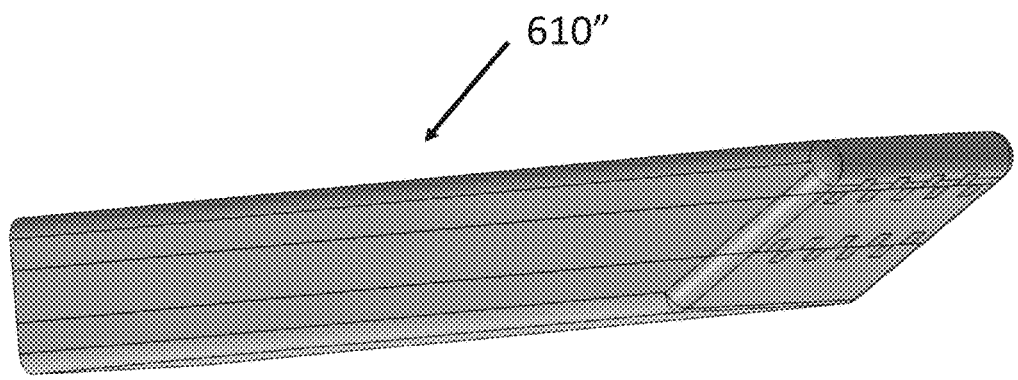
FIG. 12A illustrates another embodiment of a fluid collection device.
Figure 12B:
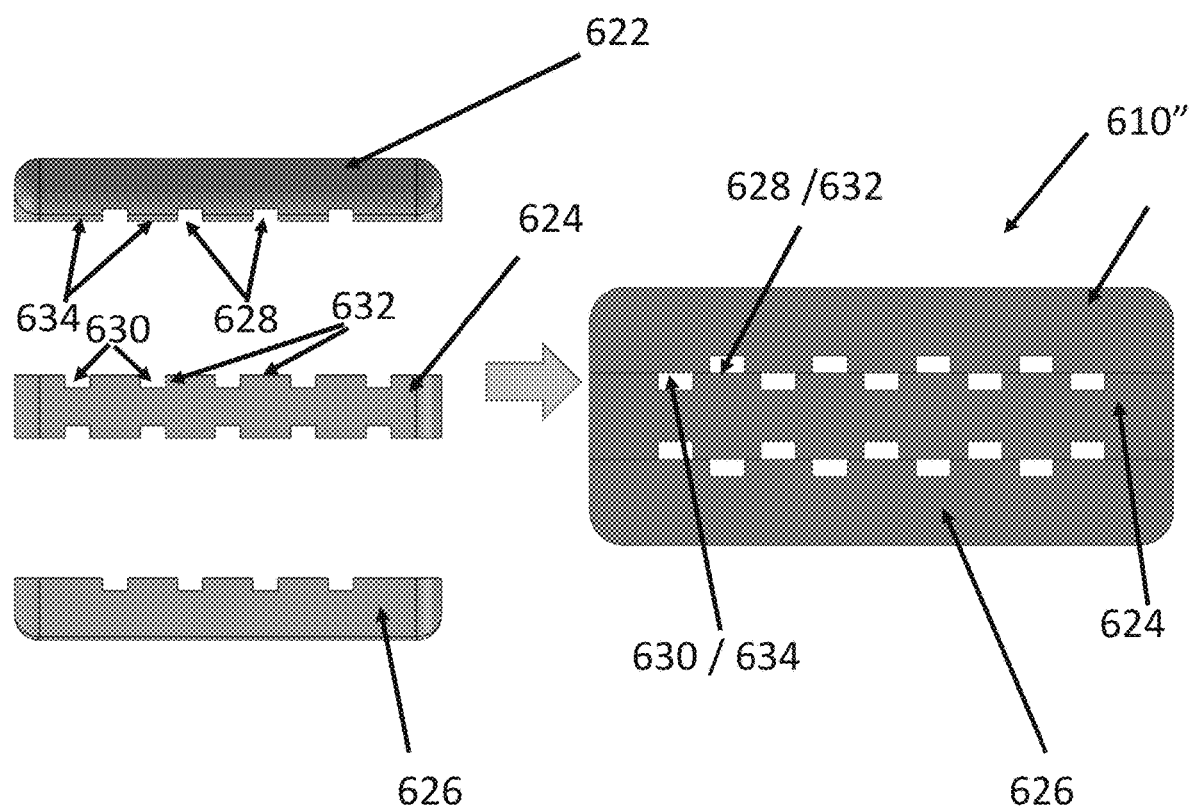
FIG. 12B illustrates an example of how a fluid collection device such as the one shown in FIG. 12A can be manufactured.

FIGS. 12A and 12B illustrate swab 610" with a plurality of channels configured to collect a bodily fluid. FIG. 12A shows a perspective view and FIG. 12B shows a front view of the three sections of a swab before and after joining the sections. A swab may be made in a sandwich construction whereby two or more halves or parts of a swab come together to create capillary channels. Each half or part may be made of a material with channels cut out as shown in FIG. 12B. In some embodiments, an opening (channel) is cut out of one half or part, and the floor or roof of the channel is supplied by another half of part of the swab. In FIG. 12B, top section 622 of swab 610' houses top channels 628 while middle section 624 of swab 610' provides floors 632 for top channels 628 when the top section 622 and middle section 624 of the swab are adjoined. Top 622 of swab 610' also provides roof 634 for middle channels 630 provided by middle section 624. Similarly, middle section 624 and bottom section 626 also form channels. In some embodiments, a cut out channel is half a channel and two half channels come together to create a complete capillary channel(s) (as could be seen if top section 622 and middle section 624 were offset from one another. Channels may be any shape that collects or transports the body fluid, such as circular, rectangular, rounded rectangles and so on. Halves or parts may be plastic and the plastic parts may be manufactured by machining or injection molding or vacuum forming or any other appropriate plastic manufacturing techniques. The plastic parts may be joined together by pressure sensitive adhesive or liquid adhesive or by ultrasonic welding or any other plastic joining techniques known in the art.

A swab may have at least 2, at least 3, at least 4, at least 5, at least 10, at least 15, at least 20, or at least 30 channels. In some preferred embodiments, a swab may have between 14 and 22 channels, such as about 18 capillary channels. Capillary channel(s) of a swab may have a length between 1 mm and 10 cm and in general will have length between 5 mm and 50 mm (5 cm). In some embodiments, a capillary, a capillary channel, a hollow shell or a porous material has a length of from 5 mm to 40 mm, such as approximately 25 mm (from 10 mm to 25 mm). Each capillary channel or lumen may have a diameter between 0.05 mm and 5 mm, such as between 0.1 mm and 1.5 mm (e.g., between 0.3 mm and 0.8 mm.) In general, a length of capillary selected is less than the capillary head for the selected diameter. That is, for a selected capillary channel diameter, the length of oral fluid pulled into the channel due to capillary action against gravity is greater than the selected length of the capillary channel to ensure consistent collection volume.

Saliva Collection

In some examples, a pair of saliva samples are collected simultaneously by placing the saliva collection swabs 610, 620 in the mouth of the test subject. The saliva collection swabs 610, 620 may be sized, shaped, and designed ergonomically to be placed under the tongue on either side of the tongue. This may enhance the salivation of the test subject and allow for improved collection efficiency. In some examples, a saliva collection swab may be configured for increasing saliva production, such as allowing or encouraging biting or chewing or may contain a component configured to increase saliva production such as a chemical or odorant. In some examples, components for increasing saliva production may be separate from a collection device, such as a separate vial containing an odorant, etc. In some examples, a single saliva sample may be collected such as a single sample in which part of the sample is used for rapid test analysis and another part used for confirmatory testing. In some examples, two or more saliva samples may be separately collected (e.g., using two or more separate collection devices).

One of the saliva collection swabs 610 is used for the rapid test performed within the cartridge portion of the disposable device 1000, while the saliva sample collected by the other swab 620 may be used for testing by a certified forensic lab for confirmatory testing and/or can also be used for storage as forensic evidence.

Once the saliva/oral fluid is successfully collected by the saliva collection swabs 610, 620, the user applies the collection device cap 500 over the oral fluid collection end, i.e. the saliva collection swabs 610, 620, of the disposable device 1000.

As shown in FIGS. 6A and 6B, the collection device cap 500 has two cavities 501, 502 to receive the saliva collection swabs 610, 620. In some embodiments, the disposable device can have more than 2 collection swabs, such as 3, 4, or 5 swabs, and the device cap 500 can have a matching number of cavities. The rapid test cavity 501 is filled with a known amount of dilution buffer solution used for dilution of the rapid test saliva sample collected by swab 610. The dilution buffer solution may be constituted of 5% bovine serum albumin (BSA) in phosphate buffered saline (PBS), for example. Other concentrations of BSA or other protein can be used, such as between 2-10%. In addition, other proteins may be used in the dilution buffer solution, such as non-fat dry milk, and other buffers can be used, such as tris-buffered saline (TBS). The confirmatory test cavity 502 is filled with a preservation solution used to preserve the confirmatory sample collected by swab 620 so that the confirmatory sample can be sent to a certified lab for confirmatory testing. The preservation solution may include a buffer.

The two cavities 501, 502 filled with dilution and preservation fluids respectively may be sealed by means of a foil cover 510 or other removable or pierceable sealing mechanism, such as a lid or cap. The primary purpose of the foil cover 510 is to contain the dilution and preservation fluids within the collection device cap 500. The foil cover 510 is designed to have very low vapor permeability to prevent or greatly reduce any ingress of water vapor and any evaporation of the fluids within the cavities 501, 502. The foil cover may be a heat sealable foil with a typical multi-laminate construction of a layer of aluminum foil for reduced vapor permeability, and a polymer layer (for example polypropylene) for heat seal ability.

Upon connecting the collection device cap 500 with the cartridge of the disposable device 1000, the collection swabs 610, 620 pierce through the foil seal 510 within the cap 500 and move into the cavities 501, 502. The action of closing the collection device cap 500 generally x initiates the sequence for dilution of the saliva sample for rapid testing.

Figure 6C:
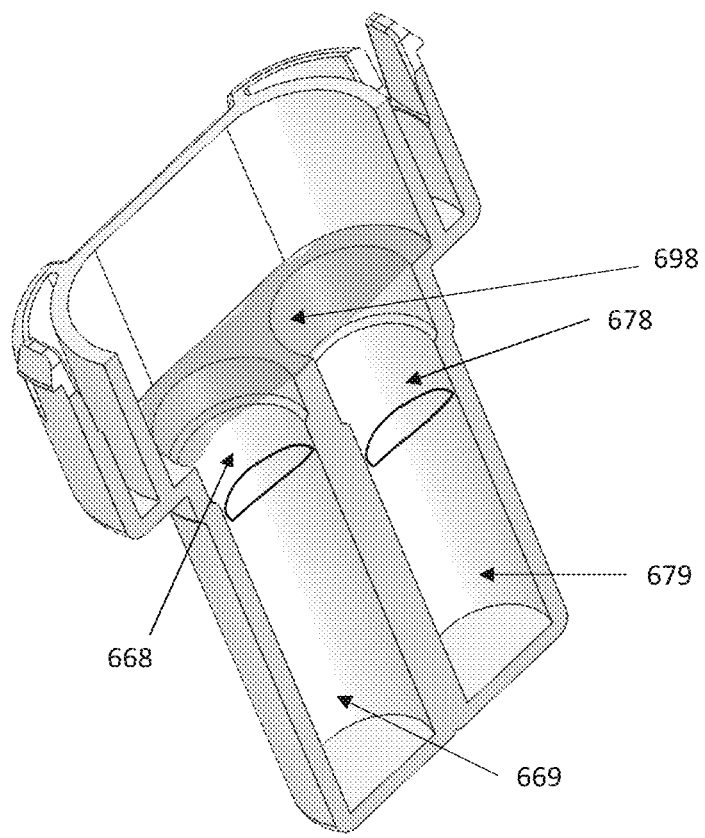
FIG. 6C shows a section through a top of an example of a saliva collection system (with the front side removed).
Figure 6D:
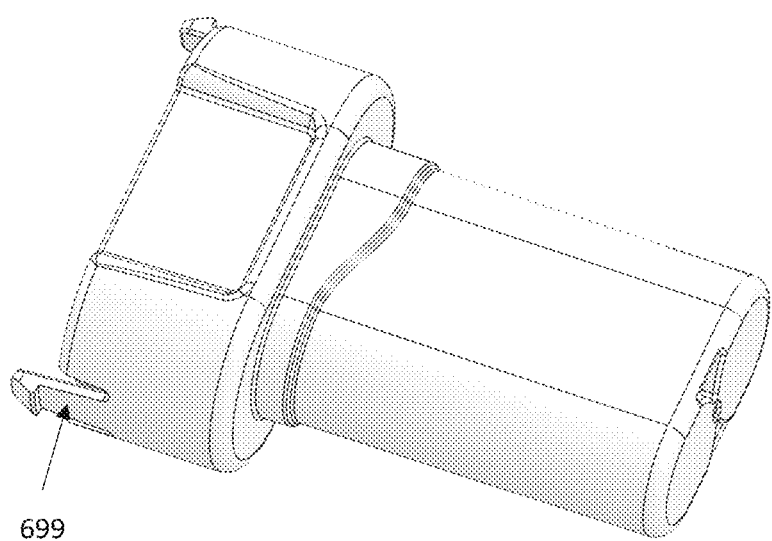
FIG. 6D shows a perspective view of the exemplary saliva collection system top of FIG. 6C.

FIGS. 6C-6D show additional examples of a cap. FIG. 6C shows a section view (bisecting the cap in the long axis) shown in the inside of the cap. In this example, the frangible cover (shown as a foil seal 698) enclosed the fluid held within the tubes of the cap. For example, the first tube 678 includes a dilution buffer (rapid test buffer) 679, while the second tube 668 includes a preservation solution (lab test buffer) 669. FIG. 6D shows an external view of this variation of a cap, showing connector (e.g., a male snap-fit connector 699) that may click and lock onto the collection body, as described. In some variations the connector is configured to snap on with a force sufficient to drive fluid from the tubes in the top, through the swab piston, mixing, and dispensing into the diluted sample cavity.

As shown in FIGS. 1 and 2, the swab holder 710 is sized, shaped, and designed to act as a plunger within the cavity 501 of the collection device cap 500. The O-ring 730 fitted onto the swab holder 710 provides a fluid seal between the swab holder 710 and cavity 501 during the plunging action, which ensures that the displaced dilution buffer solution is forced through the collection swab 610 to mix with the collected saliva sample.

The O-ring may be an over-molded elastomeric lip type feature to provide the sealing function. The elastomer can be silicone, thermoplastic elastomer (TPE) or any other elastomeric material that does not cause any contamination of saliva/oral fluid sample by means of chemical reaction or leaching chemicals or absorption of analyte.

As shown in FIGS. 1, 2, 4B, 5A, and 5B, the swab holder 710 has a fluid pathway 111 connecting the back end of the porous saliva collection swab 610 to a diluted sample cavity 201 within the cartridge. The diluted sample cavity 201 holds the diluted sample within the cartridge for further use in the rapid test.

As the cap 500 is closed, the swab holder 710 performs a plunging action. The plunging action pushes upon the dilution buffer fluid within the cavity 501. As the cavity is sealed by the O-ring 730, the dilution buffer within the cavity 501 is forced through the porous saliva collection swab 610 and into the diluted sample cavity 201 within the cartridge through the fluid pathway 111. As the dilution buffer moves through the saliva collection swab 610, it mixes with the saliva sample contained within the porous swab 610.

A dilution factor can be defined as:

$$\text{Dilution Factor (DF)} = (\text{Plunged Volume})/(\text{Volume of Saliva})$$

The volume of saliva collected depends on the porosity or open space of the saliva swab material and the solid volume of the saliva swab 610, and if used, the location of the fluid indicator on the swab. In general, for a given shape, size and material the maximum or desired volume of saliva collected by the swab 610 is generally fixed. For example, the volume of saliva collected depends on the overall dimensions. For example, the capillary volume within saliva swab 610 is: Capillary Volume=No. of Capillaries×Length of Capillary× Cross-section Area of Capillary. The volume of saliva obtained by a swab may be between $3.0 \times 10^{-5}$ mls to 3 mls. In some particular examples, the volume of saliva obtained by a swab is between 0.01 mls and 1.0 ml (e.g., between 0.1 mls and 1.0 mls).

The amount of fluid pushed through the swab is equal to the volume plunged by the swab holder 710. The dilution factor therefore is dependent only on geometry and material selected. Thus the device disclosed can achieve a very consistent dilution factor. Any variability in the dilution factor is directly controlled by the manufacturing tolerances of the swab 610, and the swab holder 710. The dilution factor may also be measured and calculated by including a known quantity or concentration of a substance in the dilution buffer which is then combined with the saliva sample and tested along with the analyte of interest. The dilution factor can be equal to the known concentration of the substance in the dilution buffer divided by tested concentration of the substance after combination with the saliva sample.

The diluted sample pushed through the swab 610 is collected in the diluted sample cavity 201 within the cartridge. The cavity 201 can be provided with a capillary stop valve 101 to prevent the sample from moving into the fluidic circuit by capillary action.

The collection device cap 500 may then be connected to the cartridge by mechanical means. The mechanical connecting means may be a snap fit mechanism to hold the cap in place. Additionally, the mechanical connection can be a single use snap fit that can be designed in a manner such that it cannot be opened without permanently damaging the snap fit mechanism thus preventing any possibility of tampering.

Figure 10:
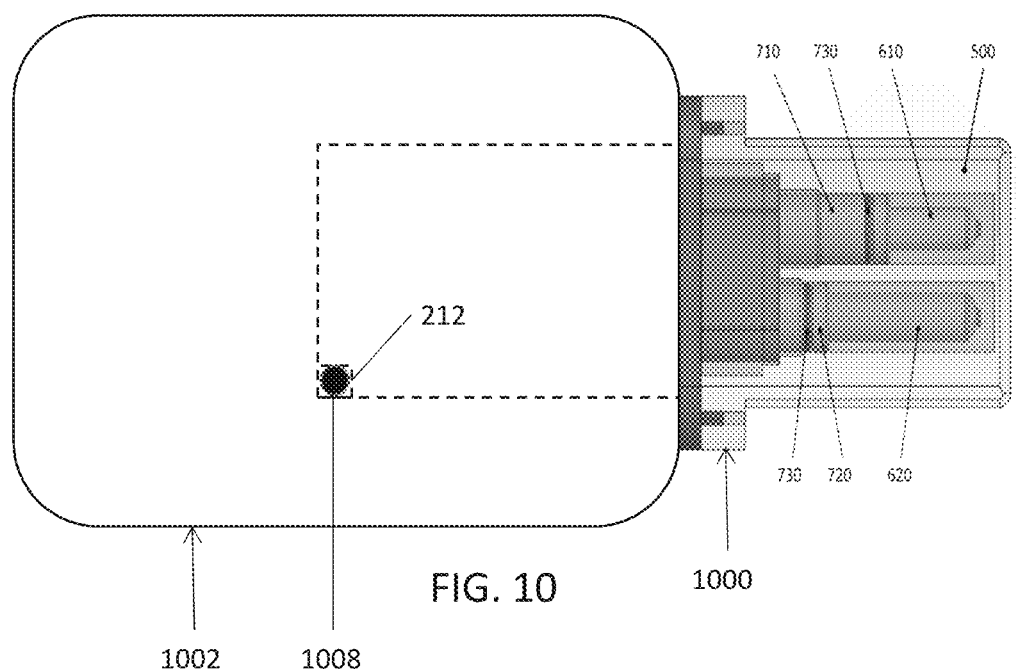
FIG. 10 illustrates the insertion of the cartridge into a reader for testing.

Once the cap 500 is placed firmly, the disposable device 1000 may be inserted into a reader 1002 for automated testing as shown in FIG. 10.

The reader module 1002 receives the disposable device 1000 and clamps it in place. As the detection system is an optical sensing system, the disposable device 1000 needs to be accurately located within the cartridge and/or accurately aligned with the optical sensing mechanism in the reader 1002. For this purpose, the disposable device 1000 has two features that ensure accurate alignment of the device within the reader module.

Figure 9A:
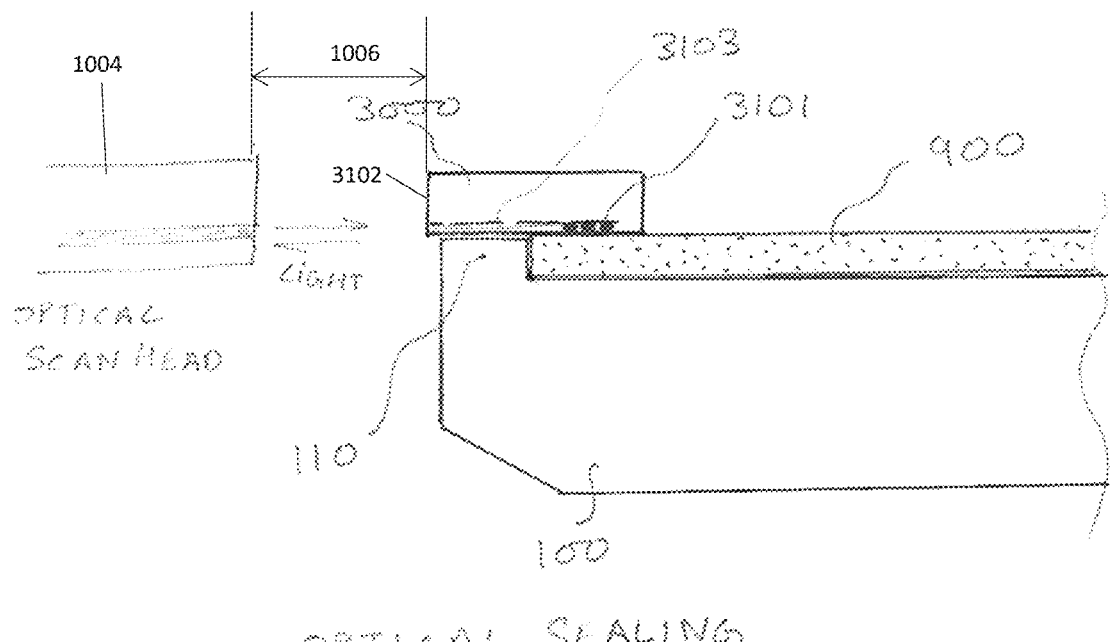
FIG. 9A illustrates a side cross-sectional view of a portion of the cartridge and optical chip in alignment with an optical scan head of a reader device.

Any of the apparatuses (e.g., readers) described herein may include a z-alignment feature. With the disposable device 1000 clamped within the reader module, as shown in FIG. 9A, the front face 3102 of the photonic chip may be excited by an optical element within the reader. The optical element within the reader may also sense the photonic information emitted from the photonic chip.

A Z-gap 1006 can be defined as the distance between the front face 3102 of the photonic chip 3000 and the sensing element 1004 within the reader module. This Z-gap is helpful for accurate excitation and sensing of the photonic chip 3000 as the intensity of light transferred between the chip and the sensing element may vary with the square of the Z-gap.

As shown in FIGS. 1, 2, 5A, 5B, and 10, upon insertion of the disposable device 1000 within a reader 1002, the face 212 of the cut-out feature 208 butts against a dowel pin 1008 present in the reader 1002. The face 3102 then becomes a reference face for location of all fluidic features and the chip cavity 204 that holds the photonic chip 3000.

With a pre-designed reference face 212 engaging with a pin 1008 in the reader module 1002, the Z-gap 1006 can be accurately controlled and any cartridge-to-cartridge variation of the Z-gap 1006 can be kept within a controlled narrow band.

Z-gap variability may dependent on the tolerance stack-up of features within the disposable device 1000 and may be controlled by the manufacturing process.

Figures 8A, 8B:
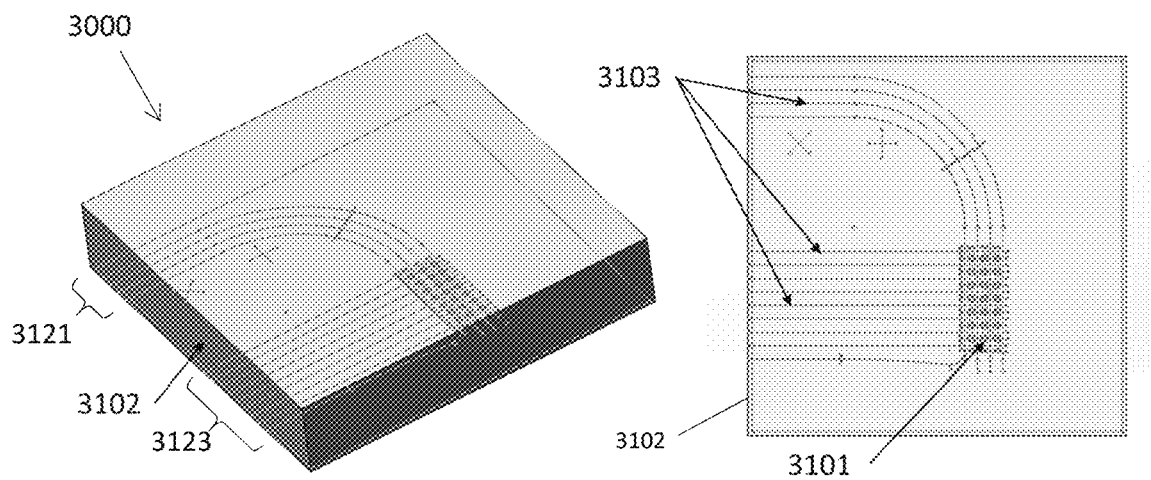
FIGS. 8A and 8B illustrate an embodiment of an optical chip for analyte testing.
Figure 13A:
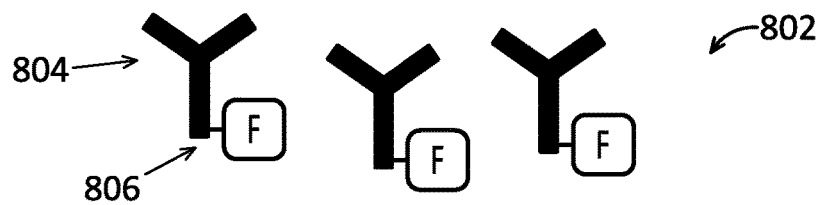
FIGS. 13A, 13B, 13C, 13D, and 13E show an example of an assay useful for detecting an analyte, such as an analyte from a bodily fluid.
Figure 13B:
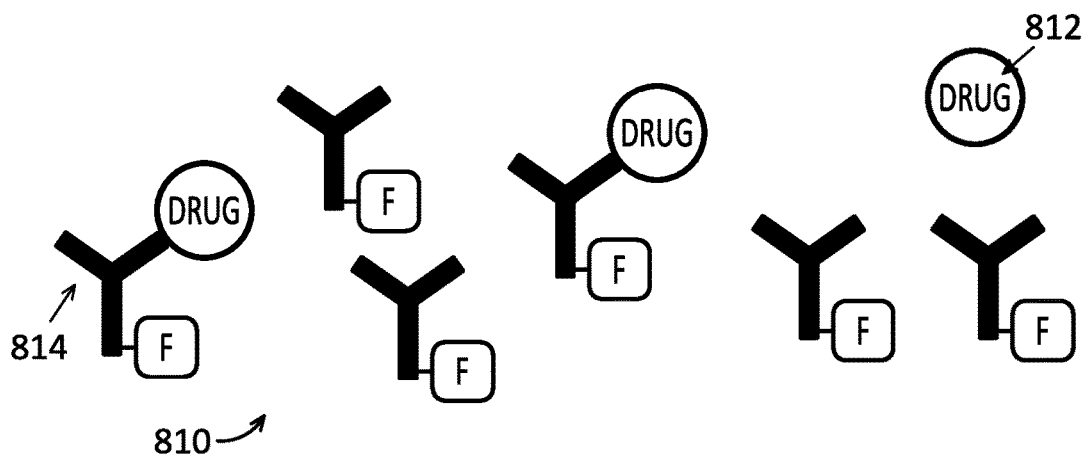
Figure 13C:
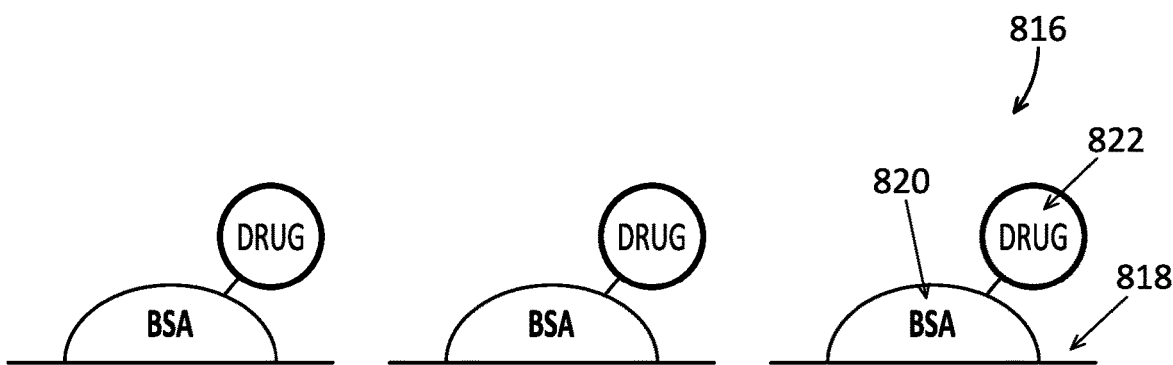
Figure 13D:
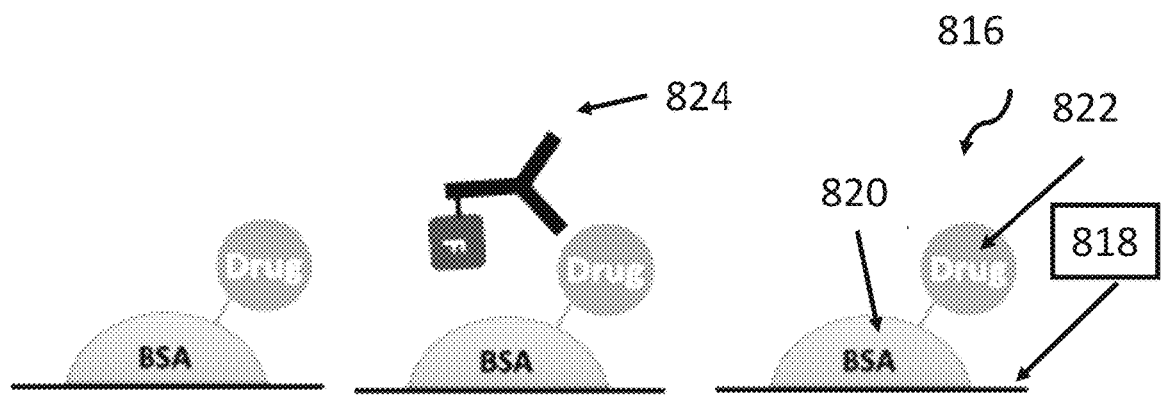
Figure 13E:
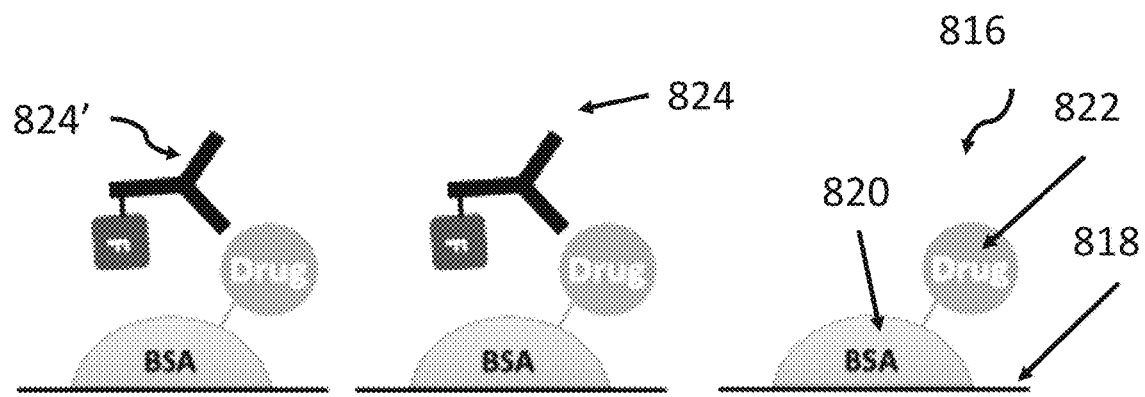
Figure 14A:
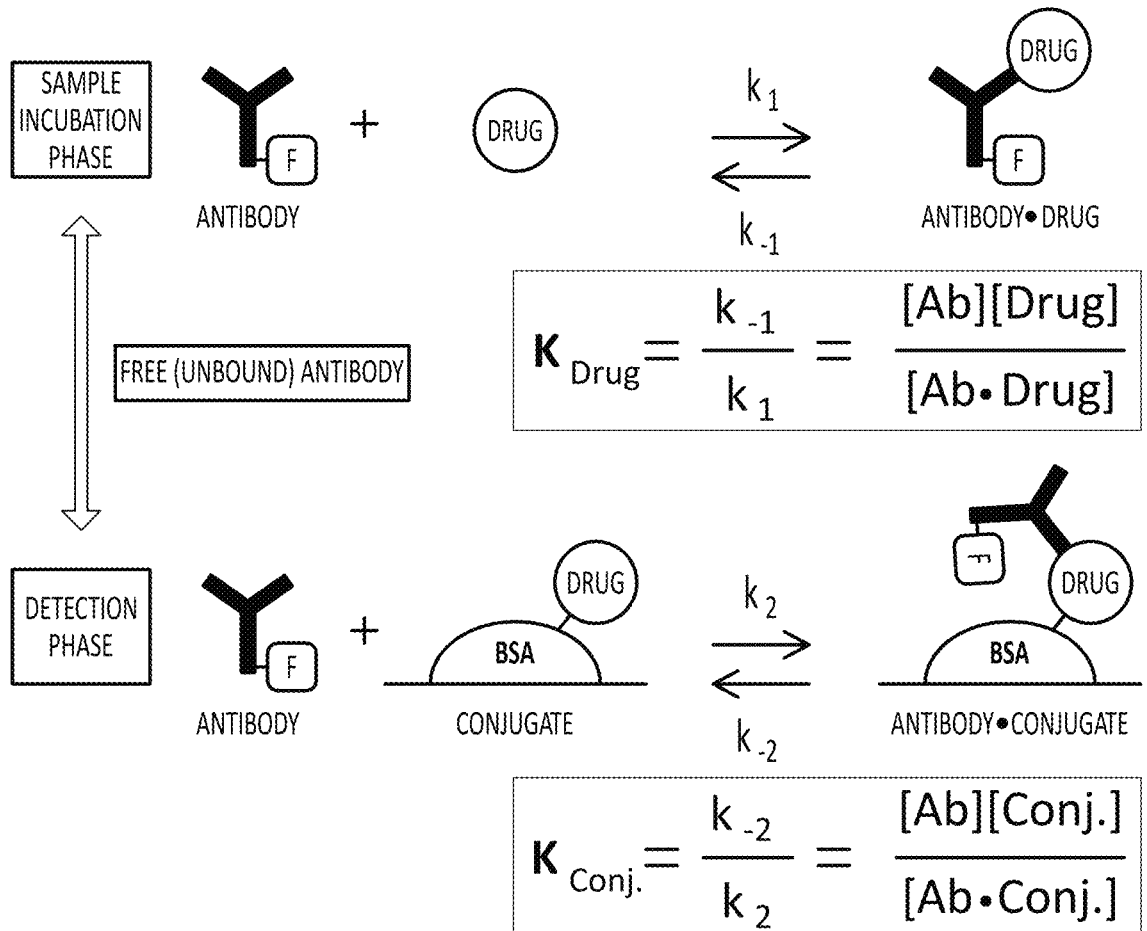
FIG. 14A illustrates kinetics of analyte and antibody binding over time.
Figure 14B:
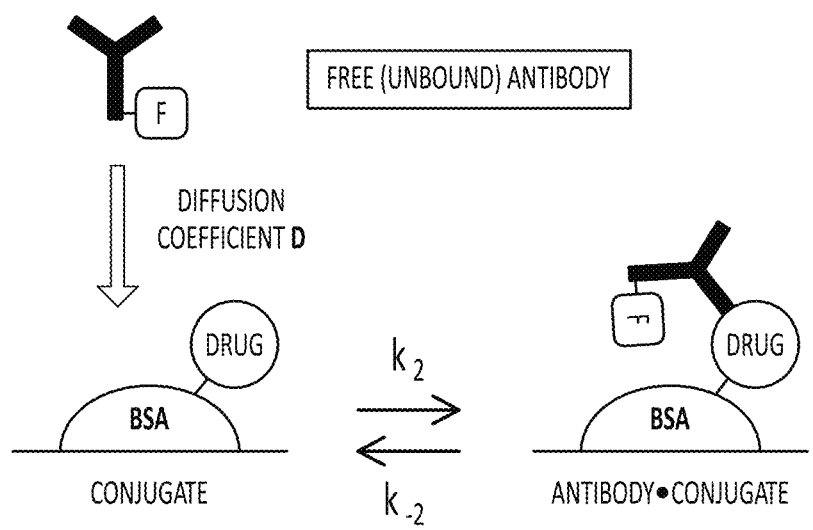
FIG. 14B shows the kinetics over time of free, unbound antibody binding to antigen, such as antigen attached to a sensing well.

Any of the apparatuses described herein may include an optical sealing feature. As shown in FIGS. 8A, 8B, and 9 (showing examples of photonic chips that may be used in a cartridge as described herein), the sensing method may involve a laser illumination of the photonic chip 3000 by means of an optical scan head 1004 within the reader. The scan head 1004 shines a laser which is received by an optical waveguide 3103 within the chip 3000. In FIG. 8A, there are four excitation-receiving waveguides 3121 that intersect with eight detection (or emission) waveguides 3123 (an additional loopback waveguide is also included); a well is located at each intersection. The light irradiates the sensing wells 3101 within the chip 3000. These wells have coated reagents, such as antigens of the analytes being tested, which bind with the binding agents (fluorophore conjugated antibodies) added to the sample. The analyte/sensing wells (also called sensing sites) can be pre-conditioned with antigens. An antigen can be bound to a sensing well using any type of tether, such as BSA, another antibody, etc. In some embodiments, the amount of bound antigen in the sensing well 3101 is much greater, such as on the order of at least 10, 100, or 1000 times (e.g. mole per mole) the amount of fluorophore conjugated antibody that is added to the control sample and optionally also the saliva sample. This ensures that the antibodies from the control sample only uses up a very small fraction of the antigen, which can essentially or approximately considered to be an infinite amount relative to the amount of antibody, which means that there is sufficient amount of free antigen to process the saliva sample without washing the sensing wells 3101 to remove the antibody bound to the antigen. The saliva sample may generate a higher fluorescent intensity due to control antibodies left in the well, but this offset can be accounted for, subtracted out, or ignored by measuring the slope of the fluorescent intensity as a function of time. FIG. 13D shows sensing wells 818 with attached antigen 822, for example a drug attached to a sensing well via tether 820 such as a BSA (bovine serum albumin) attachment molecule. Detectably labeled antibody from the control sample has attached to antigen (see the far right of FIG. 13D). Upon the addition of a reacted sample (e.g., a diluted bodily fluid sample incubated with a detectably labeled antibody), unbound antibody will bind to available antigen (see the far left of FIG. 13E) and increase in signal intensity of the sample can be measured over time. As indicated above, FIG. 14B shows the kinetics over time of free, unbound antibody binding to antigen, such as antigen attached to a sensing well. The slope is determined by the diffusion coefficient of the unbound antibody in contacting and binding to the antigen (drug) bound to the well. The top part of FIG. 14A shows the equilibrium between analyte found in a sample binding to antibody (thus preventing such antibody from binding to antigen in a sensing well). The bottom part of FIG. 14A shows the equilibrium between detectably labeled antibody and antigen in a sensing well.

The sample metering well 102 may include lyophilized beads having antibodies conjugated with fluorophores that absorb the incoming laser light and then re-emit at a known wavelength. The re-emitted light from the fluorophores is recoupled into another set of waveguides 3103 which direct the light from the fluorophores back to the front face 3102 of the chip 3000. The re-emitted light by the fluorophores received within the waveguides 3103 is measured by the optical scan head 1004 and is the true measure within the system.

This re-emitted light from the fluorophores can also couple optically to the fluid (sample or control) in contact with the photonic chip 3000. Such light can then be dispersed into the medium and reach the front face 3102 of the cartridge and can also be picked up by the scan head 1004 along with the light within the sensing waveguides 3103 of the chip. This light may become a major source of error in measurement if not dealt with.

Two key pathways of this 'optical leakage' were identified: (1) the transmission of light through the material of the cartridge bottom 100, and (2) the transmission of light through the double sided adhesive tape 900. To address the optical leakage, the cartridge bottom 100 is made from an opaque material (preferably black polycarbonate).

Figure 9B:
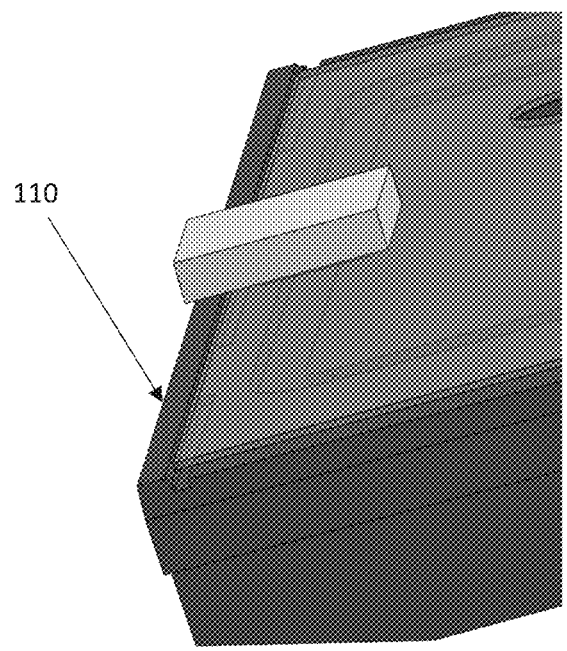
FIG. 9B is another view of an end face of a cartridge showing a ledge or lip region protecting the optical chip.

As shown in FIG. 9A, to block the optical leakage through the double sided adhesive 900, a ledge feature 110 or lip may be provided at the front end of the cartridge bottom 100. The double sided adhesive 900 is placed behind the ledge 110 such that the ledge 110 is between the double sided adhesive 900 and the optical scan head 1004. The height of the ledge 110 is designed such that the double sided adhesive 900 is completely recessed post compression within the sandwich structure of the assembled disposable device 1000. FIG. 9B illustrates another view of a distal end region of a cartridge portion that may integrated with a saliva collection system, the end including a ledge or lip region 110.

Thus the front edge of the cartridge bottom 1000 becomes entirely opaque and provides proper optical sealing and may eliminates a major source of error in measurements.

FIG. 7 is a schematic that illustrates how fluid is transported through the fluid channels in the cartridge using a pump 400 and a series of strategically placed vents V1, V2, and V3 and capillary stops 101, 104, and 108. Vent V1 is positioned downstream of the waste well 207. Vent V2 is positioned upstream the sample metering well 102 and downstream the diluted sample cavity 201, i.e. between the sample well 102 and the diluted sample cavity 201. Vent V3 vents and leads to the diluted sample cavity 201. A first capillary stop 101 is located just downstream the diluted sample cavity 201. A second capillary stop 104 is located downstream of the mixer 103 for the sample metering well 102 and upstream of the chip 3000. A third capillary stop 108 is located downstream the mixer 107 for the control metering well 106 and upstream the chip 3000. The diluted sample is received in a chamber (diluted sample cavity) 201 and is retained within the chamber by means of a capillary stop 101. The capillary stops prevent the fluid from advancing through the fluid channels by capillary action. Advancing past the capillary stops generally requires application of the pump. The disposable device has three vent holes V1, V2, and V3. Upon insertion of the disposable device in the reader, the reader establishes establish fluidic connection with the vent holes. The vent holes are in fluidic connection with valves within the reader. These valves allow the reader to open or close the vents as required.

The valves may be solenoid operated plunger type valves or pinch valves or air operated piston valves, for example.

At the start of the test and/or initialization sequence, the vent valve V1 is open to atmosphere and thus allows venting of the waste channel 114. At the same time, vents V2 and V3 are kept in closed position thus sealing off all other channels.

The pump membrane 400 is pushed down to remove air from the pumping chamber. With vent V1 in open position and V2, V3 in closed position, the air escapes through V1 without affecting the sample contained within the diluted sample cavity 201. This primes the pump 400 for a suction operation. Next, vent V3 is opened and V1, V2 are closed. This allows the pump to move fluid in the diluted sample cavity 201. The pump actuator in the reader gradually releases the pump membrane 400 thereby creating suction in the fluid channels. Due the suction, the diluted sample moves past the capillary stop 101 and into the sample metering well 102. A fluid sensor FS1 positioned at the end of the sample metering well 102 senses the presence of fluid (sample) in its view field and the control unit of the reader stops the movement of the pump actuator and the pump membrane 400 and thus stopping the movement of diluted sample in the sample metering well 102 after it has filled the sampled metering well 102.

Fluid sensors FS1 and FS2 may be non-contact optical reflectance or transmission type sensors as part of the reader.

Next, vent V2 is opened and V1, V3 are closed. The pump actuator then further releases the pump membrane 400 to further pull the diluted sample into the mixing chamber 103. At this time, air is pulled into the cartridge through the vent V2, which 'cleaves' off a slug of the diluted liquid sample present in the sample fluid channel. The air thus isolates a slug of diluted saliva sample of a known volume within the sample metering well 102, thereby providing a controlled and metered volume of sample for testing.

Additionally, the sample metering well 102 may contain solid reagents that modify the diluted saliva sample as a part of the assay for analyte detection within the saliva sample. In one embodiment, these reagents are in the form of a freeze dried/lyophilised bead(s) that may include antibodies conjugated with a fluorophore and sugars or other stabilizers for stability. The bead(s) may be placed within the sample metering well 102 of the cartridge during assembly of the disposable device. The reagents may be in the form of multiple small pellets or powder form for improved dissolution. The surface of the sample metering well 102 may be spray coated with the reagents to allow better distribution of the dissolved regent within the slug of diluted saliva sample.

The lyophilised bead or other material containing the reagent dissolves upon contact with the diluted saliva sample. Owing to the low diffusivity of proteins within saliva, the dissolved reagents typically create a high concentration zone within the slug of saliva sample. For accurate testing, the reagents need to be uniformly dissolved within the entire volume of metered sample.

Uniform distribution of reagents within the saliva sample is achieved by passing the saliva sample through a mixing chamber 103.

Mixer Operation

The mixing chamber 103 is a passive microfluidic mixer which improves the concentration distribution of the dissolved reagents within the metered slug of the diluted sample.

In the disposable device disclosed herein, the mixing chamber 103 achieves mixing by manipulating the fluid flow to enhance the chaotic advection.

In one preferred embodiment the mixer 103 is a serpentine channel which utilizes the variation of speed of fluid around the bends of the sample fluid channel. This difference in speed of fluid between the inside and outside radius of the bend of the serpentine channel creates advection within the cross section of flow. As the fluid moves along the alternating bends of the serpentine channel, the chaotic advection increases and thus enhances mixing. In some embodiments, the fluidic channels, and in particular one or more serpentine channels have an inner diameter of at least 50 um, at least 100 um, or at least 500 um. Such channels may be readily formed using less expensive molding techniques and/or may allow better mixing, particularly during the back and forth movement and movement around any curves in the channels.

Figure 18A:
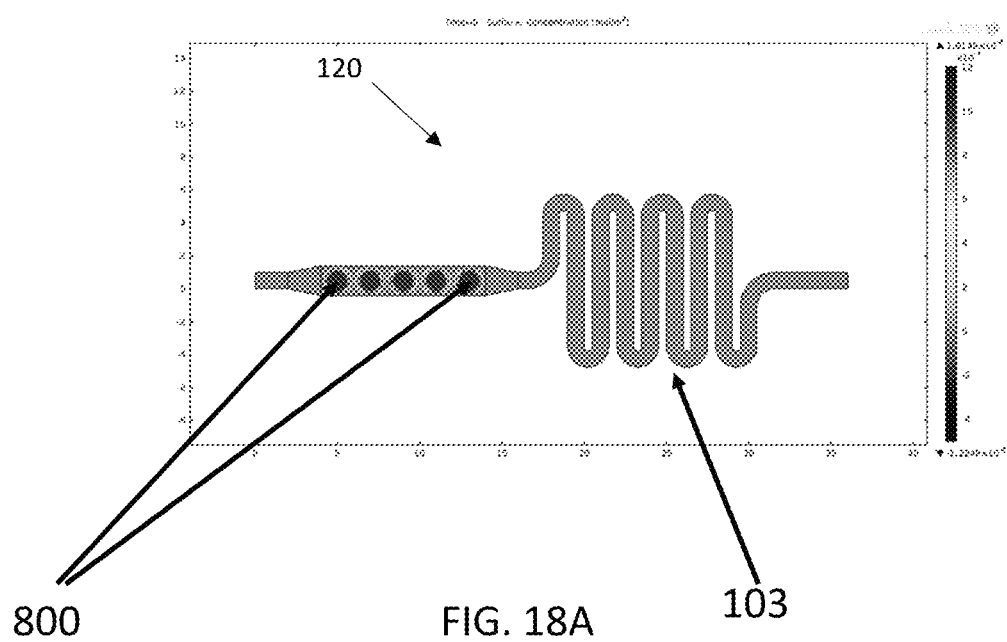
FIGS. 18A and 18B show part of a microfluidic circuit with a serpentine mixer useful for mixing a sample and a plurality of dried beads containing a binding agent.
Figure 18B:
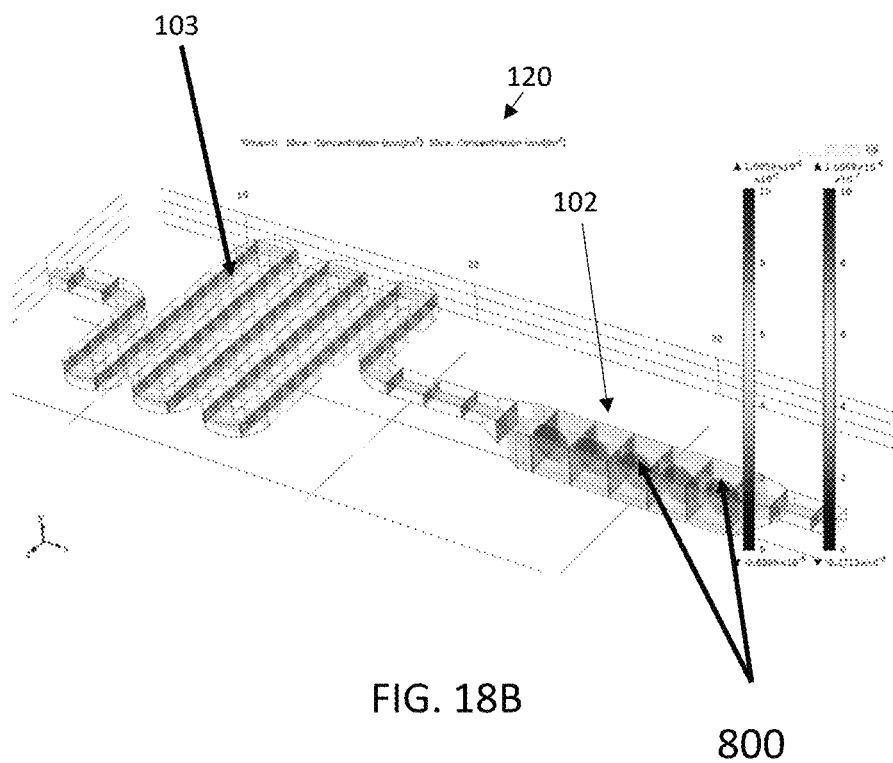

The pump actuation continues to release the pump membrane to pull the metered sample into the mixing chamber 103 and then stops. To reduce the length of channel required for mixing, a multi pass approach may be applied. The pump actuation is reversed and the pump membrane 400 is pushed down to move the metered saliva sample back into the sample metering well 102. The pump actuation is again reversed to pull the sample back into the mixing chamber 103. This process can be repeated multiple times to increase the mixing. FIGS. 18A and 18B shows concentration maps for a fluidic circuit with a serpentine channel and a sample well. FIG. 18A shows a simplified view and FIG. 18B shows an expanded view of a fluidic circuit 120 with a serpentine channel and sample well 102 for mixing a sample. Sample well 102 contains beads 800 with reagent, e.g. detectably labeled antibody. Diluted bodily fluid enters sample well 102 from diluted sample cavity 201, diluting and dissolving beads 800, forming metered sample. The scales on the right indicates reagent concentration (e.g., detectably labeled antibody) in different shades. The highest concentration is in the beads as shown by the dark color. As fluid moves along the alternating bends of the serpentine channel and back and forth between the serpentine channels and even into the sample well, reagent concentration becomes more consistent. In one embodiment, a relatively uniform distribution was achieved within 3-7 passes of the sample through the mixing chamber 103.

In a Split and Recombine (SAR) configuration, the fluid channel splits into two or more separate channels and then recombine into a single channel, or a 3-Dimensional Serpentine configuration with cross ridges.

For microfluidic flow, the Reynolds number is typically <1 and hence, diffusion is the dominant mode for mixing of fluids. Typically, assay reagents are small proteins and have low diffusivity in saliva. In addition, diffusion is a very slow process which makes it difficult to mix fluids at microfluidic scales.

Microfluidic mixing schemes can be either "active", where an external energy or force is applied to perturb the sample species (e.g., a mixing paddle, etc.), or "passive", where the contact area and contact time of the species samples are increased through specially-designed microchannel configurations.

For a disposable device, active mixing introduces many problems including complicated fabrication, increased cost etc. Passive micromixers contain no moving parts and require no energy input other than the pressure head used to drive the fluid flows at a constant rate. Due to the laminar characteristics of micro-scaled flows (Reynolds<1), mixing in passive micromixers relies predominantly on chaotic advection.

After the mixing step the sample is held within the mixing chamber 103. The capillary stop 104 at the exit of the mixing chamber prevents any movement of sample past the capillary stop 104 due to capillary action.

The vent V1 is then opened and V2, V3 are closed. At this point the blister actuator within the reader pushes down on the blister pack 300. The actuator pushes down on the blister pack 300 in controlled steps till the blister bursts and releases the control fluid out of the blister pack 300 and into the control fluid channel.

The blister actuator pushes further on to the blister pack 300 to push the control fluid into the control metering well 106. A fluid sensor FS2 positioned at the end of the control metering well 106 senses the presence of the control fluid in its view field when the control metering well 106 has been filled and the control unit of the reader stops the movement of the blister actuator and thus stopping the movement of control fluid in the control metering well 106.

The pump actuator then pushes down on the pump membrane 400. Since the pump is located upstream the control metering well 106, this pushes air into the control fluid channel which 'cleaves' off a slug of the control fluid present in the control fluid channel and control metering well 106. The air thus isolates a slug of control fluid of a known volume within the control metering 106, thereby providing a controlled and metered volume of control fluid for measurements.

Additionally, the control metering well 106 may contain solid reagents that modify the control fluid as a part of the assay measurements/testing. In the preferred embodiment, these reagents are in the form of a freeze dried/lyophilised bead(s). The bead(s) may be placed within the control metering well 106 of the cartridge during assembly of the disposable device.

The reagents may be in the form of multiple small pellets or powder form such as for improved dissolution. A control reagent may include one or a plurality of types of control reagents. Such reagents may be in a single bead, pellet, powder or other form, or may be in a plurality of beads, pellets, powders or other forms or a combination (e.g., one control reagent in a bead, another control reagent in a powder, etc.). A control reagent may be an antibody or other molecule configured to bind to a substance of interest (e.g., a drug, a legal substance, an illegal substance, a metabolite of such substances and so on). Two or more control reagents may be used to assay a single substance such as by using a first control reagent to detect a substance of interest and using a second control reagent to detect a metabolite (or different epitope or part) of a substance of interest.

The surface of the control metering well 106 may be spray coated with the reagents to allow better distribution of the dissolved regent within the slug of control fluid.

The lyophilized bead containing the reagent dissolves upon contact with the control fluid. For accurate testing, the reagents need to be uniformly dissolved within the entire volume of the metered control fluid.

Uniform distribution of reagents within the control fluid may be achieved by passing the control fluid through a mixing chamber 107. The mixing method is the same as described for the diluted saliva sample.

After the mixing step in some examples the control fluid may be held within the mixing chamber 107. The capillary stop 108 at the exit of the mixing chamber 107 prevents any movement of the control fluid past the capillary stop 108 due to capillary action. In other examples, the control fluid may be moved out of mixing chamber 107 immediately after mixing and into chip channel 109 for assay.

At this point, at least the sample fluid or both the sample and control fluids are held stationary within the respective mixing chambers for a fixed duration (typically 5-10 minutes). This allows for antibodies to bind with the analyte in the sample. FIG. 14A illustrates the kinetics of antibody binding with analyte in the sample during the sample incubation phase.

After incubation of the sample and control fluids, the pump actuator pushes down on the pump membrane 400 to move the control fluid out of the mixing chamber 107 and into the chip channel 109. The pump actuator pushes down on the membrane 400 a known amount which in turn moves the control fluid a known distance within the chip channel 109. The control fluid is stopped at a point in the chip channel 109 such that the control fluid covers the entire sensing area of the chip 3000. At this point optical measurements are made to sense the analyte reaction within the control fluid.

Post-measurement, the entire metered volume of control fluid is pushed further into the waste well 207. The selected chip channel and pump volume ensures that the entire chip channel 109 is empty after pushing the control fluid into the waste well 207.

Next, vent V2 is opened and V1, V3 are closed. The pump actuator then moves in reverse direction to release the pump membrane 400 and create suction within the sample fluid channel. This moves the incubated sample out of the mixing chamber 103 and into the chip channel 109. The fluid is moved a known amount such that the metered volume of the incubated sample covers the entire sensing area of the chip 3000. Optical measurements are made to sense the analyte reaction within the saliva sample.

Upon completion of measurements, the pump is released completely. This moves the saliva sample out of the chip channel 109 and into the control fluid channel which now functions as a secondary waste well. Since many tests only require the detection of a threshold amount of the analyte such as a drug, a single control sample having the analyte at the threshold concentration is sufficient to establish whether the saliva sample has a concentration of analyte that is greater than, less than, or equal to the threshold concentration. A readout to a user in such a case may indicate "Pass" or "Not detected" or "Fail" or "Detected or "Error" or the like. If an absolute concentration of the analyte is desired instead, multiple blister packs having varying concentrations of the analyte of interest can be added to the cartridge and tested to construct a calibration curve.

The reader may coordinate and control (e.g., using a controller comprising one or more processors) the operation of the vents (e.g., opening, closing), the pressure (increase, release, hold) on the pump (pumping membrane), the scan head, etc.

As indicated above, included herein is a method for analyzing a bodily fluid from a subject. A bodily fluid may be analyzed for detecting for one or more than one substances of interest (analytes), such as 2, 3, 4, 5, or more than 5 substances of interest. The method may include the steps obtaining or having obtained a bodily fluid sample from a subject, the sample suspected of containing a first analyte. Although any bodily fluid (or biofluid) such as blood, breast milk, plasma, sweat, tears, urine, etc., may be used, in general the method uses an oral fluid such as a saliva sample that may readily be obtained non-invasively and without requiring any special facilities such as a lab or bathroom. Such a fluid may be readily obtained from a subject by a person having no medical training and no or very little special training. FIGS. 13A-13E show how a method for analyzing a body fluid from a subject for a substance of interest.

A method as described herein may include the steps of mixing the bodily fluid sample with a first detection reagent comprising a first aliquot of a first binding agent. In general a first binding agent will include or contain or will bind to a detectable label. A first detection reagent may include a plurality of binding agents (second, third, fourth, etc.). A detectable label associated with a binding agent may include a label detectable by a reader using a laser and evanescent sensing. One or more than one types of detectable labels may be used. For example, detection of each of a plurality of analytes may use different detectable labels such that each analyte may be analyzed. In some examples, two or more analytes may use the same label. For example, a binding agent for two different opioids may use the same label such that a bodily sample can be determined to have more than an acceptable amount of "opioid". In some examples, a first (second, third, etc.) binding agent is a detectably labeled antibody configured to bind a substance of interest (first analyte, second analyte, third analyte, etc.) in the bodily sample to generate a sample mixture. A label may be a fluorophore attached to or configured to be attached to an antibody. A method as described herein may include a step of incubating the sample mixture under conditions configured to bind first analyte (second analyte, third analyte, etc.) to the first binding agent (detectably labeled antibody; second binding agent, third binding agent, etc.) to generate a reacted sample from the subject wherein first (second, third, etc.) detectably labeled antibody that is not bound to first analyte (second, third) has an available epitope. The amount of antibody may be in excess of analyte. In other words, only some of the available antibody may be bound to analyte. A method as described herein may include providing a first control sample comprising a first control aliquot of first (second, third, etc.) binding agent. A binding agent may be one or more detectably labeled antibodies wherein the antibodies are not bound to an antigen or analytes and have an available epitope. Such a first control aliquot may include a plurality of antibodies, which may be initially be found in a test device as non-aqueous or lyophilized or dried as beads, pellets, sprays, etc. and may be located in control metering well 106 as described elsewhere herein and may be reconstituted using solution from blister pack 105. A non-aqueous or lyophilized or dried beads, coating, pellets, sprays, etc. may contain a single binding agent or may contain a plurality of binding agents. For example, a single dried bead, coating, pellet, spray may contain just 1 binding agent or may contain 2, 3, 4, 5, or more binding agents. Alternatively, a system as described herein may include a plurality of dried beads, coatings, pellets, or sprays and such each one may include only a single binding agent or only a subset of binding agents. A particular delivery form for binding agent(s) may be chosen for cost or ease of manufacturability, ease or speed of reconstitution or so on. A first control sample may include a one or more than one detectably labeled binding agents. A method for analyzing a bodily fluid as described herein may include the step of providing at least one analyte sensing site having a supply of first antigen (second antigen, third antigen, etc.) attached thereto. At least one analyte sensing site may include 1 or more (2, 3, 4, 5, 10, 20 or more or anything between these numbers) of analyte sensing sites such as analyte sensing sites 3103 shown in FIG. 8B. A method for analyzing a bodily fluid as described herein may include the steps of passing the first control sample over the at least one sensing site to thereby conjugate first binding agent (detectably labeled antibody) to the first (second, third, etc.) antigen in the at least one sensing site and thereby activate a first (second, third, etc.) detectable control signal.

A method for analyzing a bodily fluid from a subject may also include the step of after the passing the first control sample step, measuring over time detectable signal from the at least one sensing site to generate a first set of measurements. Such measurements may be taken over time from the same at least one sensing site. As shown in FIG. 8B and described in detail elsewhere herein, detectable signals from a plurality of such sites may be collected in a single waveguide 3101 (a sensing waveguide). In a particular example, detectable signals (optical radiation) from between 6 and 10 analyte sensing sites are collected into a single sensing waveguide and assayed. Detectable signals (optical radiation) for each detectable signal (fluorophore) may be collected over time, measured and plotted on an X-Y graph to obtain a slope based on signal intensity vs time. As discussed in more detail below, the slope of the control graph may be compared with the slope of signal intensity vs time for a bodily sample such as handled as described herein to calculate an amount of analyte present in the bodily sample. Although only one binding agent may be present, in other cases a plurality of different binding agents (antibodies) may be present in an aliquot of a single reagent or in a single control metering well each with a different detectable label. In general, a separate control graph is generated for each detectable signal (for each antibody).

A method for analyzing a bodily fluid from a subject may also include the step of passing the reacted sample from the subject over the at least one analyte sensing site and conjugating reacted sample antibody having the available epitope to first antigen in the at least one sensing site and thereby activating a first detectable sample signal from the at least one sensing site; after the passing the reacted sample step, measuring over time detectable signal from the at least one sensing site to generate a second set of measurements; and comparing the second set of measurements to the first set of measurements to thereby determine a level of first analyte in the bodily fluid; wherein first reacted sample does not substantially bind to the first antigen in the at least one analyte sensing site if first analyte is bound thereto. In some examples, a sample of bodily fluid is diluted prior to the mixing or incubating with a binding agent. A bodily fluid, especially an oral fluid such as saliva, may be relatively viscous and diluting the sample prior to analysis may make it easier to handle and assay.

This may conclude the rapid test and the cartridge can be removed from the reader module. The disposable device 1000 may then be packaged in a sealed container to be sent out to a forensic or other lab for confirmatory testing. The sealed container may be a sealable bag such as a Ziplock bag or a standard evidence bag used by the law enforcement agencies, for example. In addition to using a standard evidence bag, chain of custody can be maintained and documented by use of barcodes or other identifiers which can be attached to the swabs and/or other parts of the system.

Assays as described herein may be especially useful for detecting a substance of interest and especially for detecting a substance that may alter cognition and affect a subject's actions or behavior (e.g., a drug, a drug of abuse, a legal substance, an illegal substance, a metabolite of such substances and so on). Substances of interest may be detected directly or a form of a substance, such as a metabolite, may be detected. In some examples, a single substance of interest may be detected using the systems described herein and in other examples, a plurality of different substances may be detected using a multiplex assay. In some examples, a single substance of interest may be detected using two assays in a system. For example, or more control reagents may be used to assay a single substance such as by using a first control reagent to detect a first substance and using a second control reagent to detect a metabolite (or different epitope or different part) of the same substance.

Substances that may be analyzed using the systems described herein include cannabinoids, depressants, hallucinogens, muscle relaxants, narcotics, sleep aids, and stimulants. Substances that may be analyzed using the systems described herein include 11-Hydroxy-Δ9-tetrahydrocannabinol (11-OH-THC, 11-hydroxy-THC, or 11-nor-delta-9-THC-COOH), 11-nor-9-carboxy-THC (THC-COOH), amphetamine, another cannabinoid, a barbiturate, benzodiazepine, benzoylecgonine, buprenorphine, cocaine, d-Amphetamine (AMP), ecstasy (MDMA), ethyl alcohol, fentanyl, heroin, heroin metabolite, hydrocodone, lysergic acid diethylamide (LDS), mescaline, methadone, methadone metabolite, methaqualone, morphine, an opiate, oxazepam, oxycodone, phencyclidine, synthetic cannabinoid, tetrahydrocannabinol (THC cannabinoid), and so forth.

In some particular examples, one or more than one or all of the following are sensed using the systems described herein: amphetamine, benzodiazepine, cocaine, marijuana, methamphetamine, and opiates. In a particular example, at least three of benzodiazepine, cocaine, fentanyl, and marijuana (THC) are sensed.

EXAMPLES

Figure 15A:
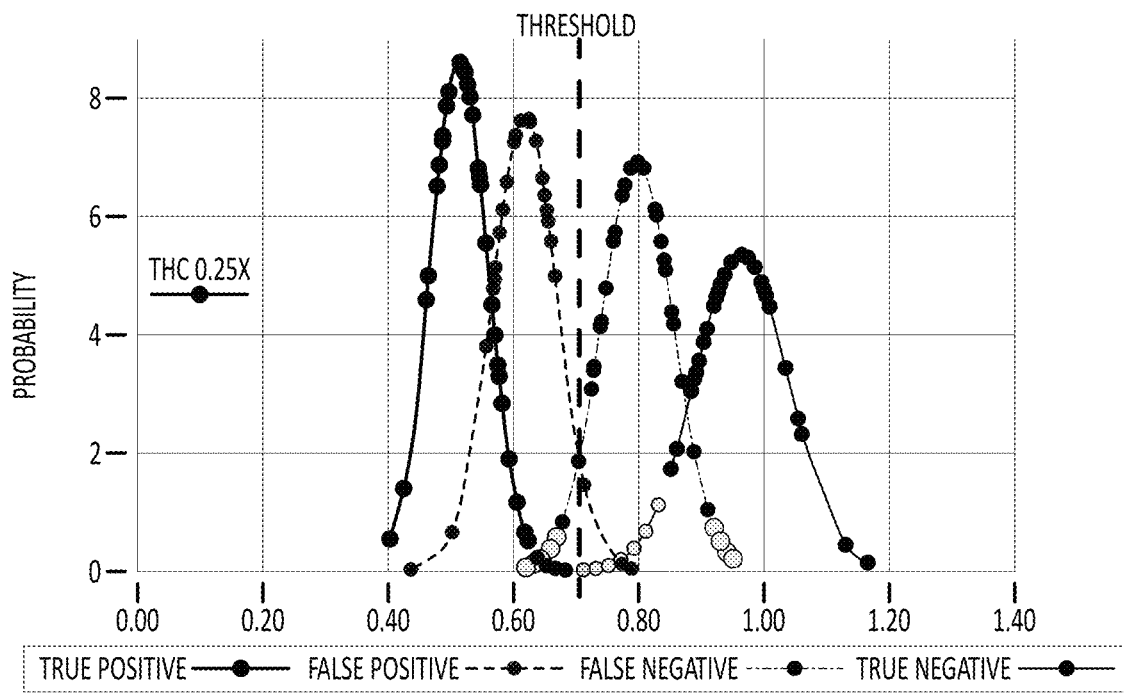
FIGS. 15A and 15B shows results of an assay signal distribution as described herein for detecting the presence of marijuana (THC; tetrahydrocannabinol) in a sample.
Figure 15B:
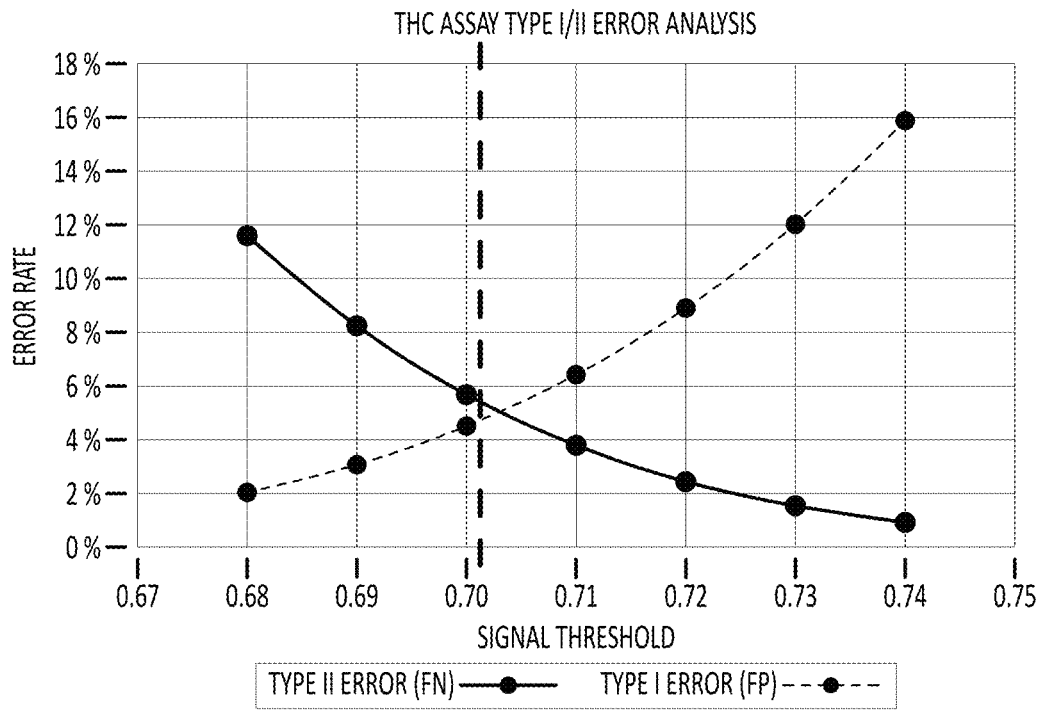

Example 1 FIGS. 15A and 15B shows results of an assay signal distribution as described herein for detecting marijuana (THC; tetrahydrocannabinol) in a sample. An assay is a balance between specificity and sensitivity: calling true negatives (TN; calling a result that was actually negative negative), false negatives (FN; calling a result negative when it was actually positive), false positives (FP; calling a result positive when it was actually negative) and true positives (calling a results positive when it was actually positive). FIG. 15A shows a graph of probability for (from L to R) true positives, false positives, false negatives, and true negatives using the systems and assays described herein. A threshold value of about 0.7× provides a balance between minimizing both false negatives and false positives (see the point at which these two curves overlap) and maximizing true negatives and true positives. Other threshold values could also or instead be chosen to increase/improve either specificity or sensitivity. FIG. 15B shows a graph of error rate vs signal threshold. At a threshold around 0.7 (0.72) the error rate from false positives (the curve starting high on the left side of the graft) and the error rate from false negatives (the curve starting low on the left side of the graft) are both less than 6%. This graph assumes that the 30 measurement of the samples are normally distributed.

Figures 16A, 16B:
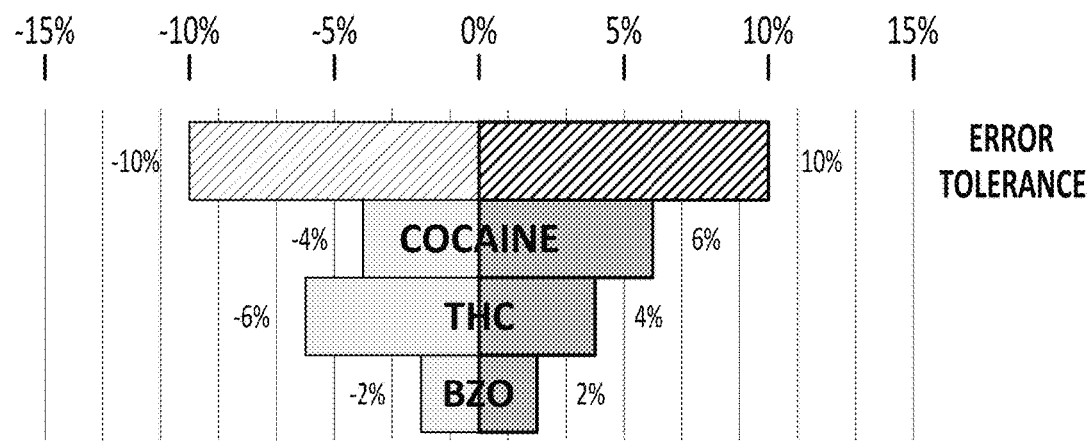
FIGS. 16A and 16B shows results from a multiplex assay as described herein for detecting cocaine (COC), marijuana (THC; tetrahydrocannabinol) and benzodiazepine (BZO) from a bodily fluid sample.

Example 2 is shown in FIGS. 16A and 16B. These figures show an example of error rate results from a multiplex assay as described herein for detecting cocaine (COC), marijuana (THC; tetrahydrocannabinol) and benzodiazepine (BZO). FIG. 16A shows error rates for false positives (the bars on the left side of the graph; left of 0%)) and false negatives (the bars on the right side of the graph; right of 0%). Error rates are less than 10% for the analytes tested cocaine (COC), marijuana (THC; tetrahydrocannabinol) and benzodiazepine (BZO). False positive and false negative error rates for cocaine are around or less than 4% and 6% respectively for cocaine; around or less than 6% and 4% respectively for THC, and around or less than 2% and 2% respectively for benzodiazepine (BZO) at 0.6×. Other threshold values could be chosen to minimize either false positives or false negatives.

Figure 17A:
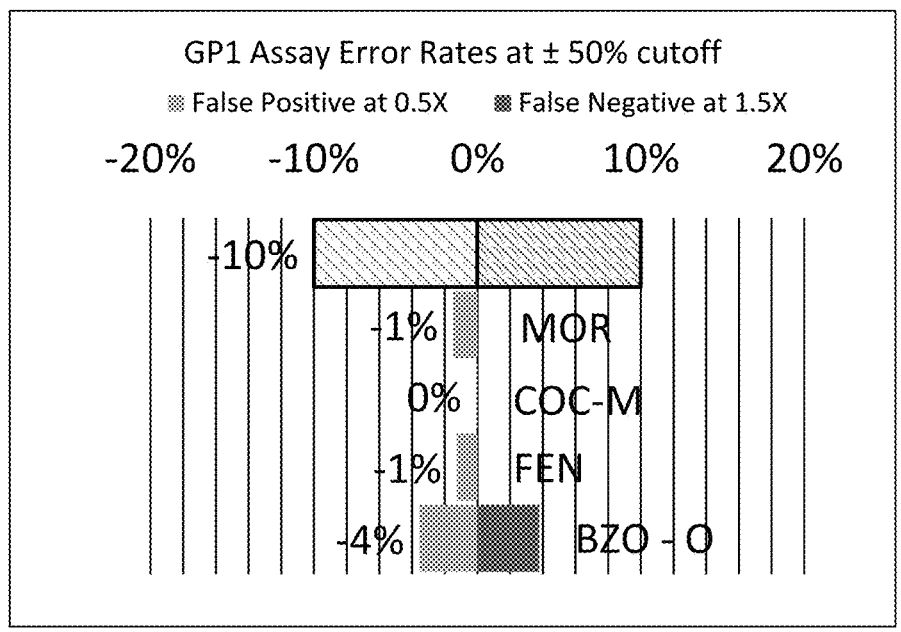
FIGS. 17A-17C show results from a multiplex assay as described herein for detecting cocaine (COC-M), fentanyl (FEN), morphine (MOR) and benzodiazepine (BZO-O) from a bodily fluid sample.
Figure 17B:
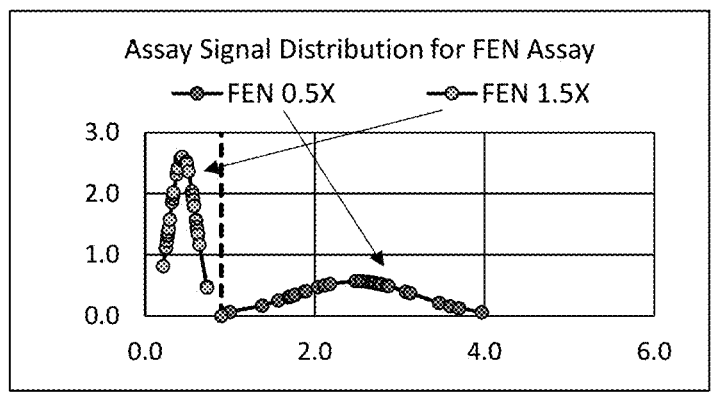
Figure 17C:
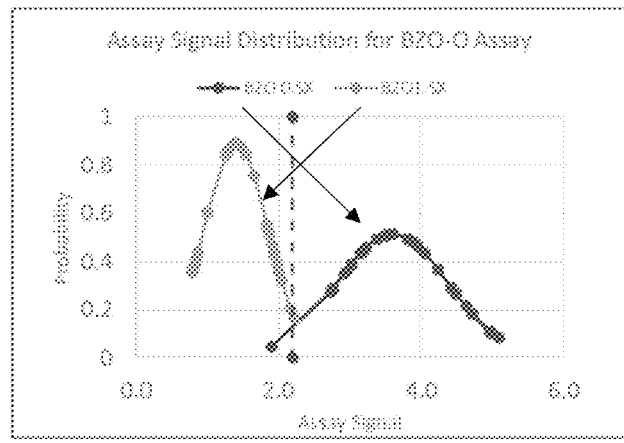

Example 3 is shown in FIGS. 17A-17C. These figures show results from a multiplex assay using the systems and methods described herein including dried beads containing reagents and a serpentine mixer for detecting cocaine (COC-M), fentanyl (FEN), morphine (MOR) and benzodiazepine (BZO-O). Errors are less than 10% and less than 4% in an FIG. 17A shows error rates for false positives (the bars on the left side of the graph; left of 0%) and false negatives (the bars on the right side of the graph right of 0%). Error rates are less than 10% for the analytes tested. False positive and false negative error rates for morphine are around or less than 1% and 0%, around or less than 0% and 0% respectively for cocaine, and around or less than 1% and 0% respectively for fentanyl, and around or less than 4% and 4% for benzodiazepine (BZO-O), with false positives at 0.5× and false negatives at 1.5×. Other threshold values could be chosen to minimize either false positives or false negatives. FIG. 17B shows assay signal distribution for the fentanyl (FEN) assay shown in FIG. 17A for fentanyl at 0.5× and 1.5×. FIG. 17C shows a graph of the probability (Y-axis) of an assay signal distribution for the benzodiazepine (BZO-O) for the assay shown in FIG. 17A.

Figure 19A:
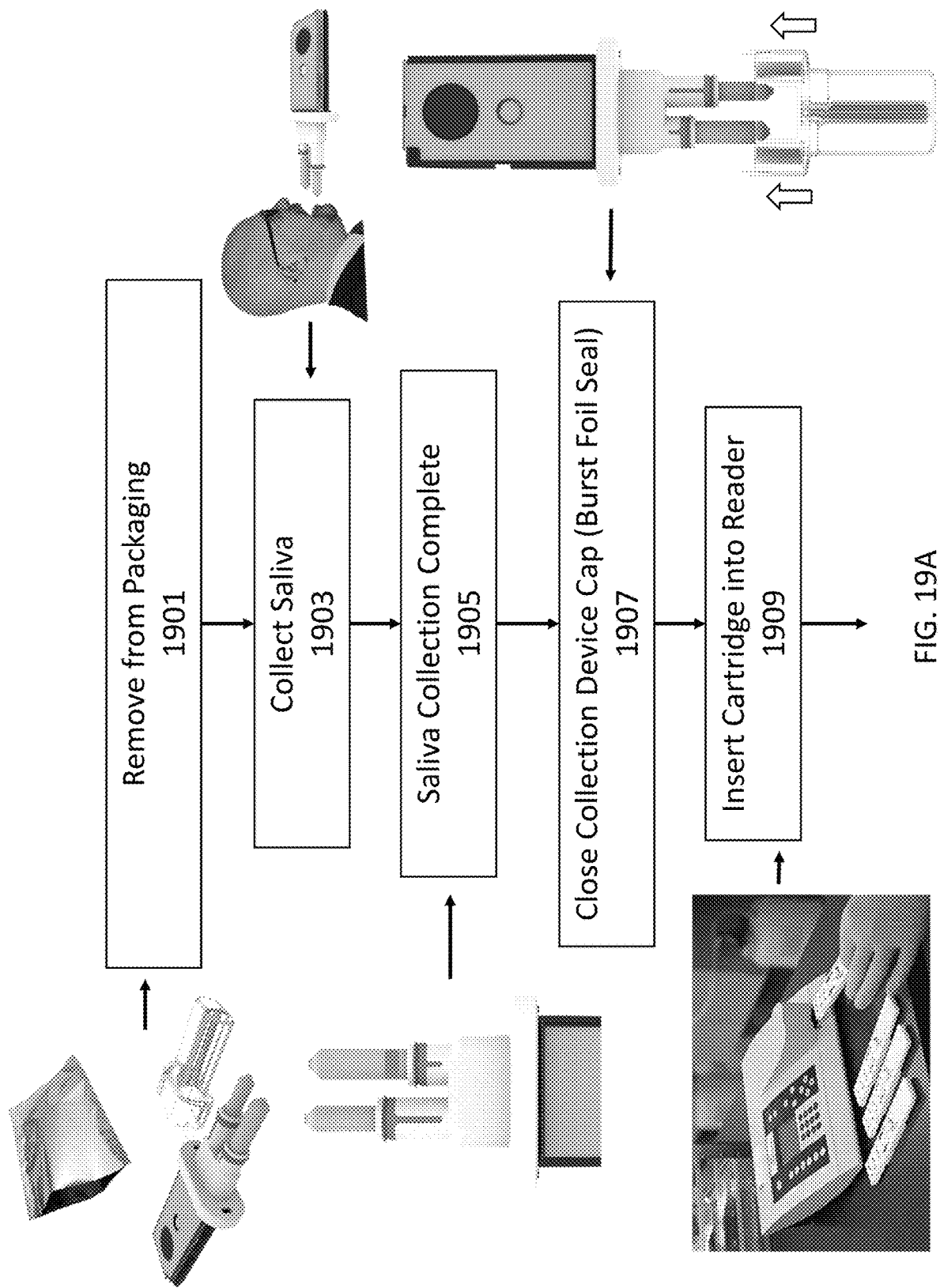
FIGS. 19A-19B illustrate a method of operating the cartridge (including an integrated saliva collection system) to test a subject's saliva, as described herein, including both local (e.g., immediate) testing with a reader similar to that shown in FIGS. 21A-21B, and confirmation testing.
Figure 19B:
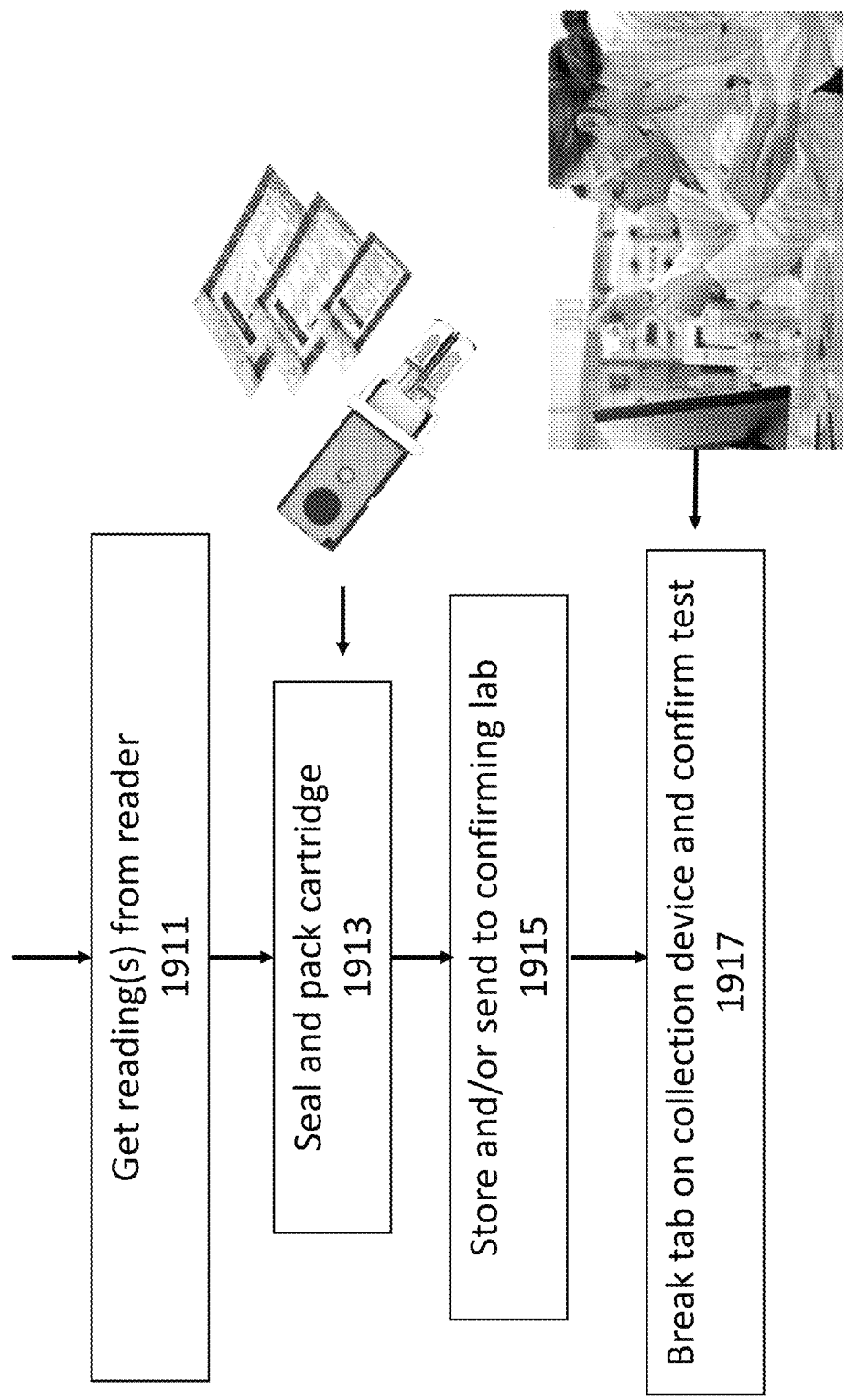

FIGS. 19A-19B show (with individual illustrations) one example of a method of operation of an apparatus as described herein for sampling saliva. In this example, the cartridge, including a saliva collection system (also referred to as a saliva collection sub-systems) is removed from a sterile packaging 1901, and includes the cartridge body (coupled to the collection body) and a cap. The first and second swab pistons extending from the collection body may then be inserted into a subject's mouth to collect saliva 1903; an indicator (colorimetric indicator) on the side of the device may change color to indicate when it is full, and saliva collection is complete 1905. The cap may then be inserted and snapped over the first and second swab pistons (containing the saliva sample); the action of attaching the cap may pierce a frangible cover within the cap and may force the one or more fluids (e.g., a dilution fluid in one side, corresponding to the first swab piston, and a preservation solution in the second side corresponding to the second swab piston) to mix with the saliva samples. The first and second sides may be isolated from each other (fluidically isolated) 1907. The sample to be immediately tested is diluted a predetermined amount and dispensed into the diluted sample cavity within the cartridge. The cartridge may then be inserted into a reader 1909 for processing and reading.

FIG. 19B continues the method shown in FIG. 19A. In FIG. 19B, the cartridge reader may then process the fluid within the cartridge via the fluidic circuit(s), as will be described in greater detail in reference to FIGS. 20A-20N, below, and resulting signals may be read out, as described above 1911. The readout may be qualitative (e.g., above a threshold, within a range indicating "positive", "negative" or "inconclusive", etc. for the presence/absence of a drug of addiction), and/or it may be quantitative (estimating concentration values). The output may be presented and/or stored and/or transmitted.

The entire cartridge may then be stored and/or transmitted for confirmation processing, e.g., at a remote laboratory 1913, 1915. For example, the cartridge may be sealed in a package. The second sample (mixed with the preservation solution within the cartridge, e.g., the collection sub-system portion of the cartridge) may be kept indefinitely until confirmation testing is desired. When retesting of the stored sample is desired, the cartridge may be unsealed, e.g., the tab on the collection device may be broken, and the confirmation test performed 1917.

Any of the processing steps described herein using the microfluidics on the cartridge may include manipulation, e.g., by a reader, of the fluidics circuit within the cartridge. FIGS. 20A-20N illustrate one example of fluidics circuit (similar to that shown in FIG. 7). In FIG. 20A, the circuit is illustrated; FIG. 20B shows a legend or key that may be helpful when reviewing the exemplary operation described and shown schematically in FIGS. 20C-20N.

FIG. 20C illustrates the initialization step, in which the pump (diaphragm) may be set up so that both pushing and pulling of fluid through the device may be allowed. In FIG. 20C, the reader (e.g., a pump piston on the reader) may be pushed at least partway in to deflect (e.g., approximately 50%) the pump diaphragm in the cartridge, as shown. In this case, valves in the reader keep the vents on either side of the diluted sample cavity closed, but leave the waste vent (downstream of the waste reservoir) open, so that only air may pass into the channels. The swab piston (also referred to herein as a swab plunger) in the saliva collection portion has already pushed diluted sample into the Diluted Sample Cavity (DSC) in the cartridge. A cap stop may prevent capillary movement of the sample.

In FIG. 20D, the sample may be metered (e.g., a predetermined volume of diluted sample) by the circuit. Once the reader has closed the waste vent valve and opened the vent downstream of the diluted sample cavity, the reader may then controllably release the pump piston so that the pump (diaphragm) applies negative pressure to pull a sample into the sample metering well (SMW) until a fluid sensor detects a fluid meniscus and stops the pull by holding the pump piston in place. The sample may be 'cleaved' (e.g., so that a bolus of air is added to cut off the metered sample from the diluted sample cavity), by the reader closing the vent downstream from the diluted sample cavity and opening the vent between the diluted sample cavity and the metering well ("sample well"). The pump may be allowed to pull fluid slightly, drawing a bolus of air behind the metered sample in the sample well, as shown in FIG. 20E, accurately separate a slug of metered volume of sample.

In this example, a lyophilised bead (e.g., including a fluorescently labeled antibody to the drug(s) to be identified) may be present in the sample well and may dissolve in the sample. The fluid may then be pulled into the serpentine mixer and moved back and forth within the mixer multiple times to achieve thorough mixing. This is illustrated in FIG. 20F. The reader may achieve this by extending and retracting the pump piston to controllably push and release the pump diaphragm on the cartridge, resulting in pushing and pulling the sample fluid within the mixer; as illustrated above, the mixer may be a serpentine channel. Once mixed, the fluid may be left in the sample channel and allowed to incubate, as shown in FIG. 20G. In some variations, the pump may be released (e.g., allowed to fully relax to a neutral position), by opening the vent downstream from the waste channel, and closing the vents upstream and downstream from the diluted sample cavity.

The control solution within the blister pack may then be dispensed. For example, in FIG. 20H, the blister pack is burst by applying a force (e.g., from a piston) to push the blister pack against the needle within the cartridge, and the control fluid is pushed into the control metering well (CMW) till a fluid sensor detects the meniscus and stops the reader (e.g., a piston for pushing the blister pack) from pushing further. In FIG. 20I, the control fluid may be metered by the reader pushing on the (now air-filled) pump diaphragm. The pump then pushes air into the control channel to accurately separate a slug of metered volume of control fluid. In this example, a lyophilised bead (e.g., fluorescently labeled antibody) in the CMW (control metering well) may dissolve in the control fluid. As shown in FIG. 20J, the control solution (fluid) may then be pulled into the serpentine mixer and moved back and forth within the mixer multiple times to achieve thorough mixing, again by applying pushing force (or relaxing the pushing force) to allow the diaphragm to move in and out, pushing and pulling the control solution through the second serpentine mixing channel. The control fluid is then left in the control channel to allow incubation. After incubation, the control fluid is pushed into the chip channel and data acquisition is done, as shown in FIG. 20K. In this example, the solution may be passed onto the chip and evanescent signals detected as described above. Thereafter, the control fluid may be pushed into the waste well till the chip channel is empty, as shown in FIG. 20L, by the reader pushing (via the pump piston) on the pump diaphragm.

Next, the sample may be pulled into the chip channel and data acquisition done, as shown in FIG. 20M. The vent downstream to the waste channel is closed, and the vent between the sample (metering) well and the diluted sample cavity may be opened, as shown, so that releasing the pump piston by the reader allows the pump diaphragm to apply negative pressure to pull the metered sample solution over the chip, allowing evanescent reading by the chip. Finally, the sample may be pulled into the control channel and pump chamber, as shown in FIG. 20N.

Figure 21A:
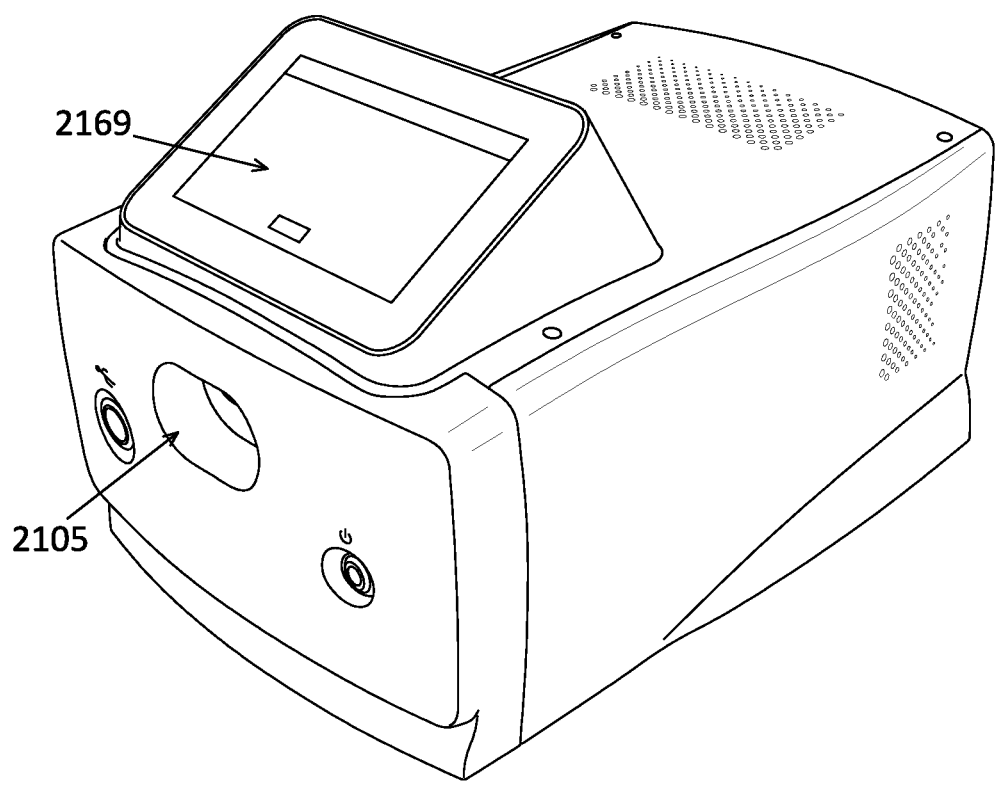
FIGS. 21A-21B show an example of a reader for reading a cartridge and automatically performing the method of operating the exemplary cartridge as described herein.
Figure 21B:
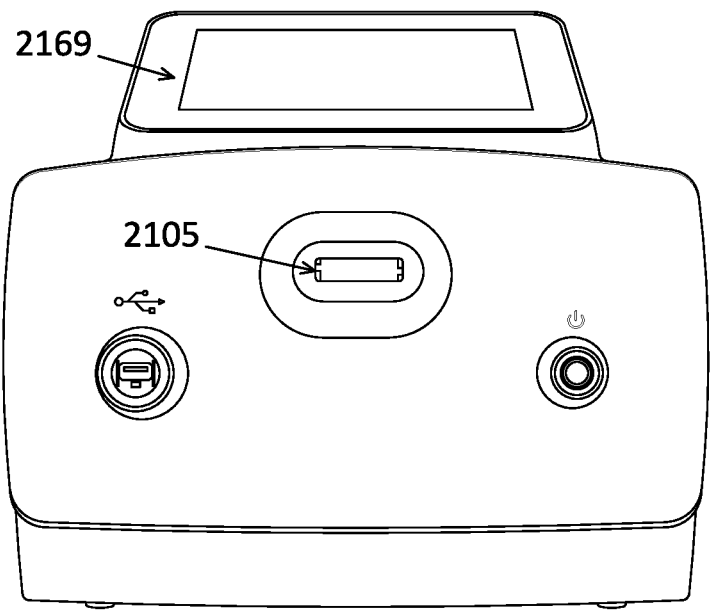

In general, any appropriate reader may be used. A schematic of one example of a desktop reader is shown in FIGS. 21A and 21B. In this example, the reader may include one or more processors (controllers) including a memory, and control circuitry, for controlling the pump piston, the valves, the fluid sensors, and the optical illumination source and optical detector for reading from the photonics chip, as well as hardware, software and/or firmware for processing signals from the photonics chip. The reader may also include one or more outputs (displays, memory, wireless or wired transmitters, printers, removable memory, etc.

In general, the reader apparatuses described herein (e.g., the optical reader devices) may include a cartridge holder for holding any of the removable cartridges described herein, a scan head coupled to a laser light source and an optical detector for applying excitation light to the photonics chip of a cartridge in the holder and detecting an emitted signal, a microfluidics manipulator for manipulating fluids in the cartridge (e.g., one or more valve controls, one or more membrane pumps, and one or more optical fluid sensors), an output for outputting the readings, and a controller for controlling and coordinating the operation of the scan head, light (e.g., laser) source(s), optical detector(s), microfluidic manipulator(s) and output. The apparatus may also include one or more inputs. The controller may include control circuitry (e.g., one or more processors, memory accessible to the one or more processors, clocks, wireless communications circuitry, etc.).

Figure 21C:
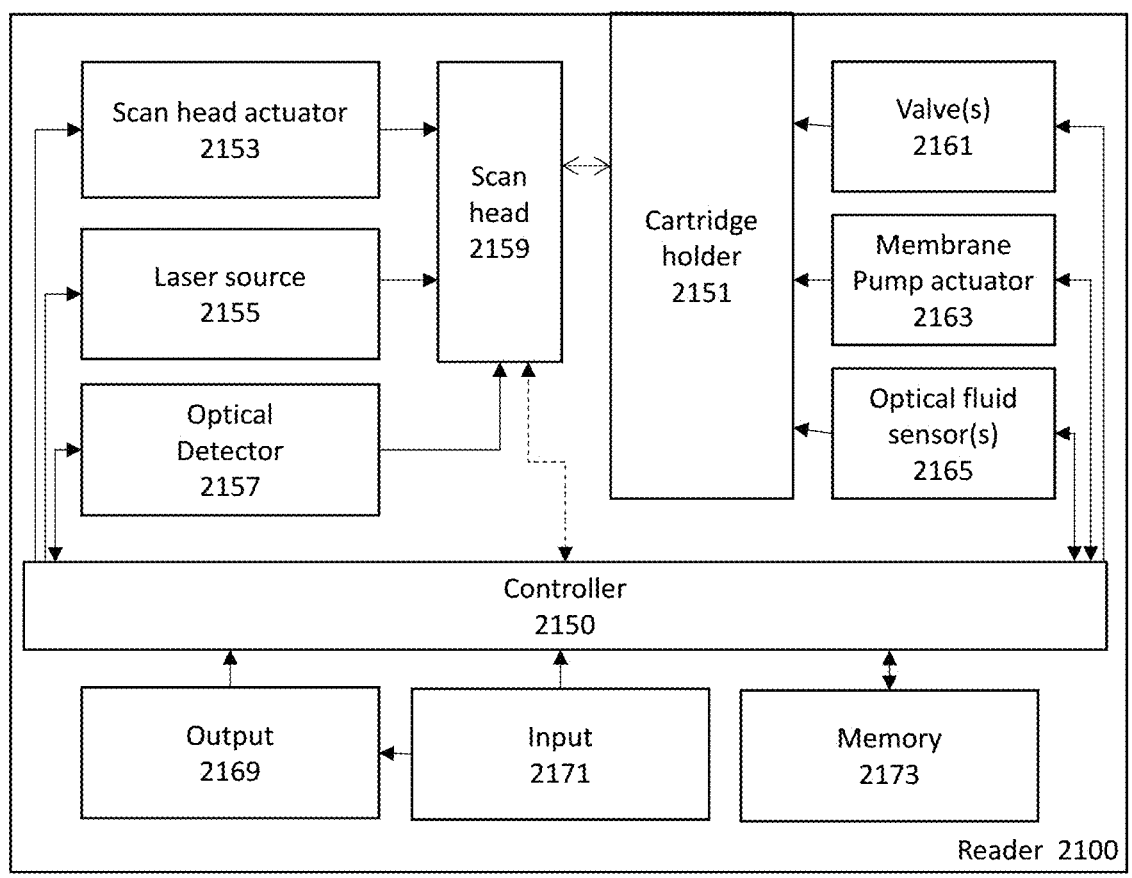
FIG. 21C is a schematic of one example of a reader as described herein.

For example, FIG. 21C is a schematic of one example of an apparatus as described herein. In this example, the reader 2100 includes a cartridge holder 2151, which may be referred to herein as a clamp, which may hold and secure the cartridge within the reader and align it. The cartridge holder may include a variety of alignment surfaces (e.g., pins, registration surfaces, etc.) as described in greater detail below. The cartridge holder may include or may be coupled with one or more valves controlled by one or more valve controls 2161. The valves may be plunger (e.g., solenoid) and/or pinch valves that may interface the valve openings on the cartridge to regulate fluid flow, as described above. One or more force applicators (e.g., membrane pump actuator 2163) may be included as well, to push against the membrane pump in the cartridge. The force applicator may be a piston, rod, or other extendable/retractable member that may apply force against the pump membrane by moving towards or away from the membrane. In some variations the force activator is a geared member (e.g., rod) that is controlled to move forward or backwards to deflect or relax deflection of the pump membrane, as described above. In some variations, the force applicator may be a balloon that is inflated/deflated to deflect or relax deflection. In general, the membrane pump actuator 2163 may apply force to increase deflection of the pump membrane of the cartridge, to hold a deflection of the pump membrane, and/or to relax deflection of the pump membrane. The membrane pump actuator may be integrated with the cartridge holder and/or it may be separate from the cartridge holder. In some variations the membrane pump actuator includes an arm for applying force to the membrane and a driver (e.g., a mechanical drive, a pneumatic driver, an electromagnetic driver, etc.) for driving the arm against the membrane. In some variations the arm may include a rounded end (e.g., a ball-shaped end, etc.) to avoid damaging the membrane pump. The arm may be hinged. A mechanical driver may include one or more gears. The driver may also include a sensor or detector for detecting the position of the arm relative to the cartridge and/or membrane pump, and/or for detecting the force applied by the driver. The detected position and/or force may be used as feedback to regulate the pumping.

The apparatus may also include a second force applicator for applying force to puncture, rupture or otherwise open the blister pack. For example, the apparatus may include a force applicator (e.g., rod, striker, etc.) for applying force to drive a piercing element (e.g., in or on the cartridge) to open a blister pack. The membrane pump actuator and blister pack force actuator may be controlled by the controller 2150.

One or more non-contact, optical fluid sensors 2165 may be included as part of the cartridge holder and/or in communication with the cartridge holder. As mentioned above, fluid sensors 2165 may be non-contact optical reflectance or transmission type sensors. The fluid sensors may communicate with the controller 2150.

The reader 2100 may also include a scan head 2159 within the reader housing. In general, the position of the cartridge in the cartridge holder is adjustable relative to the position of the scan head. Typically the scan head 2159 is movable relative to the cartridge holder, however in some variations the cartridge holder may also be adjustable or the scan head may be fixed in position while the cartridge holder position is adjusted. In FIG. 21C, the scan head position is movable relative to the cartridge holder and a scan head actuator may adjust the position of the scan head relative to a cartridge within the cartridge holder. The scan head actuator may be configured to move the scan head to adjust one or more of the x, y or z position of the scan head (and thus the output of the light/laser source 2155 and the input for the optical detector 2157) so that the scan head may optimally couple with the photonics chip, e.g., the edge of the photonics chip of the cartridge having access to the excitation waveguides and emission wave guides in the chip (see, e.g., FIGS. 8A-8B). In some variations the pitch, yaw and/or roll of the scan head may also be adjusted.

The light source 2155 may be part of the scan head or it may be separate from the scan head. In some variations the light source is a plurality of laser diodes that each couple to the scan head through a fiber line (e.g., as described below, a polarization maintaining single mode fiber). The optical detector(s) 2157 may be part of the scan head or may be separate from the scan head. In some variations the optical detectors may be detectors (e.g., photodiode detectors) that couple via a fiber to the scan head. For example, an array of photodiode detectors may couple to the scan head via a multimode fiber. The scan head may include a fiber coupler, and an end of each of the emission fibers (e.g., polarization maintaining single mode fibers connected to the laser diodes) and an end of each of the sensing fibers (e.g., the multimode fibers each coupled to a photodiode) may be exposed in a configuration that is complimentary to the configuration of the emission and detection waveguides on the edge of the photonics chip, as shown in FIGS. 8A-8B and 9A.

The controller may also control operation of the scan head actuator to align the scan head (and thus the excitation source, e.g., laser source, and the optical detector) with the cartridge, and may coordinate the application of control fluid and then test sample into the wells of the photonics chip and detection of signal from control and sample. Typically the reader and cartridges described herein may detect both control and sample signals from the same wells, thus minimizing error.

The controller may also receive input from a user via one or more inputs 2171, which may be a keyboard, touchscreen, dial, control, buttons, and/or wireless input from a remote processor (e.g., smartphone, computer, laptop, tablet, etc.). The controller may provide output 2169 to one or more screens (e.g., touchscreen, display, etc.), files, memory, printers, etc.

FIGS. 21D-21N illustrate another example of a reader device. In this example, a cartridge 2144 is shown inserted into the reader device 2100. The reader device in this example includes a scan head assembly 2144, including a first collection of fibers 2148 that connect to a plurality of light sources (e.g., laser diodes, not shown) via a connector 2152. A second plurality of fibers 2154 connects on one end to the scan head and couples to a plurality of detectors (e.g., photodetectors, not shown) to detect evanescent signals from the chip. The second plurality of fibers coupled to the detectors through a connector 2156. The fibers may be held in a channel 2165. The scan head assembly may be moved relative to the cartridge holder by one or more actuators (e.g., linear actuators) 2153.

Figure 21D:
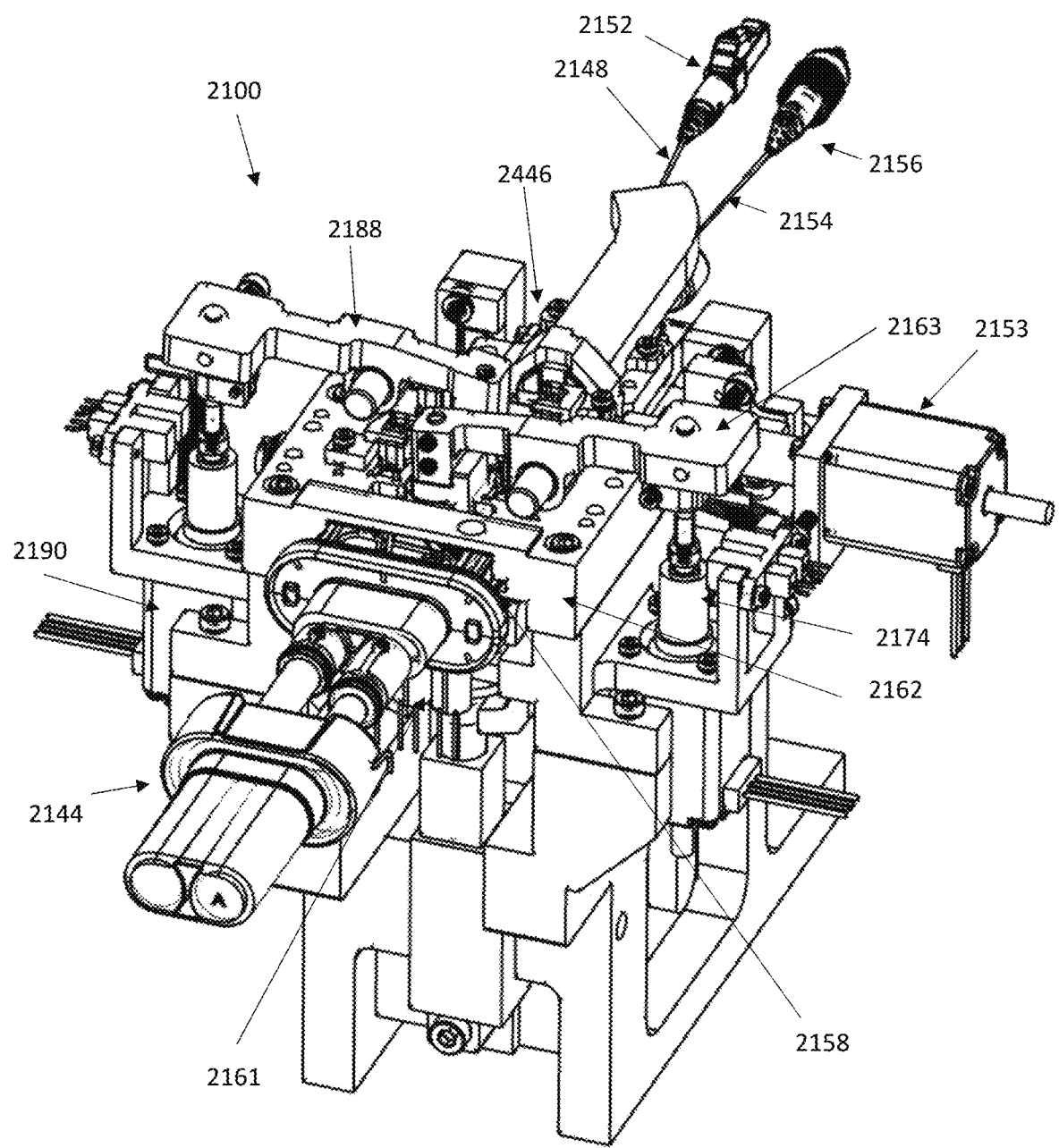
FIG. 21D shows a front perspective view of one example of a reader (the reader components may be housed within a housing, not shown), including a cartridge inserted into the reader.

The reader device in FIG. 21D also include a holder (clamp) assembly forming a slot 2158 into which the cartridge his inserted. The slot includes a reference surface in the z-direction (a pin at the back of the slot, not visible in FIG. 21D), as well as a reference surface in the x-direction (e.g. along the long side of the slot). The slot may include a track, flange, lip, rim, etc. for guiding and securing the cartridge (e.g., by mating with a corresponding lip, ring, flange, pin, etc.) on the cartridge. The cartridge holder (cartridge holder assembly) may include a top 2162, which in this example forms the opening and upper and side walls, and a bottom of base plate 2164, which is visible in FIG. 21E, showing the same device as in FIG. 21D, without a cartridge inserted.

This device may also include a plurality of valves 2161 and a membrane pump actuator 2163. In the example shown in FIG. 21D, the pump actuator is a rocker arm that is driven by a linear actuator 2174. The linear actuator may push or pull one end of the rocker arm and may lock the rocker arm in a pushed or pulled position, controlling the deflection or relaxation of a membrane pump of a cartridge held in the cartridge holder. As described below, the end of the rocker arm contacting the membrane pump may be ball-shaped (not visible in FIG. 21D or 21E). A second actuator 2188, also shown configured as a rocker arm that is connected to a linear actuator 2190 and may be used to apply force to rupture or otherwise open a fluid container (e.g., blister pack) on the cartridge.

The reader device may also include a controller having one or more processors (not shown) and one or more memories. In any of these variations, the components shown in FIGS. 21D and 21E may be covered by a housing, which may have an opening, door, etc. for inserting the cartridge (see, e.g., FIGS. 21A-21B).

Figure 21E:
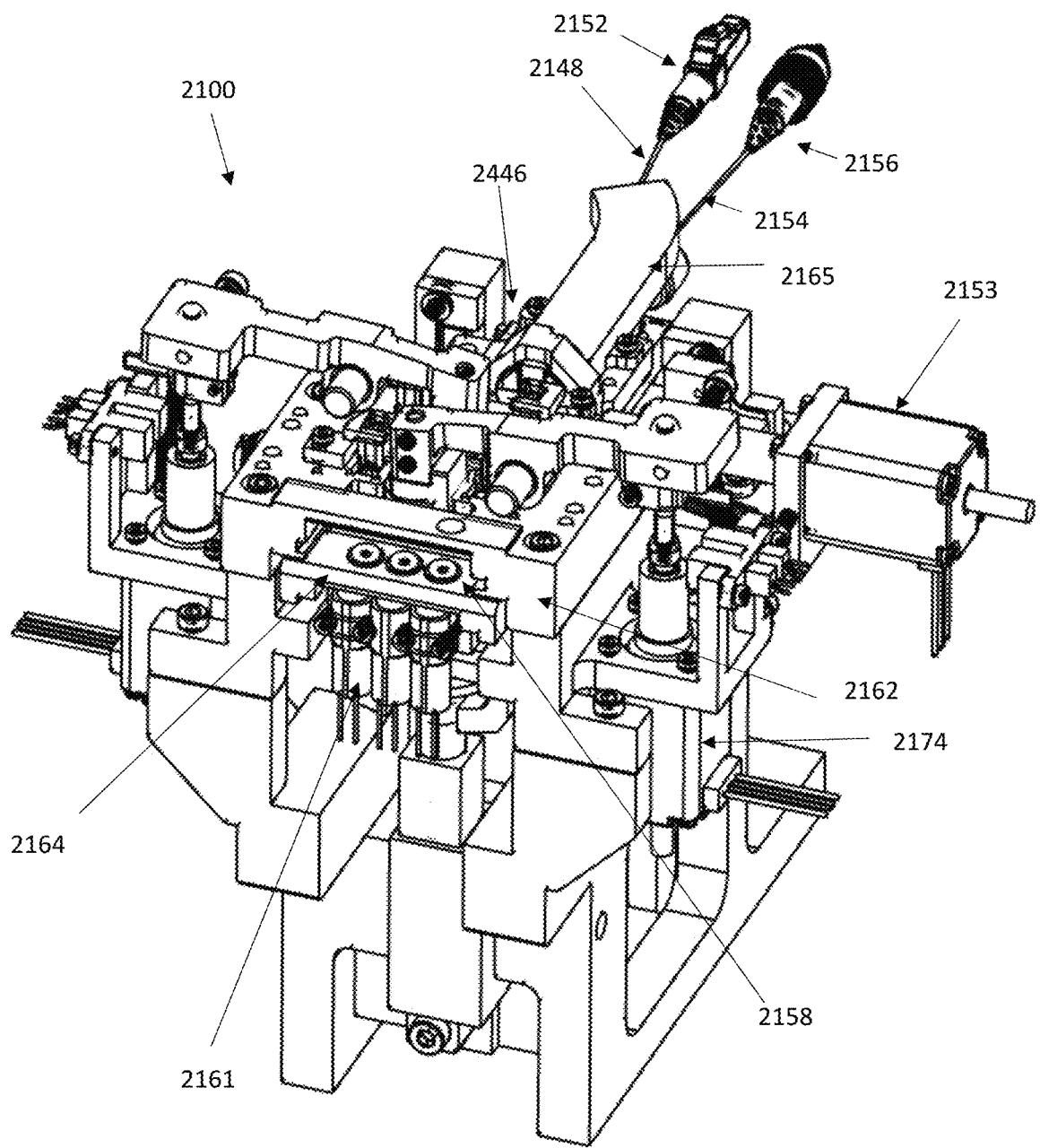
FIG. 21E shows the reader of FIG. 21D, without the cartridge, showing the slot of the cartridge holder.
Figure 21F:
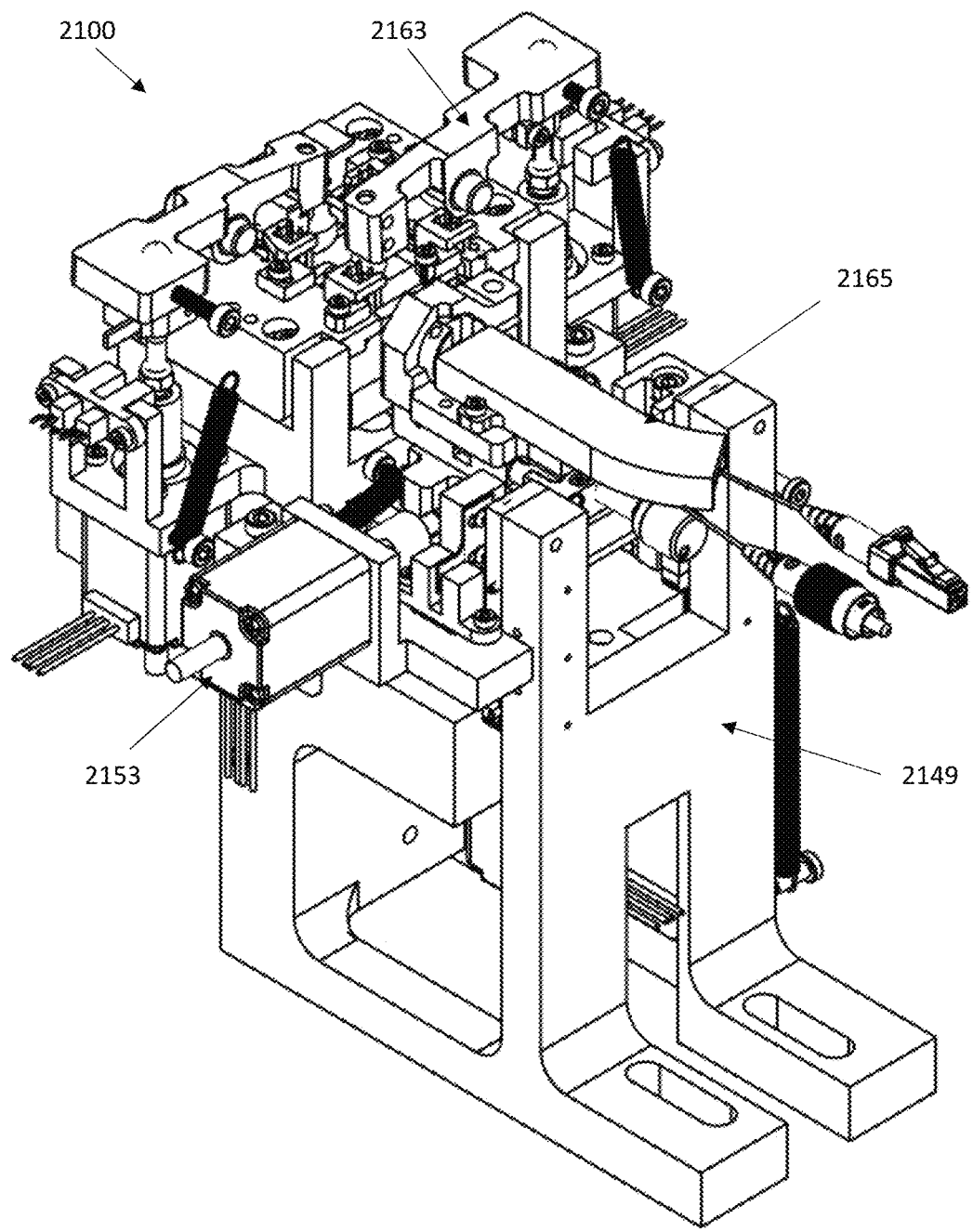
FIG. 21F is a back perspective view of the reader device shown in FIG. 21D.

FIG. 21F shows a back perspective view of the device of FIGS. 21D-21E. The cartridge holder, actuators and imaging sub-systems may be supported on a frame 2149.

Figure 21G:
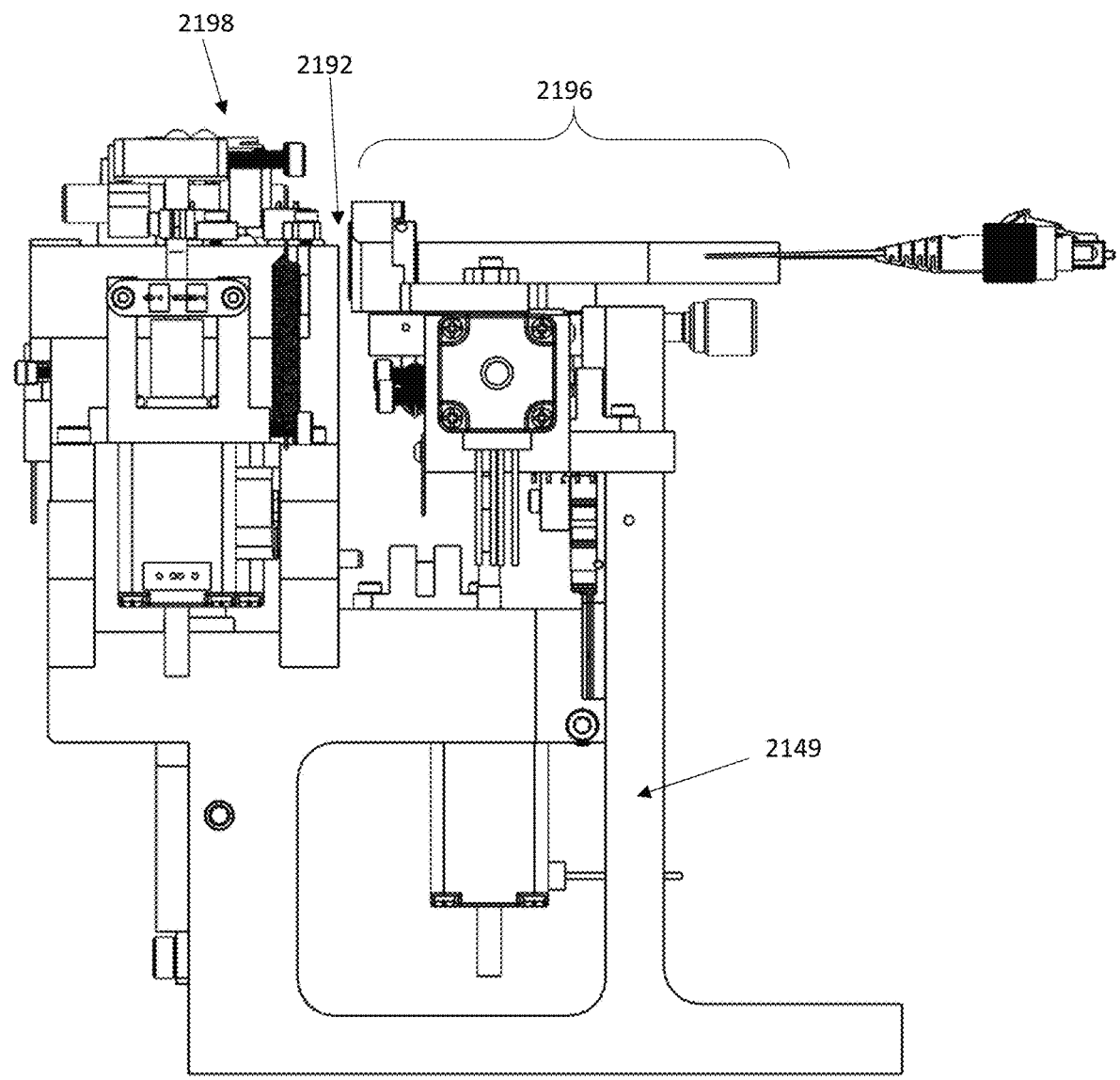
FIG. 21G is a side view of the reader device example shown in FIG. 21D.

FIG. 21G shows a side view of the device of FIGS. 21D-21F, showing the gap 2192 between the imaging sub-assembly 2196 (including the scan head, fibers, light source, detectors), and the holder sub-assembly 2198 (and therefore a cartridge and photonics chip held by the cartridge holder). As described above, the controller may move the scan head to align the fiber ends on the scan head for emitting and receiving light from the chip with the waveguides on the chip.

Figure 21H:
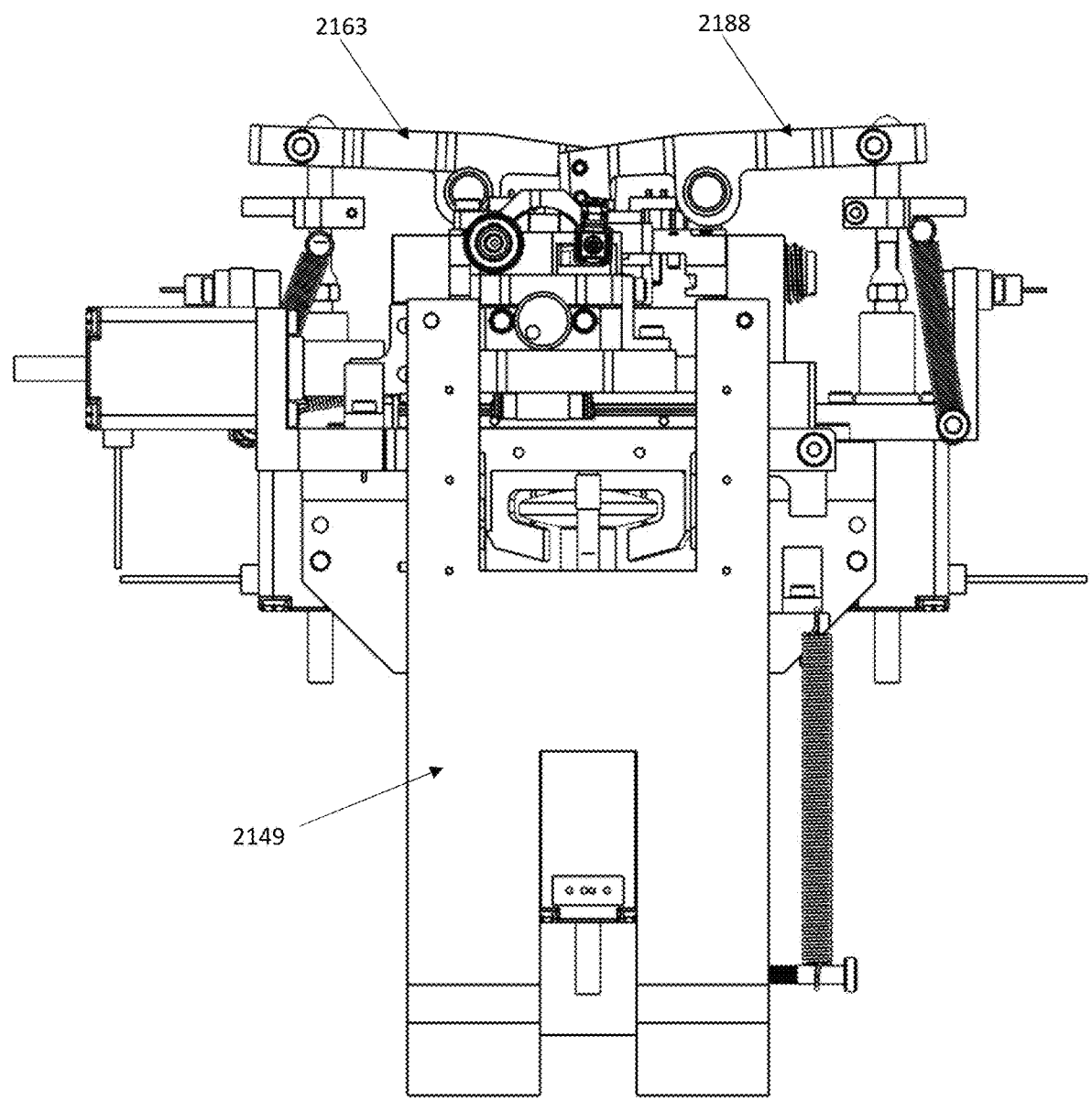
FIG. 21H is a back view of the reader device example shown in FIG. 21D.
Figure 21I:
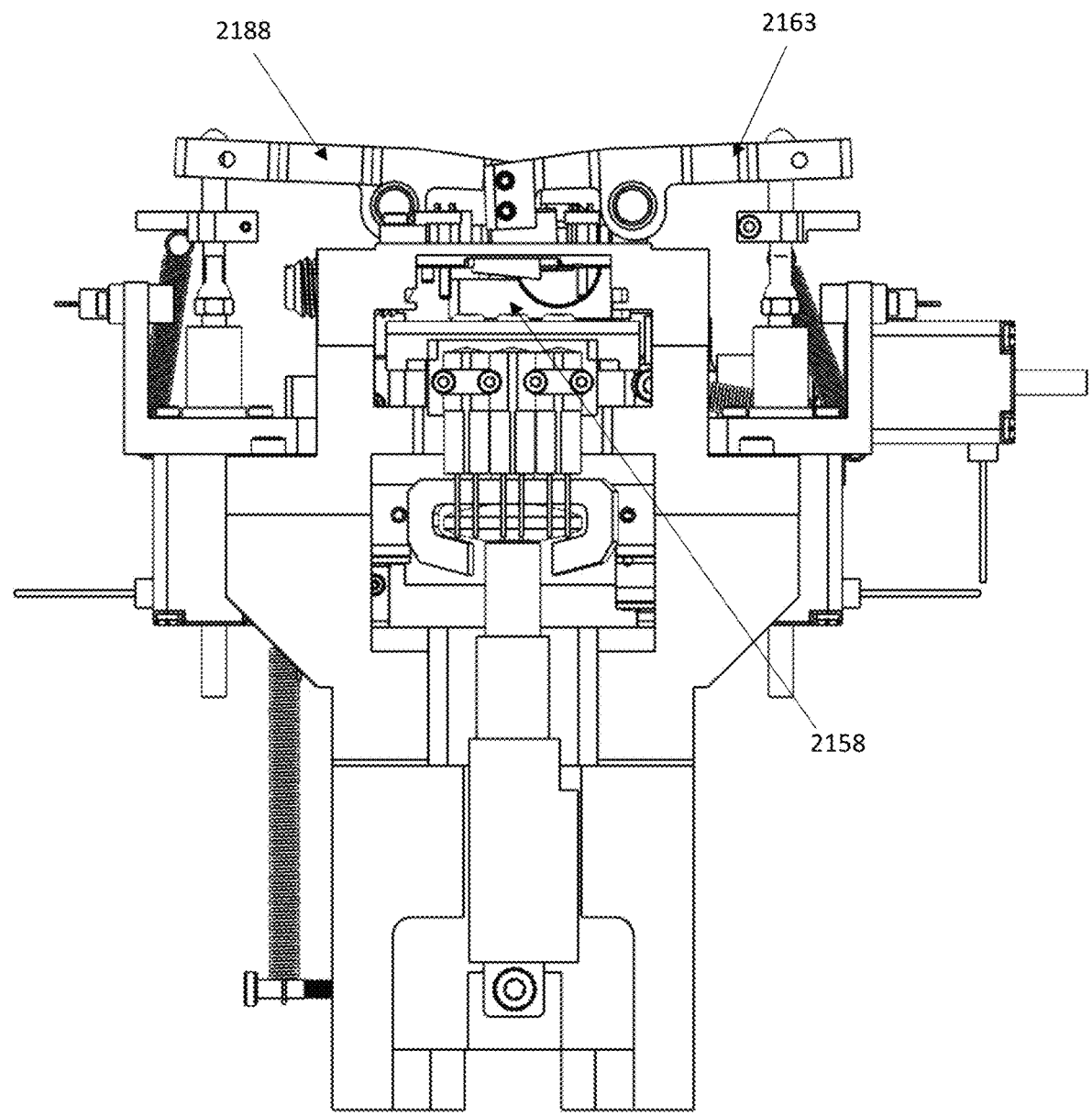
FIG. 21I is a front view of the reader device example shown in FIG. 21D.
Figure 21J:
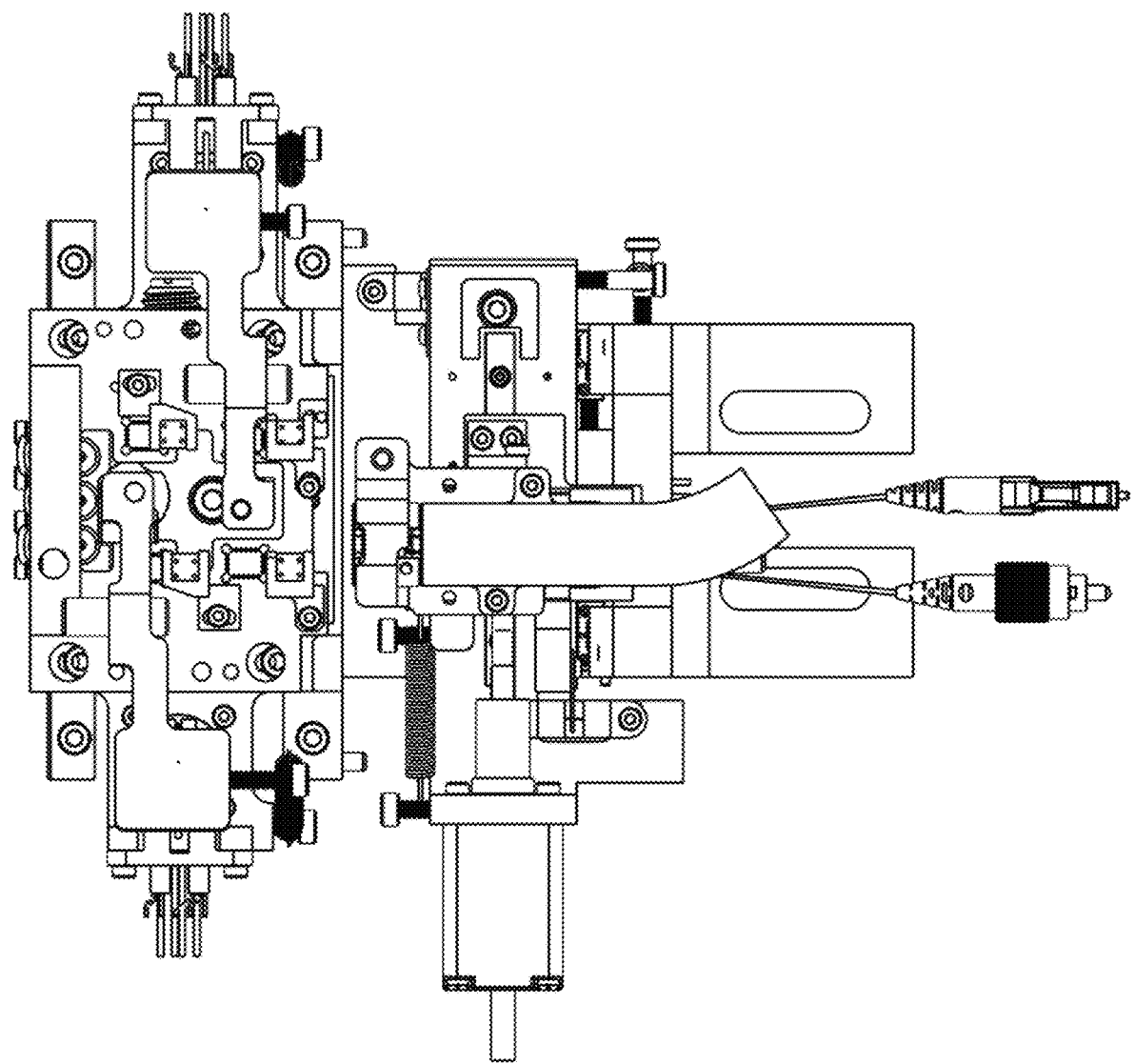
FIG. 21J is a top view of the reader device example shown in FIG. 21D.
Figure 21K:
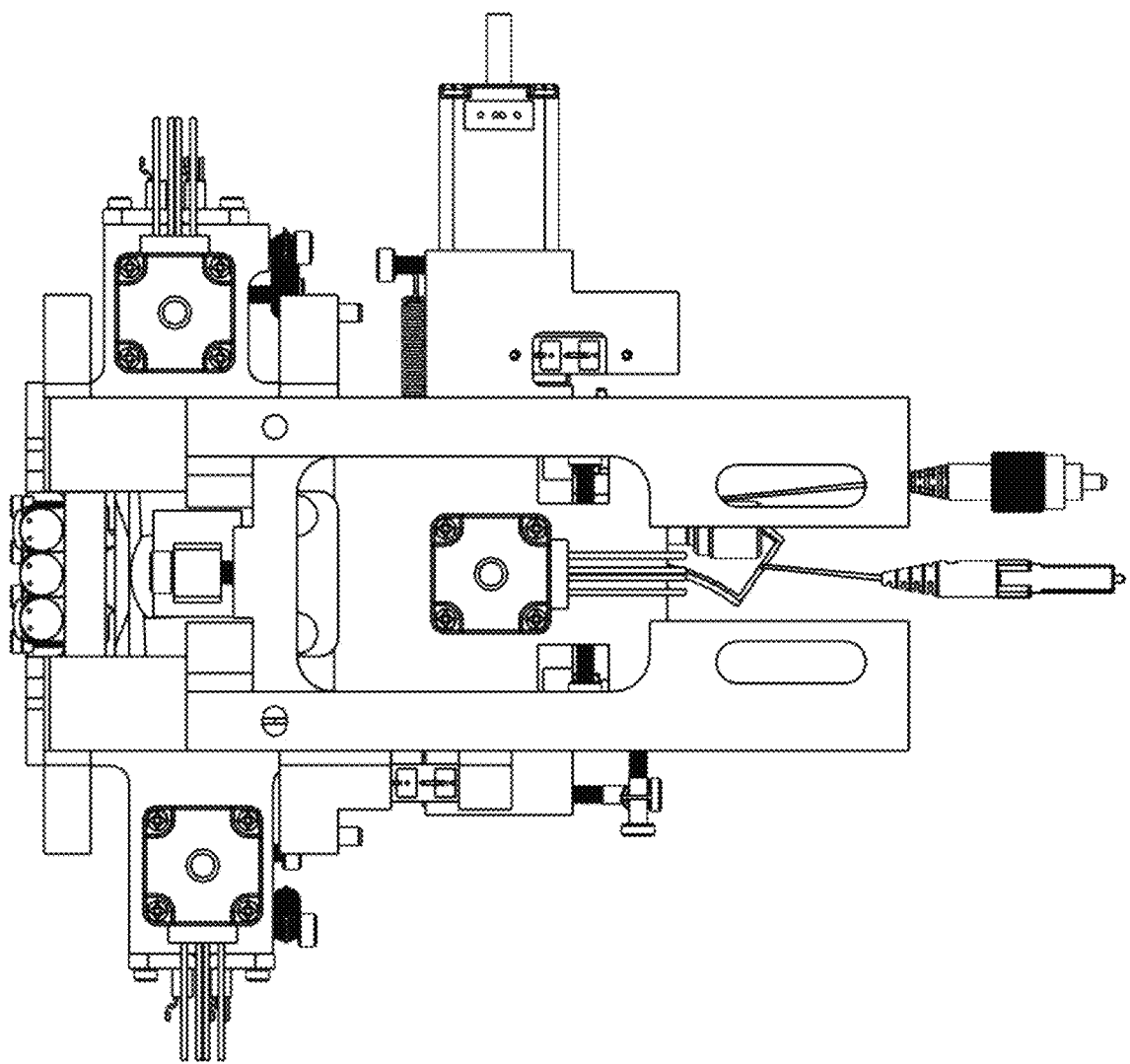
FIG. 21K is a back view of the reader device example shown in FIG. 21D.
Figure 21L:
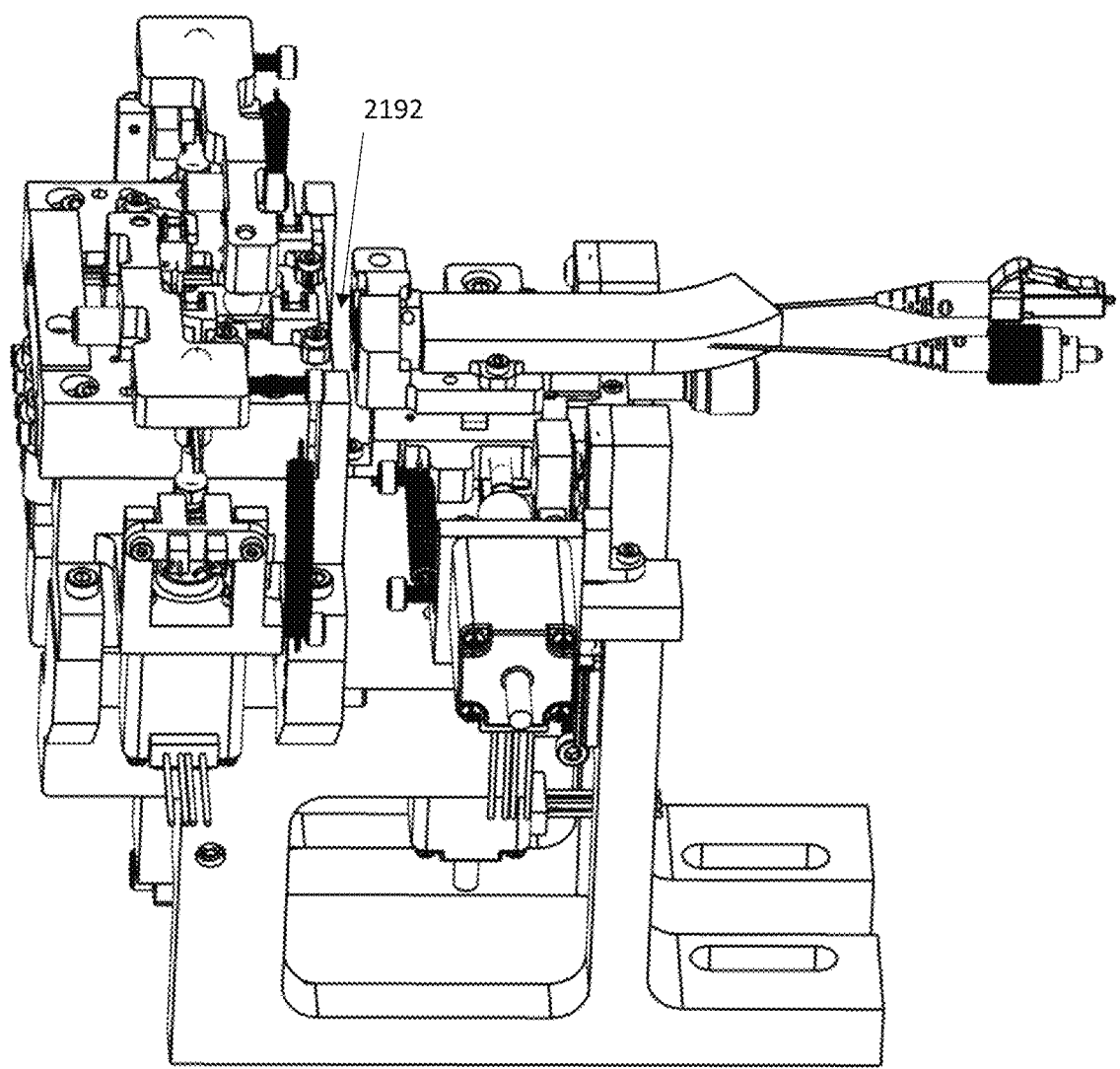
FIG. 21L is a side perspective view of an example of a reader device, showing the gap between the scan head assembly and the back of a cartridge when the cartridge is held in the cartridge holder.
Figure 21M:
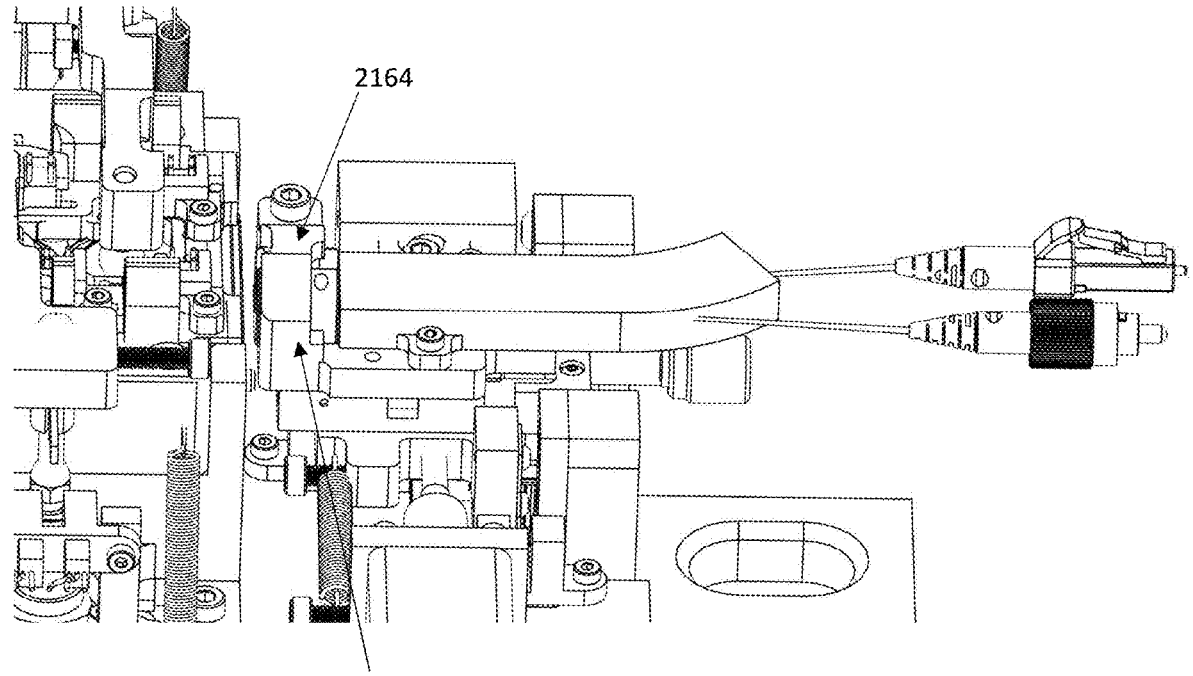
FIG. 21M is a closer view of the reader device, showing the back of a cartridge (held in the cartridge holder), the gap, and the scan head assembly.
Figure 21N:
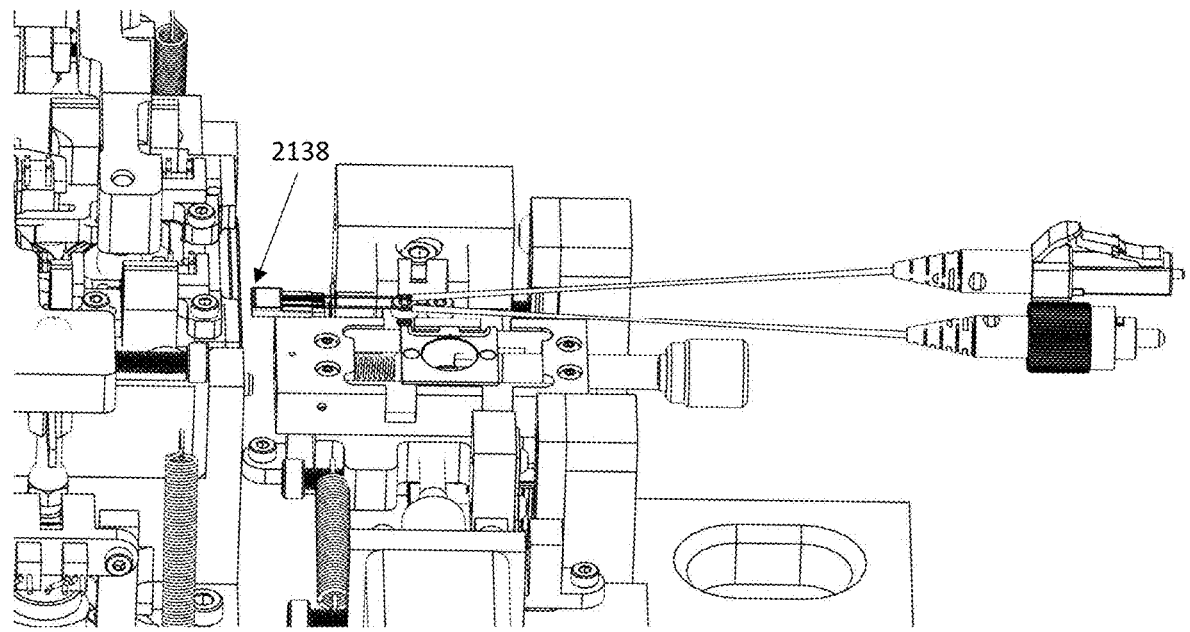
FIG. 21N is another view of the close-up shown in FIG. 21M, with the cover and fiber guide of the scan assembly removed, showing a portion of the scan head where the plurality of fibers connected to the light sources (laser diodes) and sensors (photodetectors) end, across the alignment gap from the photonics ship of the cartridge when a cartridge is held by the cartridge holder.

FIGS. 21H and 21I show back and front views, respectively, of the same device shown in FIGS. 21D-21G. FIGS. 21J and 21K show top and bottom views, respectively. FIG. 21L shows another example of a side perspective view of the device of FIGS. 21D-21K, showing the gap 2192 between the scan head and the cartridge chip when the cartridge is held by the cartridge holder. FIGS. 21M and 21N show an enlarged view of the gap; in FIG. 21N the outer portions of the scan head (e.g., an upper scan head mount 2134 and a lower scan head mount 2136, present in FIG. 21M) removed to show the ends of the fibers 2138 held on the gap-facing side of the scan head.

Optical Path Polarization

Any of the reader apparatuses (e.g., optical readers) described herein may be configured to control the polarization of the light for signal detection to a cartridge's photonics chip and/or received from photonics chip.

First generation hardware of the reader did not utilize any polarization maintaining hardware. This lead to high variability of optical characteristics from one apparatus to another. After ruling out mechanical variances as the root cause of the machine to machine variability, EM simulations were performed for the photonic chip architecture of our system. See FIG. 1.

Figure 22:
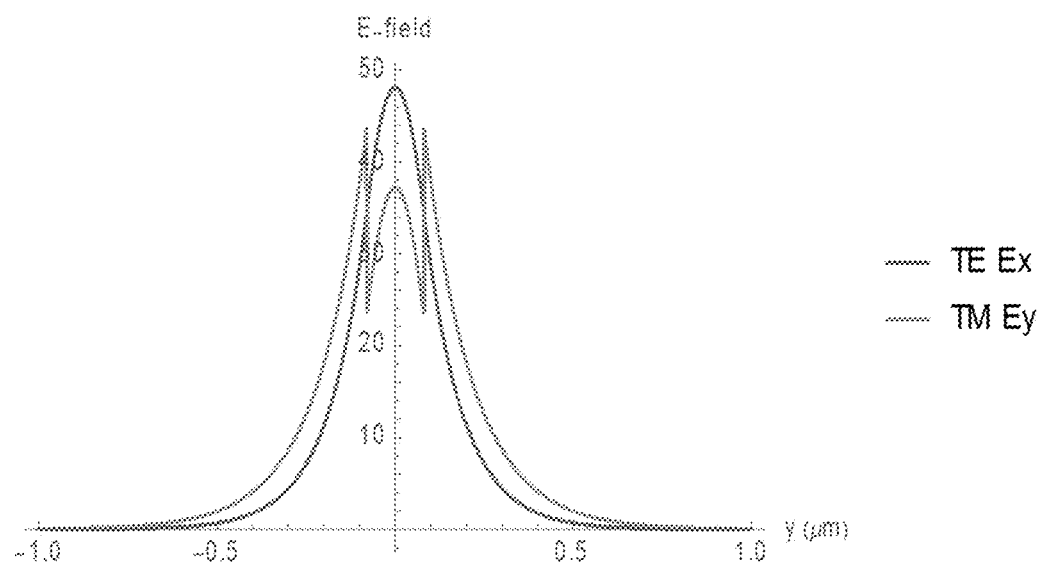
FIG. 22 shows an example of an electric field mode profile for photonic chip waveguides.
Figure 23:
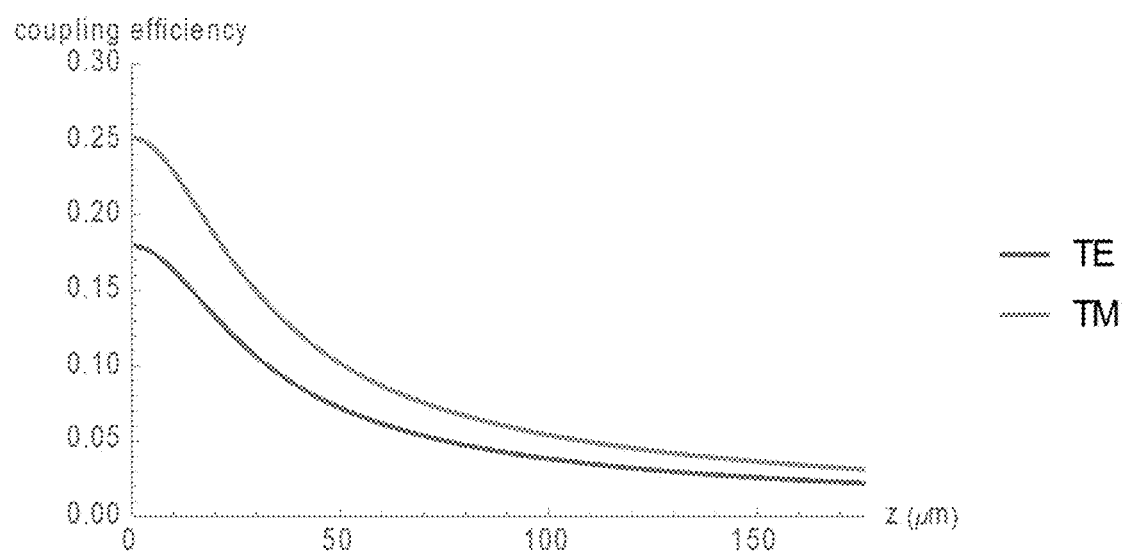
FIG. 23 shows input coupling efficiency for TE and TM modes.

FIG. 22 is a graph showing field mode profiles for an optical reader (such as the optical readers discussed and illustrated above) in which both transverse-electric (TE) polarization (also referred to as S polarization) and transverse-magnetic (TM) polarization (also referred to a P polarization) are compared. In FIG. 22, the electric field mode profiles of the two orthogonal modes of the waveguide are quite different, e.g., the input coupling efficiency is different. The coupling efficiency to each of the two modes is given by the mode overlap integral with the input Gaussian beam from the scan head fiber. FIG. 23 shows a TM mode coupling that is significantly greater than the TE mode coupling efficiency in the tested optical reader apparatus. This demonstrates a large variation in reader optical characteristics if coupled into TE mode vs TM mode, as this would result in different amounts of light into the system for a given laser output.

Figure 24:
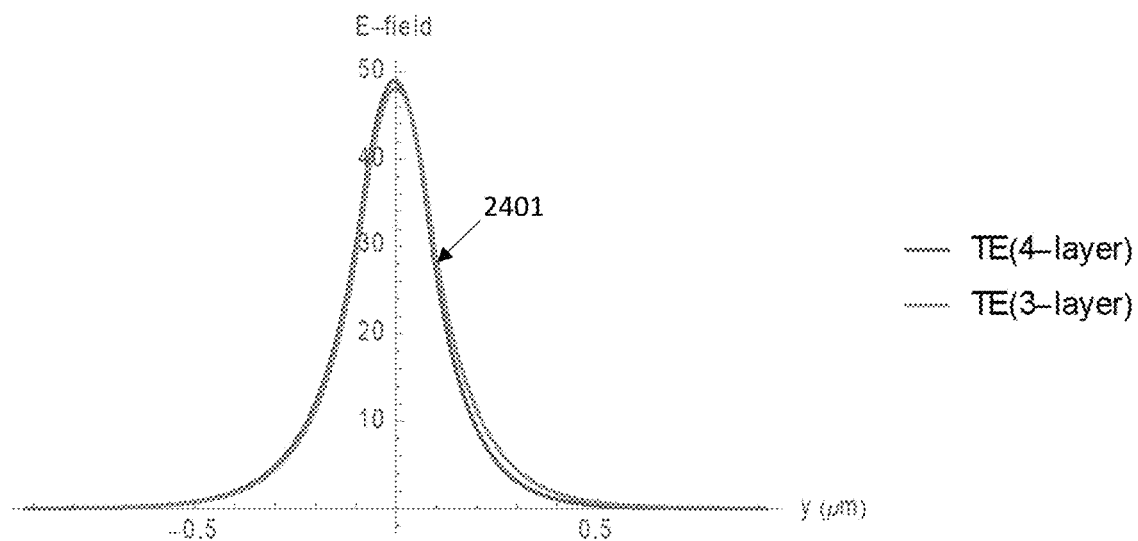
FIG. 24 shows normalized electric field of TE modes at the 3-layer/4-layer (wet) interface.
Figure 25:
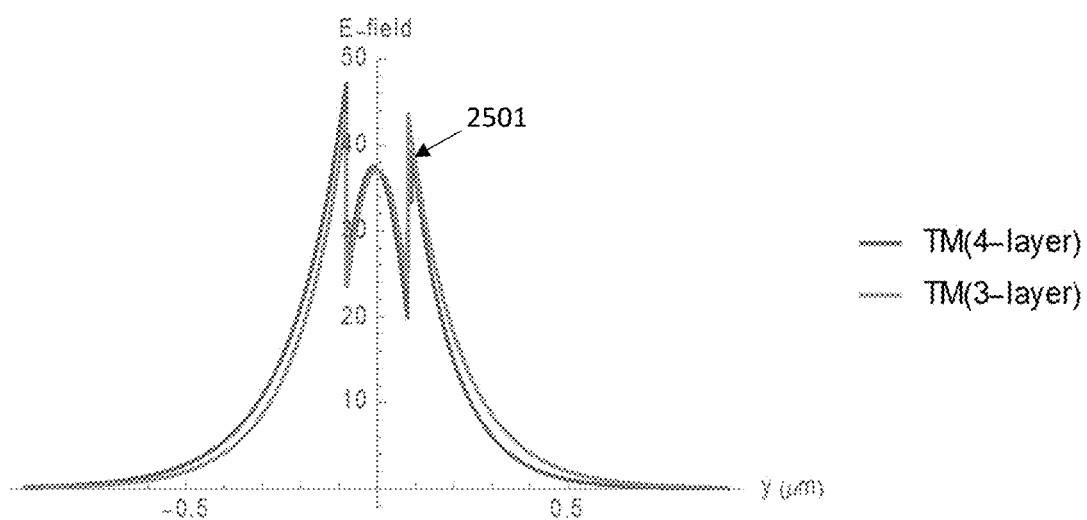
FIG. 25 shows normalized electric field of TM modes at the 3-layer/4-layer (wet) interface.

In addition to the significant difference of input coupling efficiency, there is also a large difference at the well interfaces of the coupling to fluorophore, e.g., in the photonic chip(s) of the cartridge(s) being read by the optical reader. The fluorophore absorbed energy is proportional to the square of the electric field at that point in space. FIGS. 24 and 25 show the electric field profiles for the two orthogonal TE and TM modes in various configurations of the waveguide (e.g., a four layer waveguide configuration and a three-layer waveguide configuration). In any of the tested configurations, at the well surface where the fluorophore will sit ($\approx$100 nm), the TM mode has a large spike 2501 and its magnitude is significantly larger than the value 2401 at the surface for the TE mode.

Figure 26A:
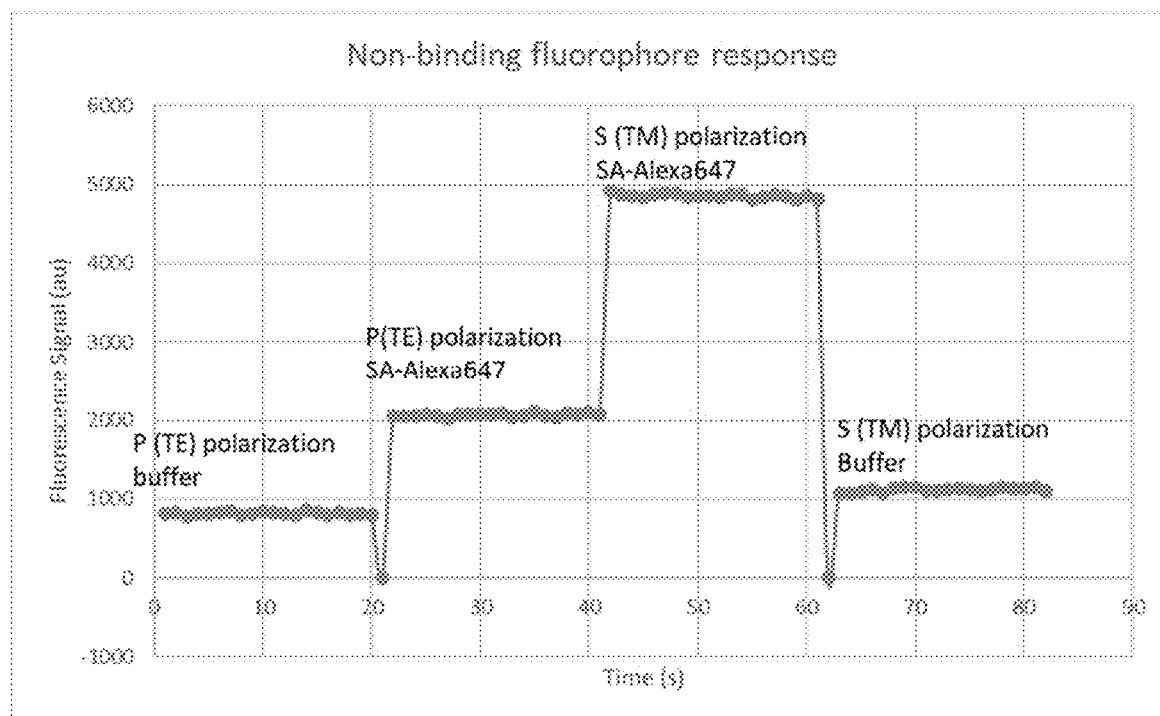
FIG. 26A shows the results of an optical jump experiment for TE and TM polarization modes.

An optical experiment was used to experimentally test these simulation results. Using free space optics, the linear polarization state of light that is outputted from the scan head was controlled. Using a fixed laser power, an optical jump experiment was performed with the optical polarization being TE and also TM. As shown in FIG. 26A, TM polarization had a factor of 2.5× better signal compared to the TE mode for the same laser power.

The simulation and experimental results such as those described above, illustrate the surprising polarization sensitivity of the optical reader system(s) and cartridge(s), e.g. photonic chips. In particular, the configuration of the optical readers and cartridge chips described herein respond surprisingly well to the use of TM (e.g., S) polarized light for both excitation and detection. Thus, in any of the apparatuses described herein, the optical path may be configured to maintain a known polarization (e.g., TM polarization) throughout. This may be done by the use of polarization-maintaining fibers pigtailed onto diode lasers and also using polarization-maintaining fibers in the newly designed scan head in general. The polarization axis of our optical system may be configured to optimally interface with the photonic chip using the TM mode.

Figure 26B:
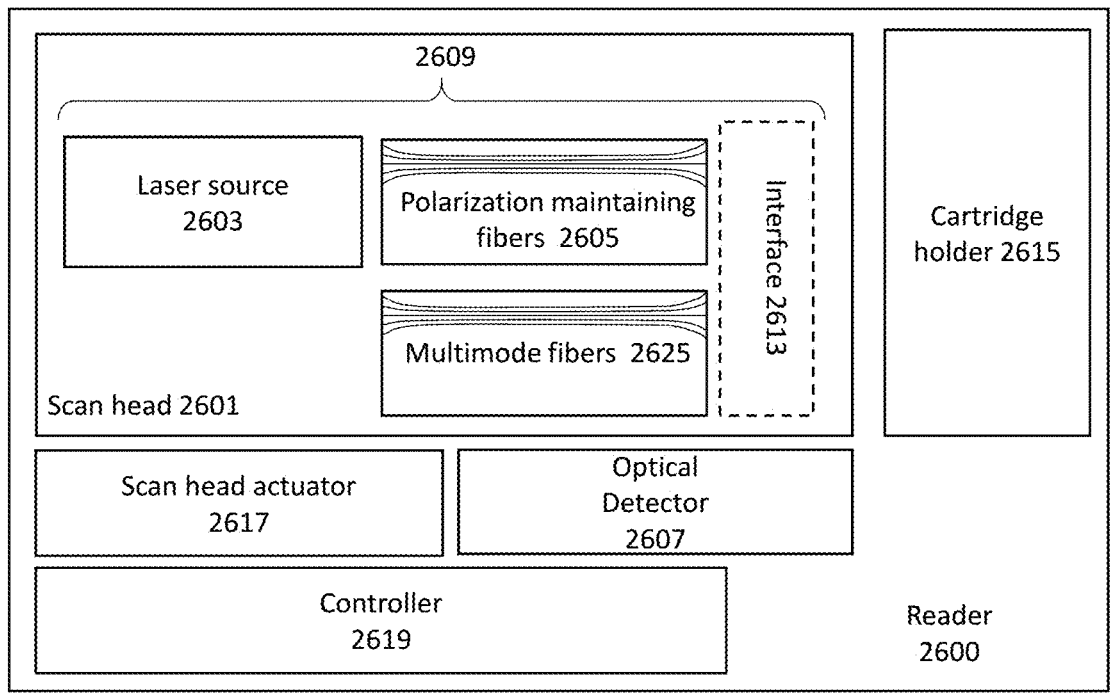
FIG. 26B is an example of one variation of a schematic of an optical reader as described herein.

FIG. 26B illustrates one example of an optical reader apparatus 2600 including a scan head 2601, a scan head actuator 2617, a controller 2619 and a cartridge holder 2615. The scan head may be aligned with a cartridge (e.g., the edge of a photonics chip in the cartridge) both to permit the one (or in some cases a plurality of parallel) excitation beam(s) that are emitted by the scan head to be properly centered on the edge region of the chip so that light may pass into the chip to enter into the one or more waveguides of the chip. As described herein, when the photonics chip includes a plurality of parallel waveguides that are arranged in an array in which excitation row are crossed by detection rows (see, e.g., FIGS. 8A and 8B), so that evanescent transmission may be detected in the detection row(s), the polarization of the light may be critical and should be controlled as described herein. Thus, any of these apparatuses may be configured to control the polarization of the light applied and received by the apparatus, and particularly so that the apparatus may emit and in some variations receive, TM polarization.

Figure 26C:
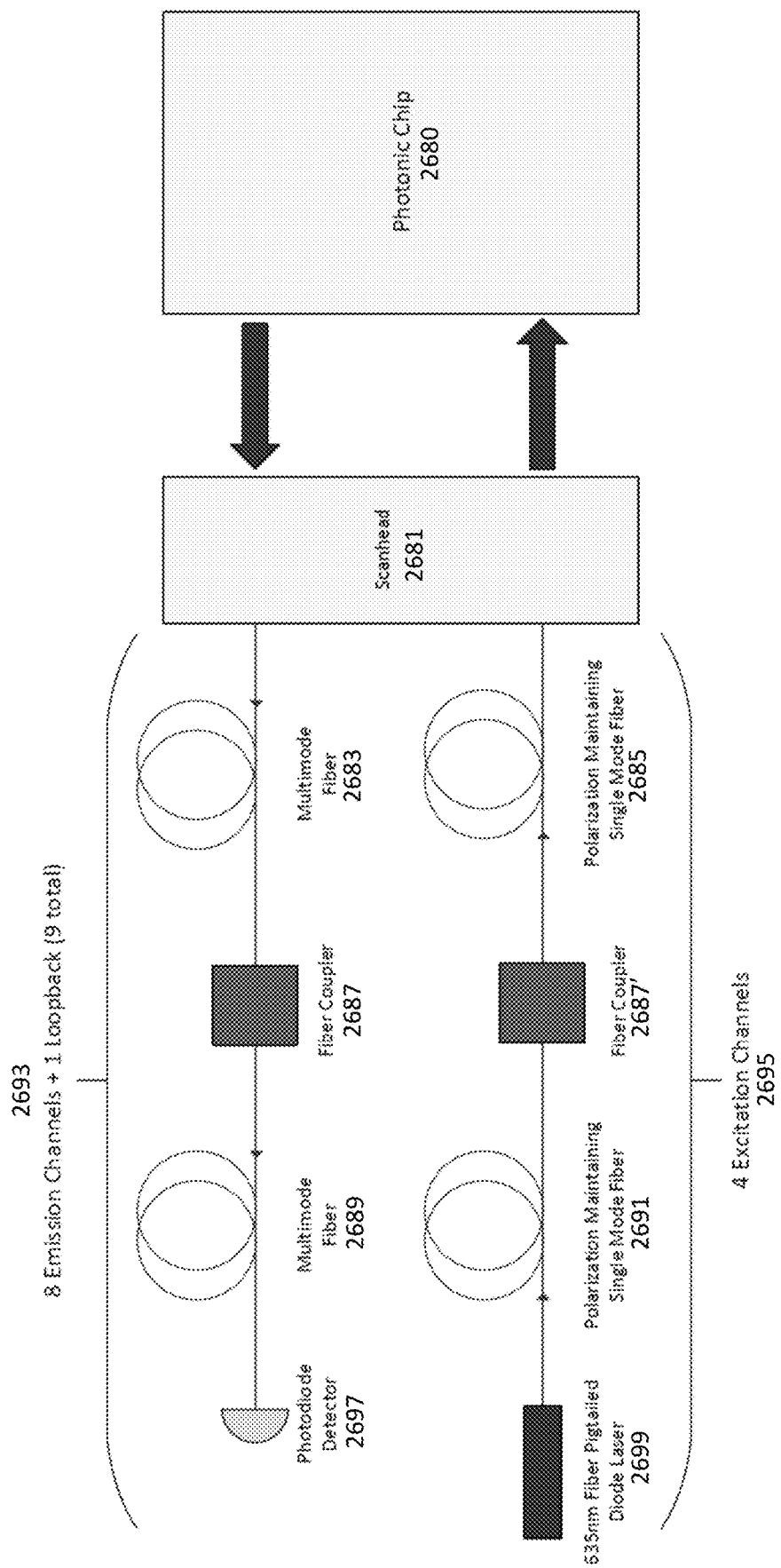
FIG. 26C is an example of a variation of a schematic for an optical reader as described herein.

For example, in FIG. 25B, the laser light source 2603, transmission fibers 2605 and scan head 2601 may form a polarization axis 2609 that is configured to maintain the TM polarization of light transmitted by the system so as to optimally match the polarization of a photonics chip (e.g., including an array of intersecting waveguides) that permit evanescent light transmission. In some variations the scan head may include a laser light source 2603 to which a plurality of polarization-maintaining fibers 2605 are connected. Alternatively, as shown in FIG. 26C, the laser source (e.g., LEDs) may be separate from the scan head and may be coupled to the scan head through the polarization maintaining fibers. Both the laser source and the polarization maintaining fibers may be configured so that they are matched in polarity (e.g. TM polarization) with the photonic chip. The scan head may also include or be connected to the optical detector 2607 via a plurality of multimodal fibers 2525. In some variations the scan head includes an interface 2613 that holds the ends of the fibers (e.g., the polarization maintaining fibers and/or the multimodal fibers) in an arrangement that matches the arrangement of the waveguides (the emission and excitation waveguides) in the photonics chip. The optical detector(s) (e.g., photodiode detector(s)) may be arranged as an array of sensors that detect signal(s) from the photonics chip when properly aligned, concurrent with excitation. In some variations, any portion of the scan head may include a polarizer (e.g., a TM polarizer) to remove or redirect TE polarized light so that the scan head may be positioned by moving the scan hear relative to the interface edge of a chip (or chips) on a cartridge held in a cartridge reader. For example, in some variations a polarizer may be between the optical sensor and/or the cartridge once it is loaded in to the cartridge structure. Alternatively or additionally, a polarizer (e.g., TM polarizer) may be positioned in front of the optical sensor(s), e.g., between the optical sensor(s) and the fibers 2605; and/or between the laser source and the plurality of fibers.

The scan head may also include one or more lenses, filters, and/or other optical elements. For example, each optical fiber end may terminate in a lens or lensing element. The ends of the fibers may be arranged in a pattern configured to match the pattern of emission and detection waveguides ends in the photonic chip edge. For example, the optical fiber ends may be arranged in a line, and individual fiber ends (and/or groups of fibers, such as emission and detection fibers) may be separated by the same distances as the waveguides in the chip (see, e.g., FIGS. 8A-8B).

In some variations, the apparatus may be configured to adjust the polarization of the system before or during the assessment of analyte signals. For example, the controller 2619 of the apparatus may be configured to adjust the position of all of the scan head or a portion of the scan head (e.g., the interface 2613, also referred to as a cartridge interface) relative to the edge of the chip in the cartridge holder 2615. The position may be adjusted in x, y, z and/or angle (e.g., pitch, yaw, and/or roll) relative to the cartridge holder.

FIG. 26C shows another example of a schematic of a portion of an optical reader apparatus for detecting evanescent signals from a photonic chip 2680. In FIG. 26C, the optical reader apparatus includes a scan head 2681 that may be moved within the optical reader relative to the photonic chip in order to pair with the excitation-receiving waveguides (e.g., four excitation receiving waveguides such as those shown in FIGS. 8A-8B). The photonic chip is oriented so that the waveguides for both excitation and detection have ends that are arranged along an edge of the chip, and this configuration of waveguides has an optimal polarization that is TM polarized. The polarization of the chip is matched by the polarization of both the light source (e.g., laser diodes 2699) and the light path from the laser diodes to the photonics chip (including a plurality of polarization-maintaining single mode fibers 2691, 2685 and fiber coupler(s) 2687'. Each excitation waveguide may match with a TM polarized light path extending from an individual diode laser (e.g., a 635 nm fiber pigtailed diode laser) and may couple via a polarization maintaining single mode fiber and fiber coupler to the scan head. The return (sensing) path may include a plurality of photodiode detectors 2697 that couple to the scan head via a plurality of multimode fibers 2683, 2689 and fiber couplers 2689. Each emission/sensing waveguide may couple to an individual photodiode detector.

In some variations the angle of polarization may be matched within +/−a few degrees (e.g., 30 degrees, 25 degrees, 20 degrees, 15 degrees, 10 degrees 5 degrees, 2 degrees, 1 degree, etc.).

Precision Alignment of the Cartridge

Any of the apparatuses described herein may also or alternatively be configured to control the precise alignment between the cartridge and a scan head. In particular, a cartridge holder may be configured to securely but releasably and repeatably holding a cartridge so that the edge of the photonics chip, on which a detection reaction (such as those described above) may be sensed. Alignment may be particularly important between the scan head and a cartridge held within the reader. Although the reader should allow some tolerance when inserting a cartridge, so that the cartridge may be easily inserted and reliably read, the distance and orientation between the scan head and the photonic chip may be precisely controlled to allow rapid and accurate reading of the cartridge. In addition, the actuation of the fluidics in the cartridge (e.g., valves and membrane pump) may be aligned in order to allow the device to be operated reliably. Described herein are methods and apparatuses for coupling a cartridge having fluidic components (e.g., valves, membrane pump, etc.) and one or more photonic chips so that these components of the cartridge are aligned with the corresponding components of the reader.

FIGS. 27-42 illustrate examples of optical readers that include a cartridge holder (clamp) that is configured to hold the cartridge securely and precisely aligned with the scan head. In general, the apparatuses described herein may be configured to automatically adjust the alignment between the scan head and the cartridge, particularly an edge of one or more photonics chip of the cartridge. Thus, described herein are methods and apparatuses for holding a sample-collecting cartridge that include a clamp that is particularly configured to permit robust use, so that even after repeated use with different cartridges, subsequent use may still result in precise positioning and alignment between the scan head and the cartridge.

Figure 27:
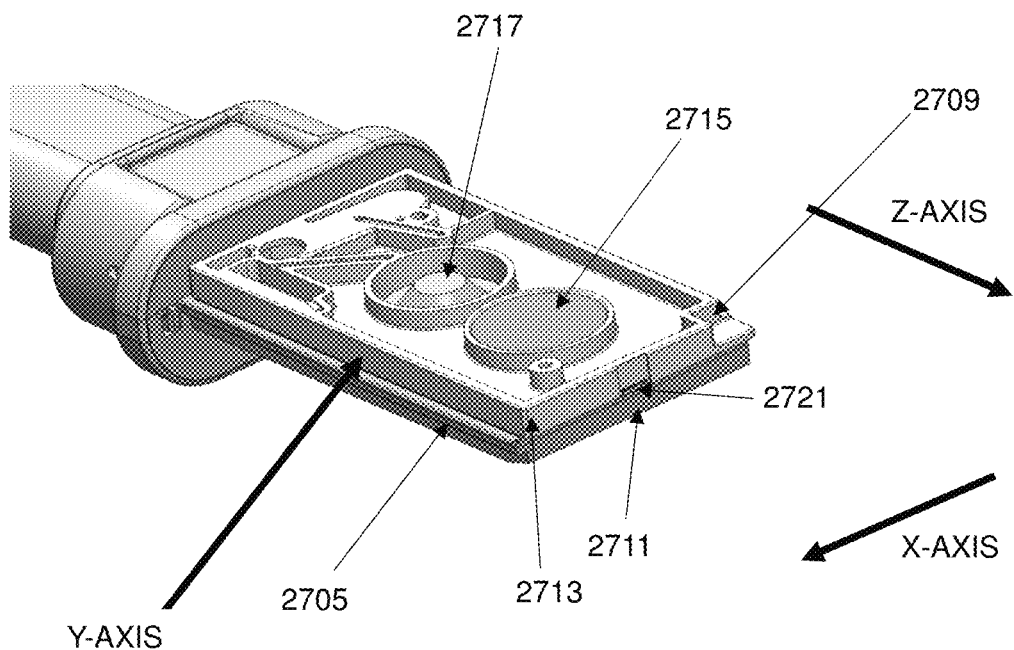
FIG. 27 is an example of a cartridge as described herein.

The cartridge may be inserted into the optical reader by inserting into a cartridge interface 2105 (e.g., an opening, lid, tray slot, etc.) in the reader. Once the cartridge is inserted into the cartridge interface it may be clamped into position. Clamping may be automatic or manual. In some variations the apparatus detects insertion of a cartridge and clamps onto the cartridge. Thus, the cartridge interface may open into a cartridge holder that may include a clamping interface (e.g., an opening an open clamp). In some variations, the apparatus includes a clamp housing (e.g., the cartridge holder includes a clamp housing) that has one or more slots cut into the side of the clamp housing; the cartridge may have wings or other mating features (pins, rails, etc.) that mate with the slots. See, e.g., FIG. 27, showing one example of an end region of a cartridge including at least one wing 2705 and a cut-out region for a wing 2709 on the cartridge. When engaging with the optical reader, a cartridge such as the one shown in FIG. 27 may be pushed forward (showing as the Z-axis, corresponding to a long axis of the cartridge in this example) until a reference surface 2711 on or near the front of the cartridge (e.g., the reference surface in the x axis 2711 and/or the reference surface in the y axis 2713) hits a cylindrical surface of a reference pin in the reader and stops.

The device may also include an output (e.g., display, screen, etc., including a touchscreen) 2169 and/or an input (e.g., in FIG. 21A-21B, a touchscreen).

In some variations, the clamp securing the cartridge includes a ball plunger on one side of the clamp housing which pushes against one of the wings (in the X-axis) that extend from the side of the cartridge. This wing has a cut out at a certain location such that when the cartridge is all the way in the clamp the ball plunger pushes the cartridge wall up against two reference surfaces (e.g., against the Z-Axis and X-Axis). The reference surface in the Z-axis may be a pin that is part of the clamp housing. Another reference surface may be the wall of the top clamp housing opposite the ball plunger. The ball plunger may keep a constant force on the cartridge while it is fully inserted. While the cartridge is fully inserted, the clamp base can be raised (Y-axis) which forces the cartridge up against the third reference surface (e.g., the underside of the top of the clamp) and may hold the cartridge precisely and securely in place during usage.

As discussed above, there may be an optical chip in the cartridge which is optically scanned. The location of the front surface of this chip may be precisely placed in the X-Y-Z-axis. The back of the chip in the Z-Axis may be placed in contact with a reference wall in the top front of the cartridge.

Figure 39:
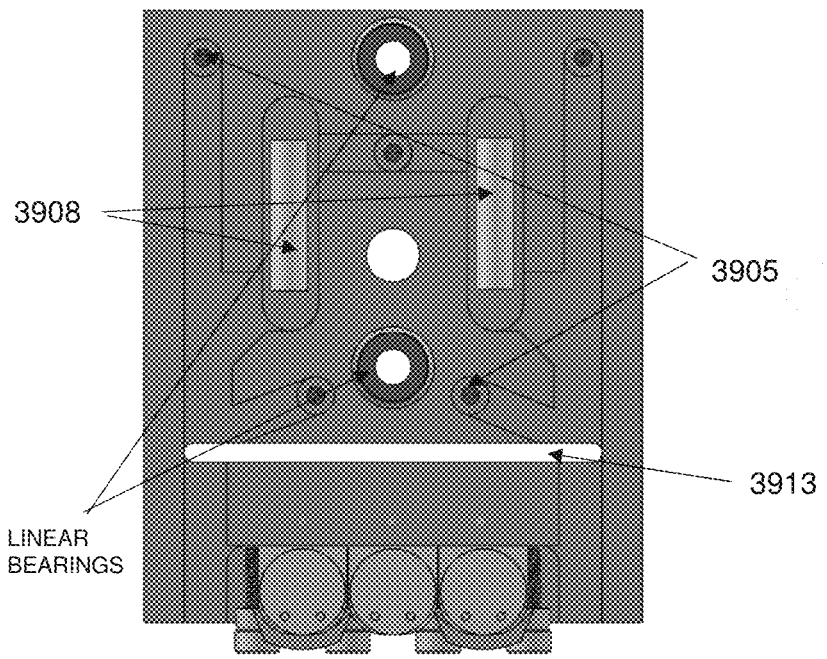
FIG. 39 is illustrates one portion of a cartridge holder of a reader, showing thermal regulation (and feedback) that may be helpful

In any of these variations, the cartridge holder (e.g., the clamp base) is temperature controlled. Temperature control may allow the cartridge to be maintained at a constant temperature and/or may allow the cartridge temperature (all or a local region of the cartridge) to be adjusted. For example, FIG. 39 illustrates one example of a cartridge holder portion of a reader apparatus that is configured to control the temperature. In FIG. 39, the temperature may be sensed (e.g., the temp of the cartridge) by included two or more temperature sensors 3905 on the cartridge holder in regions facing or in contact with the cartridge. In some variations the cartridge holder may also include one or more heaters 3908. The cartridge and/or the reader may include one or more insulating regions (e.g., thermally insulated regions), For example, in FIG. 39, the cartridge holder includes a partition 3913 (e.g., a material cut or region to help confine heat from another region of the cartridge (e.g., thermally isolating the front part of the clamp (cartridge holder).

The cartridge holder (e.g., the clamp mechanism) may be mechanically and/or electrically and/or pneumatically controlled. For example, the controller in the optical reader may coordinate the operation of the cartridge holder, including one or more of: sensing the cartridge within the cartridge holder, closing/opening the clamp of the cartridge holder, coordinating the application of force in the x, y, and/or z direction to retain and align the cartridge, etc. For example, in some variations the cartridge and the optical reader (e.g., the cartridge holder) may be configured for pneumatic and fluidic operations.

In addition to holding the cartridge in a predetermined manner, for alignment with the optics of the optical reader, the reader, including the cartridge holder, may be aligned so that the controller may coordinate the movement of fluid (microfluidics) within the cartridge, as discussed above. For example, in FIG. 27, a cartridge may include a pump membrane 2715 that may be operated by a pump membrane actuator (e.g., a piston or other member) in the reader to apply positive and/or negative force (e.g., by pushing, holding, or releasing the membrane) within the cartridge. The cartridge may also include one or more blisters 2717 including a fluid, as described above. The controller of the optical reader may further coordinate the release of fluid from the blister. A chip (e.g., photonic chip) 2721 is typically exposed at one end. In FIG. 27, the exposed edge of the chip is located in the middle of the x-axis face about midway through the y-axis face.

Figure 28:
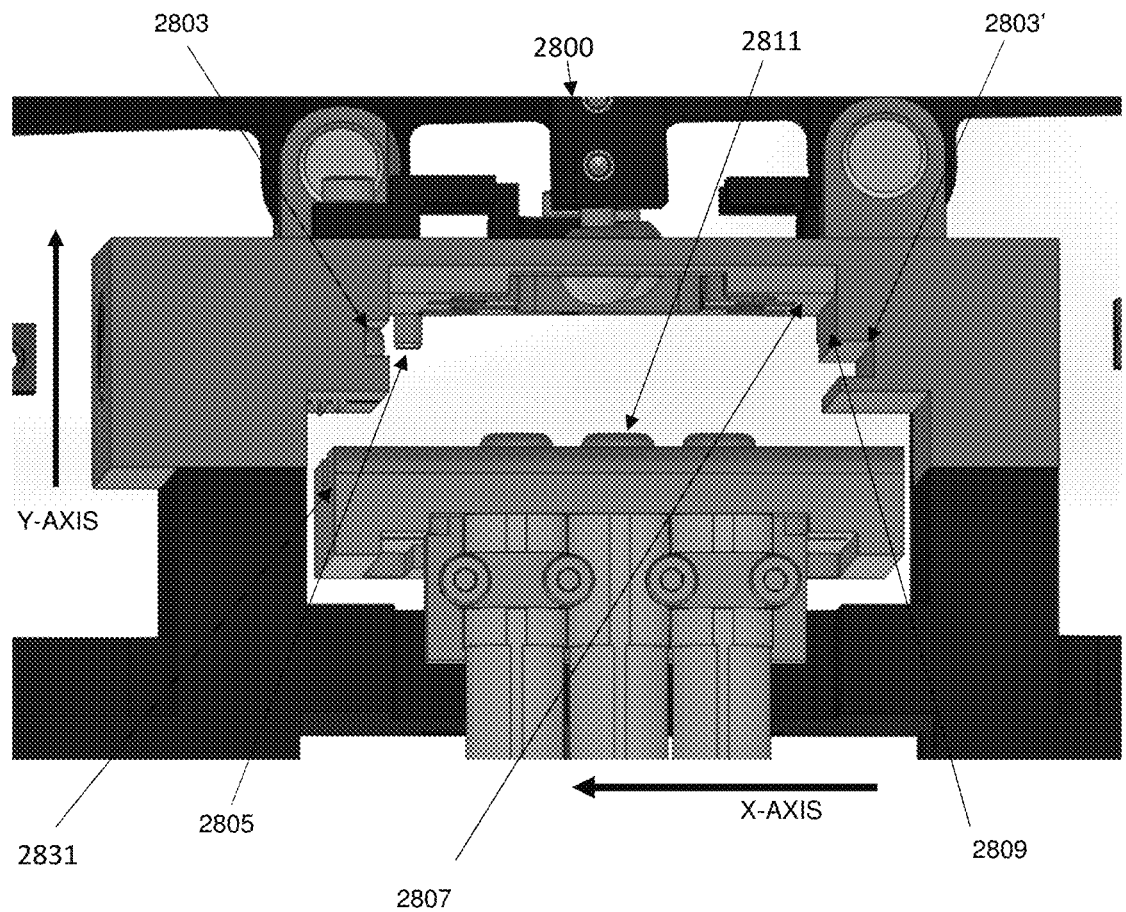
FIG. 28 is a partial cut-away view of one variations of a cartridge holder portion of reader apparatus.

FIG. 28 shows one example of a partial section through a cartridge holder 2800 including a clamping portion. In this example, the cartridge holder includes a cut out slot region 2803, 2803' on either side for engaging wings on the cartridge (extending into the reader from the opening in the reader in the z-axis direction, as shown in FIG. 27). The opening formed for the cartridge in the cartridge holder may also include at least one reference pin 2805 in the z-axis. A reference surface in the y-axis 2807 as well as a reference surface in the x-axis 2809 may assist in alignment in these directions. By choosing and configuring the reference surfaces in the clamp and cartridge, the stack up of tolerances may be minimized. In addition, the ball plunger and movable clamp base 2831 may provide precise and repeatable positioning of the cartridge. FIG. 28 also shows some of the regulator members 2811 (e.g., valve controls) that may open/close air vents in the cartridge to control fluid movement (as described above). Additional regulators (e.g., mechanical regulators, such as pistons, etc.) may be used to apply force to regions of the cartridge to move fluid through the cartridge (e.g., pushing on the membrane(s)).

Figure 29:
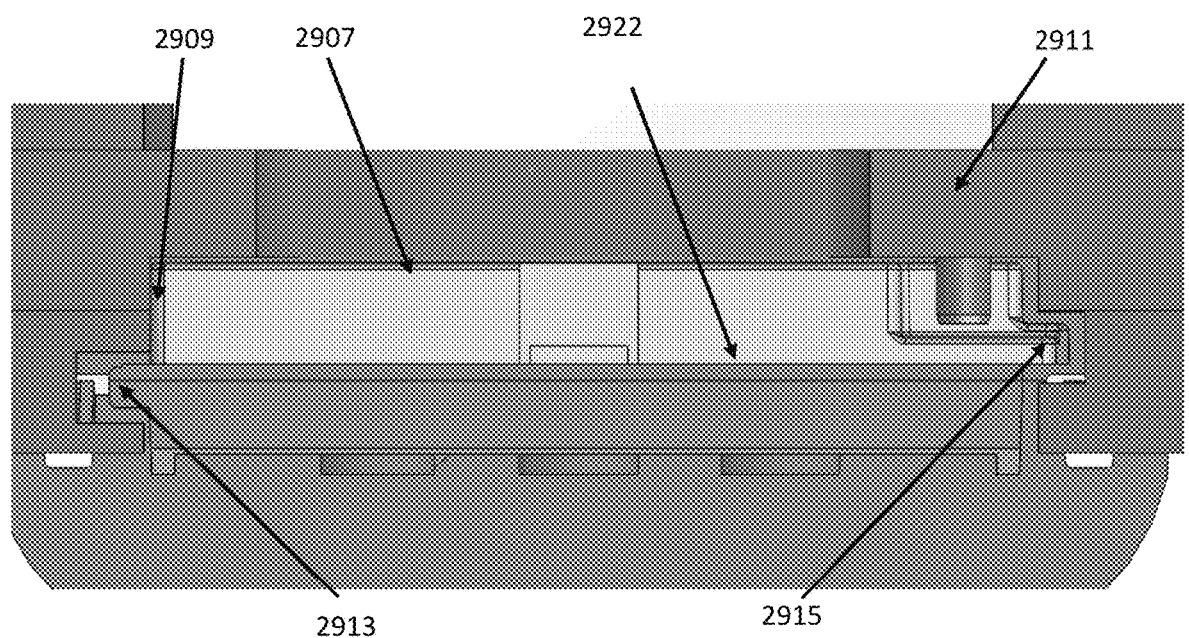
FIG. 29 is an illustration of cartridge holder showing a cartridge within it.

FIG. 29 illustrates an example of a cartridge showing it clamped onto one example of a cartridge 2922. In FIG. 29, the X and Y reference surfaces 2907, 2909 are shown making contact with the corresponding surfaces on the cartridge. The cartridge holder includes a clamp top 2911 that secures the cartridge 2922; wings on the right side 2913 and left side 2915 of the cartridge may engage with slots in the cartridge holder, as shown. The wings may guide the cartridge into the clamp but are not necessary as an alignment feature; by themselves, the wings may not secure the cartridge in position adequately, because they must include tolerance for inserting, removing and sliding the cartridge in/out of the apparatus.

Figure 30:
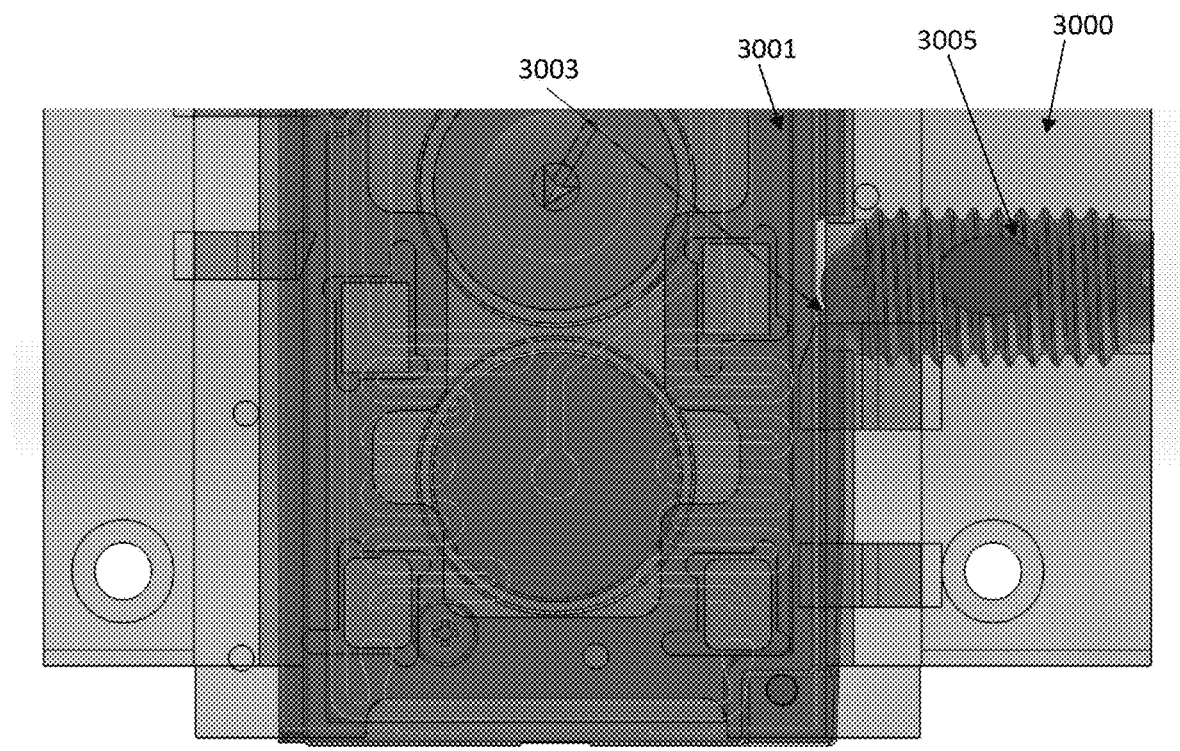
FIG. 30 is another example of a portion of a cartridge holder including a cartridge.

In general, the clamp (e.g., cartridge holder 3000) may include one or more alignment pins, such as one or more ball plungers, that are keyed to provide a force in a predetermined direction to secure the cartridge in the cartridge holder of the reader. For example, FIG. 30 illustrate an example of a ball plunger 3005 that engages with the cartridge 3001. The ball plunger is biased to extend in the x direction; inserting the cartridge into the cartridge holder initially pushes the ball plunger back. As shown in FIG. 30, the ball plunger 3005 (an x- and z-directed ball plunger) may rest on a corner 3003 of the cartridge when the cartridge is fully inserted. The force from the ball plunger is directed in the x and z directions (though the ball plunger moved in the x direction primarily). In this example, the ball plunger engages with a shoulder region of the cartridge about midway along the z-axis of the cartridge.

Figure 31:
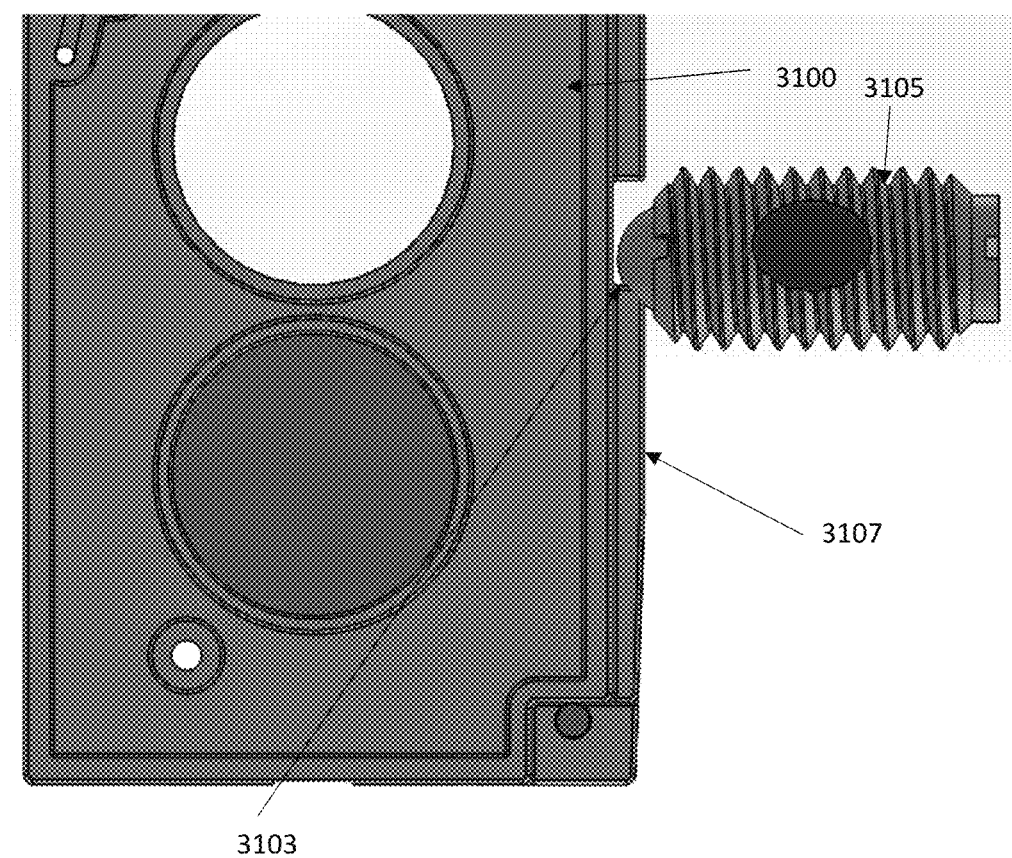
FIGS. 31 and 32 show examples illustrating a portion of a cartridge holder including a ball plunger.

FIG. 31 is similar to FIG. 30, in which the cartridge holder has been made transparent, showing just the ball plunger 3105 portion of the cartridge holder, as well as a portion of a cartridge 3100. As in FIG. 30, the ball plunger rests on a corner 3103 of the cartridge (shoulder region) when the cartridge. As the cartridge is inserted into the cartridge holder, the ball plunger pushes against a side surface 3107 of the cartridge, which forces the cartridge against the reference wall (e.g., the y reference surface).

Figure 32:
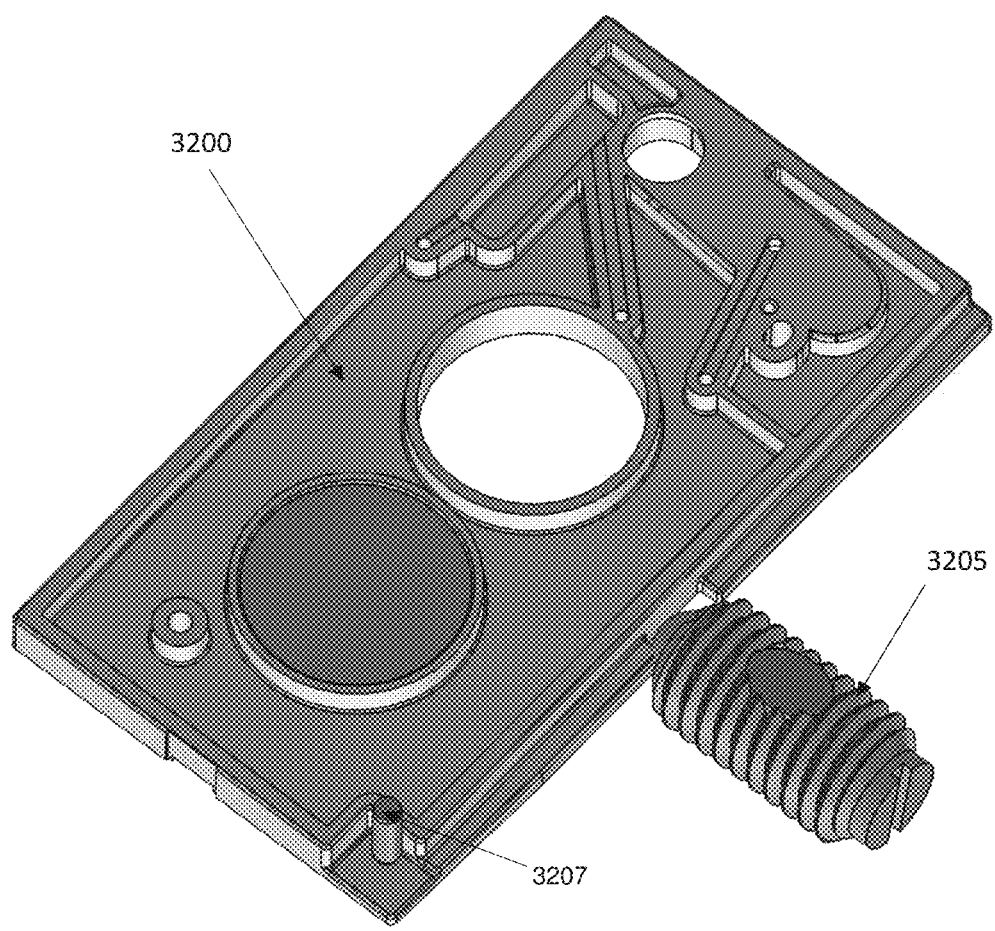

Similarly, as shown in FIG. 32, the cartridge 3200 (top half of a cartridge is shown in FIG. 32) may include a shoulder region (part of a cut out portion on the lateral side of the cartridge) that the ball plunger 3205 may engage with. The cartridge may also include one or more reference pins 3207 and/or walls.

Figure 33:
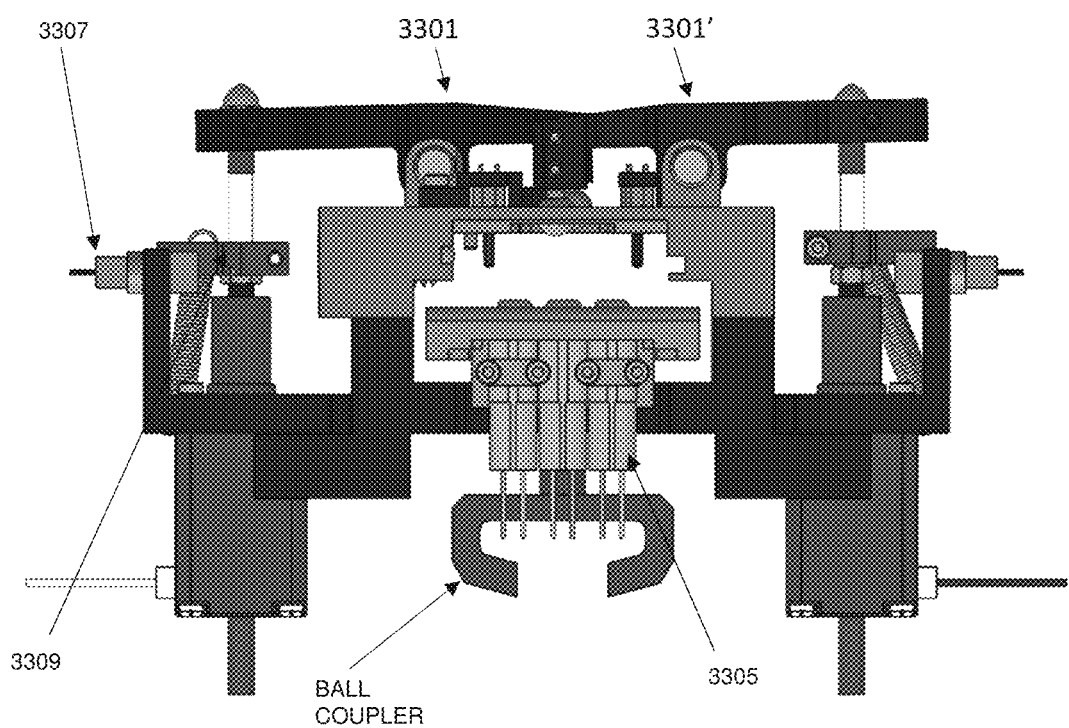
FIG. 33 schematically illustrates one example of a portion of a reader.

As mentioned, any of these apparatuses may include one or more actuators (e.g., mechanical actuators, valve actuators, etc.) for processing the sample, including the valve actuators 3305 and one or more mechanical actuators for applying force to the cartridge, e.g., a membrane on the cartridge, to move fluid. The mechanical actuator may be a piston or, as shown in FIG. 33, a rocker arm 3301, 3301' that is motor controlled. In FIG. 33, the rocker arms may be independently controlled to assist in precise metering and movement of the fluid in the cartridge. In FIG. 33, an optical sensor 3307 may detect when the cartridge is inserted into the holder, as well as one or more additional sensor components, such as a flange 3309 for home positioning sensors (e.g., detecting the position of the cartridge holder and/or cartridge. In some variations the sensor 3307 and/or additional sensors may detect fluid within the cartridge held in the cartridge holder.

Figure 34:
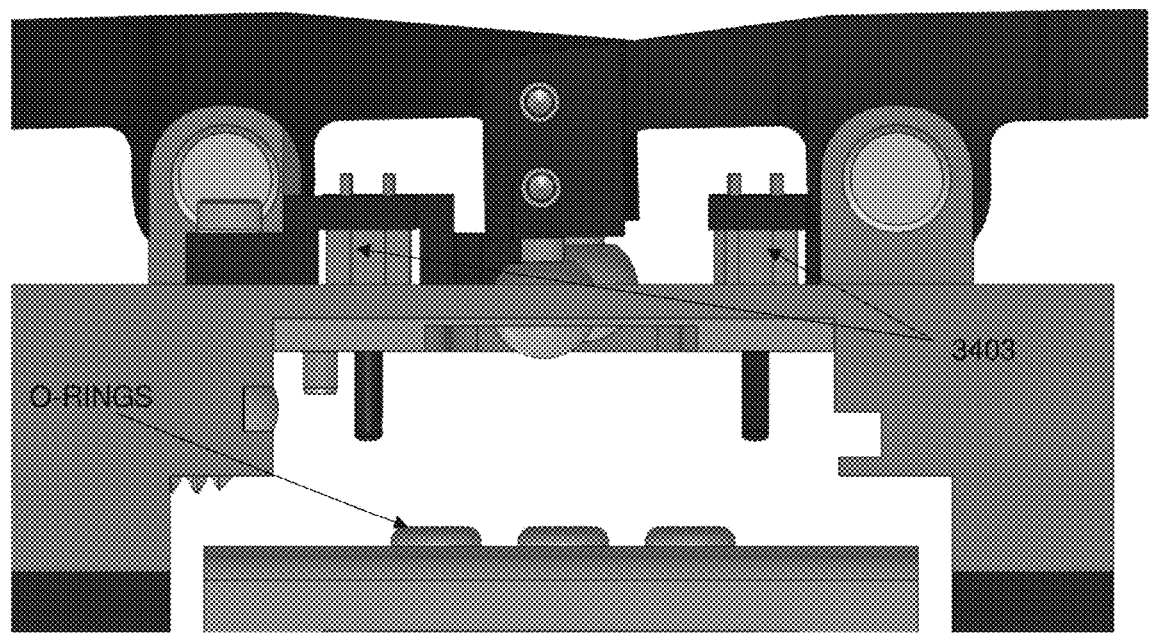
FIG. 34 is an enlarged view of FIG. 33.

For example, a reader, including the cartridge holder portion of the reader, may include additional sensors for monitoring processes within the cartridge, in addition to monitoring the position of the cartridge. For example, FIG. 34 shows an example of a pair of optical sensors 3403 for monitoring fluid within the cartridge, including (as discussed above) the presence of fluid in the mixing channel, etc. FIG. 34 also shows detail of the seals (e.g., O-rings) that may be included as part of the cartridge holder portion of the reader (alternatively in some variations, they may be part of the cartridge, or of both the cartridge and the reader). The O-Rings provide an air tight seal between the cartridge and the clamp base.

Figure 35:
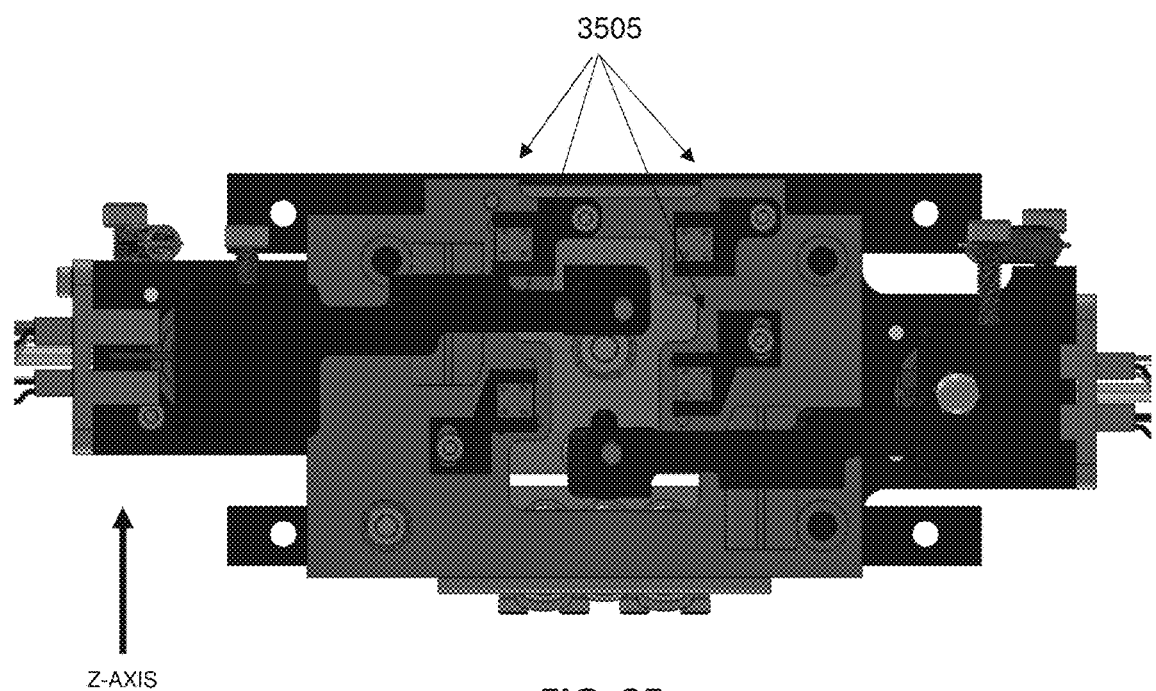
FIG. 35 is a top view of a portion of the reader.

FIG. 35 shows an overhead view of the optical sensors for fluid monitoring similar to the side view shown in FIG. 34. Thus, in this example, four fluid sensors 3505 are included.

Figure 36:
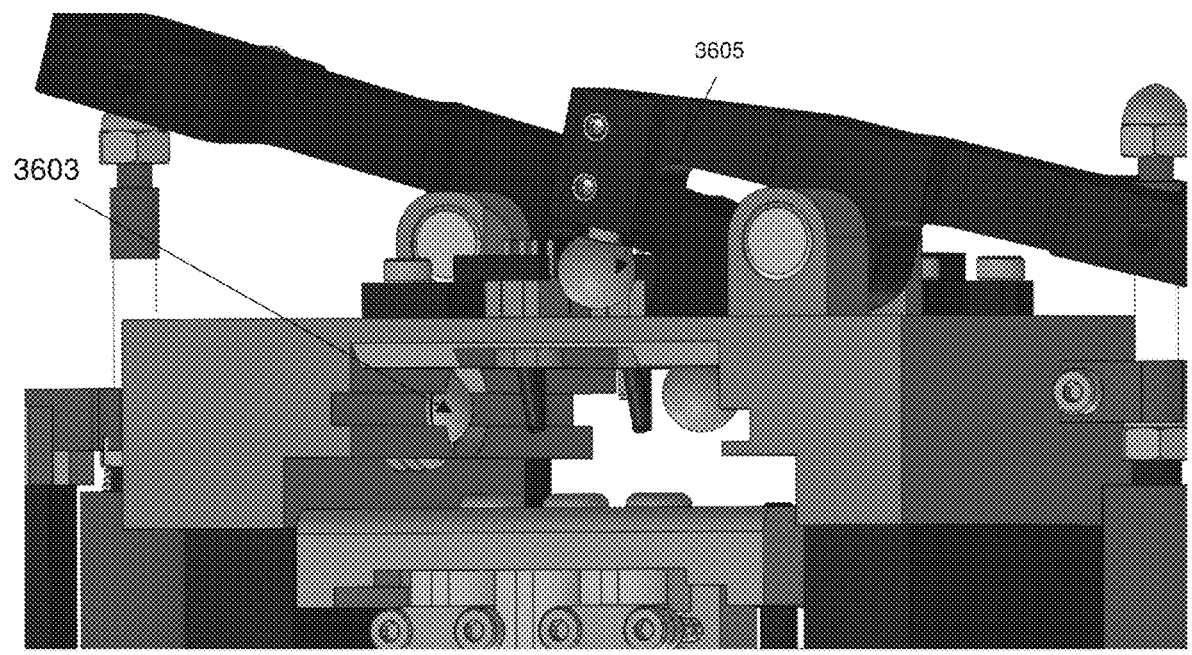
FIG. 36 is an example of a cartridge holder portion of a reader.

FIG. 36 shows another view of a cartridge holder portion of a reader apparatus, without a cartridge inserted into it. In FIG. 36, the ball plunger 3603 shown on one side of cartridge-holding portion, and a pair of mechanical regulators, showing as rocking arms that include a tooling ball 3605 at the end of the rocking arm, to apply force to the cartridge, such as a pump membrane, in order to drive fluid through the cartridge. In this example, the tooling ball provides a spherical contact surface between itself and a pump membrane (e.g., pump diaphragm) or a blister pack. The spherical shape may provide a constant contact shape throughout the slight arc of the tooling ball's path. The contact surface area may change throughout the travel because the ball may go deeper into the blister pack and/or pump membrane.

Figure 37:
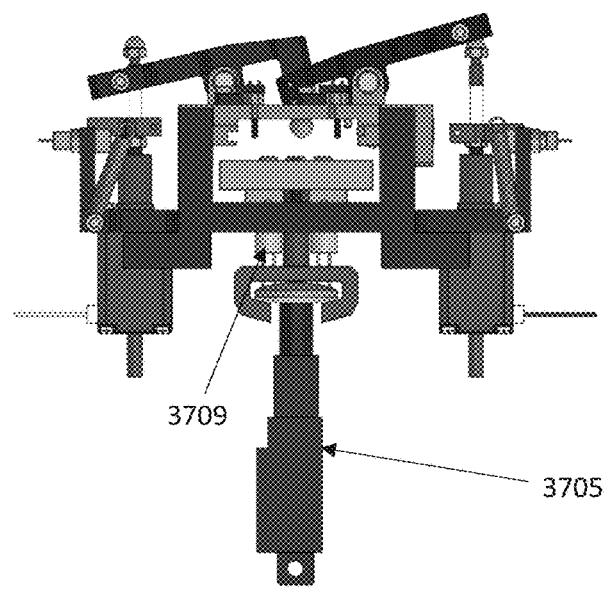
FIGS. 37 and 38 show linear drive actuator(s) coupled to the cartridge holder portion of a reader.
Figure 38:
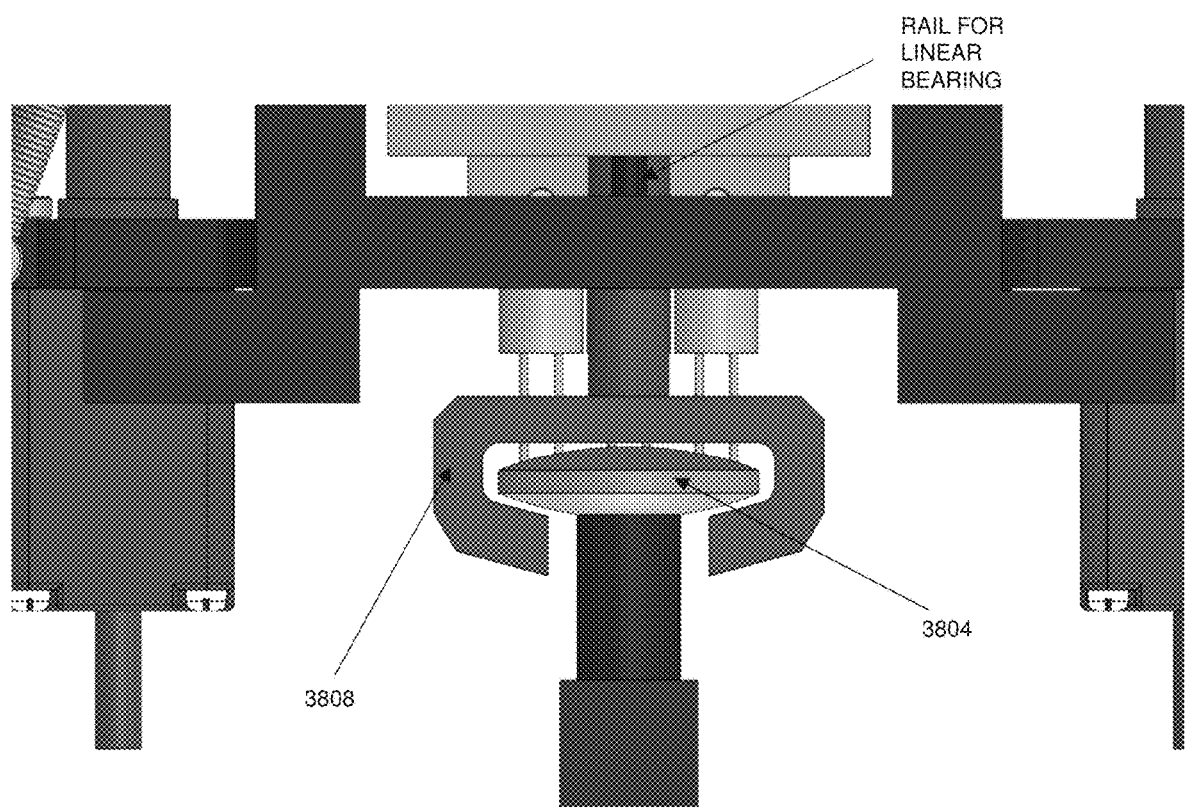

In some variations the pistons of the valves may be actuated by a linear actuator 3705, as shown in FIG. 37. In this example the valves 3709 that may be controlled by the controller of the apparatus (not shown in FIG. 37) to regulate the flow of fluid in the cartridge. As shown in FIG. 38 the linear actuator may be coupled to a ball coupler assembly 3708 that may provide a means of moving a base plate up and down (opening and closing) which holds the cartridge in place during a scan. This mechanism does not bind and is not subject to axial alignment issues because the ball plunger and ball plunger coupler 3804 are not rigidly coupled. Also, the contact surfaces between the two parts are a radius and a plane, again removing any alignment issues. In this example, the cartridge holder includes a clamp base that rides on linear bearings.

Figure 40:
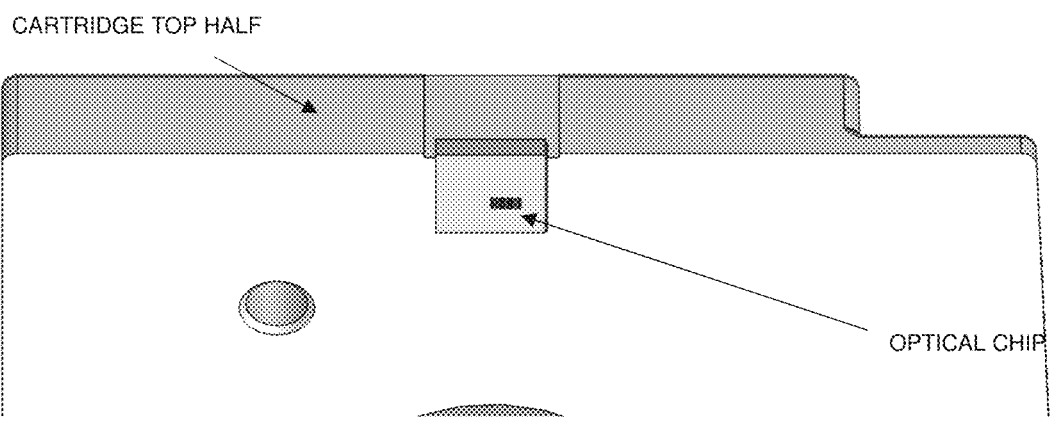
FIGS. 40, 41 and 42 illustrate specific features of an exemplary cartridge that may be used in any of the apparatuses described herein.
Figure 41:
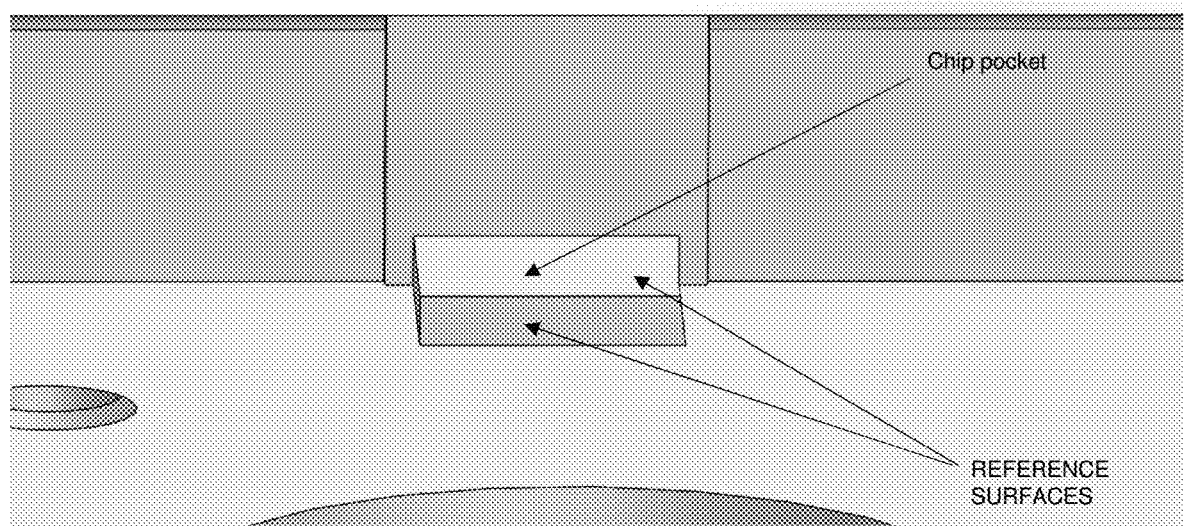
Figure 42:
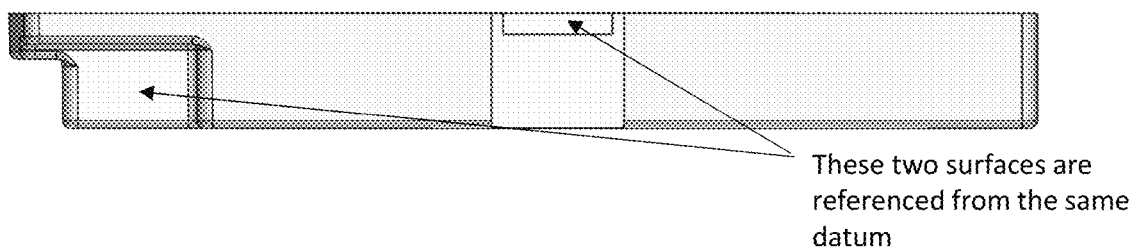

FIGS. 40-42 show one example of the placement of the chip (e.g., photonic chip) for use in their investigation. As shown in FIG. 41, the chip may be positioned in a chip pocket within the cartridge and connected to the fluid channels for washing, binding, rinsing, etc.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An optical reader device for reading a photonic chip of a removable cartridge, the device comprising:
   a cartridge holder comprising a slot extending into the optical reader, the slot having a height and a width;
   a scan head, wherein the scan head comprises a first plurality of optical fibers forming a first plurality of optical fiber ends that are optically connected to one or more laser light sources and a second plurality of optical fibers forming a second plurality of optical fiber ends that are optically connected to a plurality of detectors;

a scan head actuator configured to move the scan head relative to the cartridge holder;
a plurality of valves on the cartridge holder that are configured to couple with valve openings in the removable cartridge;
a pump membrane actuator on the cartridge holder that is configured to apply force to a membrane pump of the removable cartridge, wherein the pump membrane actuator is configured to hold a plurality of extended positions to deflect or relax deflection of the membrane pump;
a controller configured to coordinate movement of the scan head, illumination of the one or more laser light sources, detection by the plurality of detectors, opening and closing of the plurality of valves and positioning of the pump membrane actuator when the removable cartridge is inserted into the cartridge holder; and
a plurality of fluid sensors in communication with the controller and configured to optically detect fluid within one or more regions of the removable cartridge.

2. The device of claim 1, wherein the controller is configured to clamp the cartridge holder when the removable cartridge is inserted in to the cartridge holder.

3. The device of claim 1, wherein the scan head comprises a linear array of the first plurality of optical fiber ends and the second plurality of optical fiber ends.

4. The device of claim 1, wherein each valve of the plurality of valves comprises a seal configured to be moved relative to the cartridge holder to open or close a valve opening in the removable cartridge when the removable cartridge is held within the cartridge holder.

5. The device of claim 1, wherein the pump membrane actuator comprises an arm and a driver.

6. The device of claim 1, wherein the pump membrane actuator comprises a rounded, ball-shaped end.

7. The device of claim 1, wherein the pump membrane actuator comprises a rocker arm that is motor driven.

8. The device of claim 1, further comprising a blister pack arm on the cartridge holder configured to apply force to a blister pack of the removable cartridge.

9. The device of claim 1, further comprising a temperature sensor on the cartridge holder and a heater on the cartridge holder, wherein the controller is further configured to regulate a temperature of a removable cartridge held in the cartridge holder.

10. An optical reader device for reading a photonic chip of a removable cartridge, the device comprising:
    a reader housing;
    a cartridge holder comprising a slot extending into the reader housing, the slot having a height and a width;
    a scan head within the reader housing, wherein the scan head comprises a first plurality of optical fibers forming a first plurality of optical fiber ends that are optically connected to one or more laser light sources and a second plurality of optical fibers forming a second plurality of optical fiber ends that are optically connected to a plurality of detectors, further wherein the optical fiber ends within the first and second plurality of optical fiber ends are arranged in a line;
    a scan head actuator configured to move the scan head relative to the cartridge holder;
    a plurality of valves on the cartridge holder that are configured to couple with valve openings in the removable cartridge;
    a pump membrane actuator comprising a rocker arm having a rounded end, wherein the pump membrane actuator is configured to apply force to a membrane pump of the removable cartridge, wherein the pump membrane actuator is configured to hold a plurality of extended positions to deflect or relax deflection of the membrane pump; and
    a controller configured to coordinate movement of the scan head, illumination of the one or more laser light sources, detection by the plurality of detectors, opening and closing of the plurality of valves and positioning of the pump membrane actuator when the removable cartridge is held in the cartridge holder.

11. The device of claim 10 further comprising a plurality of fluid sensors in communication with the controller and configured to optically detect fluid within one or more regions of the removable cartridge.

12. The device of claim 10, wherein the controller is configured to clamp the cartridge holder when the removable cartridge is inserted in to the cartridge holder.

13. The device of claim 10, wherein each valve of the plurality of valves comprises a seal configured to be moved relative to the cartridge holder to open or close a valve opening in the removable cartridge when the removable cartridge is held within the cartridge holder.

14. The device of claim 10, further comprising a blister pack arm on the cartridge holder configured to apply force to a blister pack of the removable cartridge.

15. The device of claim 10, further comprising a temperature sensor on the cartridge holder and a heater on the cartridge holder, wherein the controller is further configured to regulate a temperature of a removable cartridge held in the cartridge holder.

16. An optical reader device for reading a photonic chip of a removable cartridge, the device comprising:
    a cartridge holder comprising a slot extending in a z-axis into the optical reader, the slot having a height in a y-axis direction and a width in an x-axis direction,
    a ball plunger on one side of the slot, the ball plunger biased to extend into the slot in the x-axis direction, configured to drive the removable cartridge against a reference surface in the z-axis and a reference surface in the x-axis direction;
    a movable clamp base configured to apply force in the y-axis direction to secure the removable cartridge within the slot and to drive the removable cartridge against a reference surface in the y-axis direction;
    a scan head configured to move relative to the cartridge holder, wherein the scan head comprises a first plurality of optical fiber ends optically connected to one or more laser light sources and a second plurality of optical fiber ends optically connected to a plurality of detectors; and
    a controller configured to coordinate movement of the movable clamp base, movement of the scan head, illumination of the one or more laser light sources and detection by the plurality of detectors.

17. The device of claim 16, wherein the reference surface in the z-axis is a pin extending into the slot.

18. The device of claim 16, further comprising a scan head actuator configured to move the scan head relative to the cartridge holder.

19. The device of claim 16, further comprising a plurality of valves on the cartridge holder that are configured to couple with valve openings in the removable cartridge.

20. The device of claim 16, further comprising a pump membrane actuator on the cartridge holder that is configured to apply force to a membrane pump of the removable cartridge, wherein the pump membrane actuator is configured to hold a plurality of extended positions to deflect or relax deflection of the membrane pump.

21. The device of claim 20, wherein the pump membrane actuator comprises an arm and a driver.

22. The device of claim 20, wherein the pump membrane actuator comprises a rounded, ball-shaped end.

23. The device of claim 20, wherein the pump membrane actuator comprises a rocker arm that is motor driven.

24. The device of claim 16, further comprising a plurality of fluid sensors in communication with the controller and configured to optically detect fluid within one or more regions of the removable cartridge.

25. The device of claim 16, wherein the controller is configured to clamp the movable clamp base to apply force in the y-axis direction to secure the removable cartridge when the removable cartridge is inserted in to the cartridge holder.

26. The device of claim 16, wherein the scan head comprises a linear array of the first plurality of optical fiber ends and the second plurality of optical fiber ends.

27. The device of claim 16, further comprising a blister pack arm on the cartridge holder configured to apply force to a blister pack of the removable cartridge.

28. The device of claim 16, further comprising a temperature sensor on the cartridge holder and a heater on the cartridge holder, wherein the controller is further configured to regulate a temperature of a removable cartridge held in the cartridge holder.

29. An optical reader device for reading a photonic chip of a removable cartridge, the device comprising:
 a reader housing including a cartridge interface;
 a cartridge holder comprising a slot extending in a z-axis into the reader housing, the slot having a height in a y-axis direction and a width in an x-axis direction,
 a ball plunger on one side of the slot, the ball plunger biased to extend into the slot in the x-axis direction, configured to drive the removable cartridge against a reference surface in the z-axis and a reference surface in the x-axis direction;
 a movable clamp base configured to apply force in the y-axis direction to secure the removable cartridge within the slot and to drive the removable cartridge against a reference surface in the y-axis direction;
 a scan head configured to move relative to the cartridge holder, wherein the scan head comprises a first plurality of optical fiber ends optically connected to one or more laser light sources and a second plurality of optical fiber ends optically connected to a plurality of detectors;
 a pump membrane actuator within the reader housing and configured to apply force to a membrane pump of the removable cartridge, wherein the pump membrane actuator is configured to hold a plurality of extended positions to deflect or relax deflection of the membrane pump; and
 a controller configured to coordinate movement of the movable clamp base, movement of the scan head, illumination of the one or more laser light sources and detection by the plurality of detectors.

30. The device of claim 29, wherein the reference surface in the z-axis is a pin extending into the slot.

31. The device of claim 29, further comprising a scan head actuator configured to move the scan head relative to the cartridge holder.

32. The device of claim 29, further comprising a plurality of valves on the cartridge holder that are configured to couple with valve openings in the removable cartridge.

33. The device of claim 29, wherein the pump membrane actuator comprises an arm and a driver.

34. The device of claim 29, wherein the pump membrane actuator comprises a rounded, ball-shaped end.

35. The device of claim 29, wherein the pump membrane actuator comprises a rocker arm that is motor driven.

36. The device of claim 29, further comprising a plurality of fluid sensors in communication with the controller and configured to optically detect fluid within one or more regions of the removable cartridge.

37. The device of claim 29, wherein the controller is configured to clamp the movable clamp base to apply force in the y-axis direction to secure the removable cartridge when the removable cartridge is inserted in to the cartridge holder.

38. The device of claim 29, wherein the scan head comprises a linear array of the first plurality of optical fiber ends and the second plurality of optical fiber ends.

39. The device of claim 29, further comprising a blister pack arm on the cartridge holder configured to apply force to a blister pack of the removable cartridge.

40. The device of claim 29, further comprising a temperature sensor on the cartridge holder and a heater on the cartridge holder, wherein the controller is further configured to regulate a temperature of a removable cartridge held in the cartridge holder.

* * * * *